US012731668B2

(12) United States Patent
Kemper et al.

(10) Patent No.: US 12,731,668 B2
(45) Date of Patent: Sep. 8, 2026

(54) SYSTEM, METHOD, AND COMPUTER PROGRAM PRODUCT FOR PROTOCOL CONVERSION

(71) Applicant: BAYER HEALTHCARE LLC, Whippany, NJ (US)

(72) Inventors: Corey Kemper, Pittsburgh, PA (US); John Volkar, Valencia, PA (US)

(73) Assignee: Bayer HealthCare LLC, Whippany, NJ (US)

( * ) Notice: Subject to any disclaimer, the term of this patent is extended or adjusted under 35 U.S.C. 154(b) by 64 days.

(21) Appl. No.: 18/261,739

(22) PCT Filed: Jan. 26, 2022

(86) PCT No.: PCT/US2022/013774
§ 371 (c)(1),
(2) Date: Jul. 17, 2023

(87) PCT Pub. No.: WO2022/164831
PCT Pub. Date: Aug. 4, 2022

(65) Prior Publication Data

US 2024/0120060 A1 Apr. 11, 2024

Related U.S. Application Data

(60) Provisional application No. 63/143,297, filed on Jan. 29, 2021.

(51) Int. Cl.
*G16H 20/17* (2018.01)
*A61B 5/103* (2006.01)
(Continued)

(52) U.S. Cl.
CPC ............ *G16H 20/17* (2018.01); *A61B 5/103* (2013.01); *G16H 10/20* (2018.01); *G16H 40/60* (2018.01)

(58) Field of Classification Search
CPC ........ G16H 20/17; G16H 20/10; G16H 70/20; G16H 20/13
See application file for complete search history.

(56) References Cited

U.S. PATENT DOCUMENTS 6,643,537 B1 11/2003 Zatezalo et al.
7,094,216 B2 8/2006 Trombley, III et al.
(Continued)

FOREIGN PATENT DOCUMENTS

JP 5203971 B2 6/2013
JP 2018130231 A 8/2018
(Continued)

OTHER PUBLICATIONS

Potthast, S., et al. "Low-dose intra-arterial contrast-enhanced MR aortography in patients based on a theoretically derived injection protocol." European radiology 15 (2005): 2347-2353. (Year: 2005).*
(Continued)

*Primary Examiner* — Constantine Siozopoulos
(74) *Attorney, Agent, or Firm* — James Stevenson; Aaron Mace; Joseph Kent

(57) ABSTRACT

A system, method, and computer program product for protocol conversion may obtain a fixed protocol including the following fixed protocol parameters: a flow rate of at least one fluid to be delivered to a patient in at least one phase of an injection and a volume of the at least one fluid to be delivered to the patient in the at least one phase of the injection; provide a series of prompts, and receive a series of user responses in response to the series of prompts; and generate, based on the series of user responses and the fixed protocol, a smart protocol including the following smart protocol parameters according to which the injection system
(Continued)

is configured to control delivery of the at least one fluid to the patient in the injection: a dosing factor and a dosing method.

17 Claims, 25 Drawing Sheets

(51) Int. Cl.

| | |
|---|---|
| ***G16H 10/20*** | (2018.01) |
| ***G16H 40/60*** | (2018.01) |

(56) References Cited

U.S. PATENT DOCUMENTS

| | | | |
|---|---|---|---|
| 7,556,619 B2 | 7/2009 | Spohn et al. | |
| 8,147,464 B2 | 4/2012 | Spohn et al. | |
| 8,337,456 B2 | 12/2012 | Schriver et al. | |
| 8,540,698 B2 | 9/2013 | Spohn et al. | |
| 2008/0119715 A1 | 5/2008 | Gonzalez Molezzi et al. | |
| 2013/0345548 A1* | 12/2013 | Hynes | A61M 5/007 600/420 |
| 2019/0035500 A1* | 1/2019 | Saint | H04B 7/24 |

FOREIGN PATENT DOCUMENTS

| | | | | |
|---|---|---|---|---|
| JP | 6618673 B2 | 12/2019 | | |
| JP | 6644469 B2 | 2/2020 | | |
| JP | 6676377 B2 | 4/2020 | | |
| WO | 2008085421 A2 | 7/2008 | | |
| WO | WO-2021067856 A1 * | 4/2021 | | A61B 5/14532 |

OTHER PUBLICATIONS

Bae Kyongtae, Intravenous Contrast Medium Administration and Scan Timing at CT: Considerations and Approaches, Radiology, Jul. 2010, vol. 256: No. 1, pp. 32-61.

International Preliminary Report on Patentability from PCT Application No. PCT/US2022/013774, mailed Aug. 10, 2023.

Rutten Annemaricke et al., Biphasic contrast medium injection in cardiac CT: moderate versus high concentration contrast material at identical iodine flux and iodine dose, Eur. Radiol, 2010, 20, 1917-1925.

Seifarth Harold, et at., Introduction of an individually optimized protocol for the injection of contrast medium for coronary CT angiography, Eur. Radiol., 2009, 19, 2373-2382.

* cited by examiner

FIG. 5
500
Q1 :
What Conc?
Q2 :
Size Adapt?
When Yes
Q21 :
Adapt On?
Q3 :
Is for CTA?
When Yes,
Q31 :
Adjust Duration?
When Yes
Q32 :
Max Rate?
Q33 :
Min Rate?
When Q2 No,
Q34 :
Max Vol?
Q35 :
Min Vol?
Q4 : When Q2 Yes,
Is for Avg Size?
When Yes
Q41a
Use Q21 to pick a or b.
When No,
Q41b
Use Q21 to pick c or d.
Q42a :
Avg Weight?
Q42b :
Avg LBW?
Q42c :
Target Weight?
Q42d :
Target LBW?
Q43 : Max Vol?
Q44 : Min Vol?
Q5 : When Q31 No
Scan Timing?
When "Fixed Delays",
When "Bolus Tracking"
Q51 :
Fixed Dur. Okay?
When Yes
Q52 : Max Rate?
Q53 : Min Rate?

SYSTEM, METHOD, AND COMPUTER PROGRAM PRODUCT FOR PROTOCOL CONVERSION

CROSS-REFERENCE TO RELATED APPLICATIONS

This application is a U.S. national phase application under 35 U.S.C. § 371 of International Application No. PCT/US2022/013774, filed Jan. 26, 2022, and claims the benefit of U.S. Provisional Application No. 63/143,297, filed Jan. 29, 2021, the disclosures of which is are hereby incorporated by reference in its entirety their entireties.

BACKGROUND

1. Field

This disclosure relates generally to fluid injections, and in some non-limiting embodiments or aspects, to converting protocols for fluid injections.

2. Technical Considerations

Although it is scientifically accepted to modify injection protocols based on patient habitus (e.g., height, weight, age, cardiac output, blood volume, etc.), contrast media concentration, and/or scanner parameters, it is not yet common clinical practice to do so due to a variety of reasons. For example, many injectors only allow for programming and storing injection protocols using a series of flow rates and volumes of each fluid type (e.g., 80 ml @ 5 ml/s of contrast media, followed by 40 ml @ 5 ml/s of a saline flush, etc.). For the sake of simplicity, this often leads to using the same fixed protocol for a clinical indication, regardless of patient size and/or variations in scanner settings that affect scan timing. Alternatively, a technologist/radiographer may calculate a protocol using spreadsheets and/or look-up tables, or make an arbitrary judgment based on their experience and the patient being scanned.

An exception to these out-of-date clinical practices is Personalized Patient Protocol Technology (P3T®) Dosing Software marketed and sold by Bayer HealthCare LLC. P3T® software takes patient weight and/or other parameters into account in order to calculate an injection protocol. P3T® may have specific indications and clinical validations, which means that P3T® may be limited in its application and/or may not fit the preferences of a particular clinician for contrast enhancement.

SUMMARY

Accordingly, provided are improved systems, devices, products, apparatus, and/or methods for protocol conversion. For example, non-limiting embodiments or aspects of the present disclosure may provide a series of user questions/answers for converting a standard injection protocol including flow rates and volumes (e.g., a "fixed" or "legacy" protocol) to one that is based on contrast media (e.g., iodine, etc.) delivery rate and/or contrast media (e.g., iodine, etc.) load that is specific to a patient, the contrast media and scanner parameters (e.g., a "smart" protocol, etc.). As an example, non-limiting embodiments or aspects of the present disclosure may enable conversion of existing protocols (e.g., fixed protocols, etc.) to smart protocols that match clinical intentions and/or meet needs for specific study types and patient populations thereof without either a) requiring an in-depth understanding of contrast media literature and/or pharmacokinetic models for contrast media propagation, or b) requiring development and validation of a new dedicated algorithm for each different clinical indication. For example, instead of providing a protocol calculation algorithm (e.g., P3T®, etc.), non-limiting embodiments or aspects of the present disclosure provide systems, devices, products, apparatus, and/or methods that enable a user to easily convert an existing protocol to a more scientifically correct method of dosing. In this way, when a user installs/configures a new injector, assuming the user has an existing protocol library and a desire to use "smart" protocols, the user may import the existing protocols and convert each existing protocol that is compatible with the smart protocol structure. Moreover, even after installing a smart protocol compatible injector, if the user later decide to enable/purchase smart protocols, the user may pick and choose which existing protocols to convert to smart protocols, which enables self-service by the user, reduces time spent by clinical support specialists at a site, and improves the quality of injection protocols being delivered by tailoring contrast media dose and timing to the patient and to the scan, and/or improves workflow for the user by reducing manual edits to protocols and/or the use of lookup tables and calculators.

According to some non-limiting embodiments or aspects, provided is a system, including: at least one processor programmed and/or configured to: obtain a fixed protocol including the following fixed protocol parameters according to which an injection system is configured to control delivery of at least one fluid to a patient in an injection: a flow rate of the at least one fluid to be delivered to the patient in at least one phase of the injection and a volume of the at least one fluid to be delivered to the patient in the at least one phase of the injection; provide, via a user interface of a computing device, a series of prompts, and receive, via the user interface of the computing device, a series of user responses in response to the series of prompts; and generate, based on the series of user responses and the fixed protocol, a smart protocol including the following smart protocol parameters according to which the injection system is configured to control delivery of the at least one fluid to the patient in the injection: a dosing factor and a dosing method, wherein the dosing factor is associated with a number of units of a contrast media to be delivered per a unit of weight, and wherein the dosing method is associated with one of a contrast media load and a contrast media delivery rate.

In some non-limiting embodiments or aspects, the at least one processor is further programmed and/or configured to: determine, based on the parameters of the fixed protocol, whether the fixed protocol is eligible to be converted to a smart protocol.

In some non-limiting embodiments or aspects, the computing device includes at least one of the following: the injection system, a user device, or any combination thereof.

In some non-limiting embodiments or aspects, the at least one processor is further programmed and/or configured to: provide, via the user interface of the computing device, in response to receiving a user response of the user responses, information associated with a change in the smart protocol generated by that user response.

In some non-limiting embodiments or aspects, the at least one processor is further programmed and/or configured to: receive, via the user interface of the computing device, user input associated with the smart protocol for the injection; calculate, based on the user input, values of the smart protocol parameters of the smart protocol; and control, according to the values of the smart protocol parameters of the smart protocol, the injection system to deliver the at least one fluid to the patient in the injection.

In some non-limiting embodiments or aspects, the user input includes at least one of the following: a weight of the patient, a lean body weight of the patient, a body surface area of the patient, or any combination thereof.

In some non-limiting embodiments or aspects, the series of prompts and the series of user responses thereto include a prompt and a corresponding user response thereto for at least one of the following: a concentration of the contrast media; an indication of whether the fixed protocol is adapted based on a size of the patient; an indication of whether to adapt the smart protocol based on the size of the patient; an indication of whether the fixed protocol is for computed tomography angiography (CTA); an indication of whether a duration of the fixed protocol is adjusted based on a duration of a CTA scan; a maximum flow rate of the at least one fluid associated with the fixed protocol, a minimum flow rate of the at least one fluid associated with the fixed protocol; a maximum volume of the at least one fluid associated with the fixed protocol; a minimum volume of the at least one fluid associated with the fixed protocol; an indication of whether the fixed protocol is associated with an average sized patient; a weight of the average sized patient; a lean body weight of the average sized patient; a target weight of the patient; a target lean body weight of the patient, an indication of a type of delivery method associated with the fixed protocol; an indication of whether a fixed duration for the smart protocol is acceptable; or any combination thereof.

In some non-limiting embodiments or aspects, the series of prompts and the series of user responses thereto include a prompt and a corresponding user response thereto for the indication of the type of delivery method associated with the fixed protocol, and wherein the indication of the type of delivery method associated with the fixed protocol includes a bolus tracking delivery method or a fixed delays delivery method.

In some non-limiting embodiments or aspects, the at least one processor is programmed and/or configured to provide the series of prompts, and receive the series of user responses in response to the series of prompts by: providing a prompt for a concentration of the contrast media, and receiving a user response including the concentration of the contrast media; providing a prompt for an indication of whether the fixed protocol is adapted based on a size of the patient, and receiving a user response including the indication of whether the fixed protocol is adapted based on the size of the patient; in response to receiving a user response including an indication that the fixed protocol is adapted based on the size of the patient, providing a prompt for an indication of whether to adapt the smart protocol based on the size of the patient, and receiving a user response including the indication of whether to adapt the smart protocol based on a size of the patient; in response to receiving (i) a user response including an indication that the fixed protocol is not adapted based on the size of the patient or (ii) receiving the user response including the indication of whether to adapt the smart protocol based on the size of the patient, providing a prompt for an indication of whether the fixed protocol is for computed tomography angiography (CTA), and receiving a user response including the indication of whether the fixed protocol is for CTA; providing a prompt for an indication of a type of delivery method associated with the fixed protocol, and receiving a user response including the indication of the type of delivery method associated with the fixed protocol; in response to receiving the user response including the indication that the type of delivery method associated with the fixed protocol is a bolus tracking delivery method, providing a prompt for an indication of whether a duration of the fixed protocol is adjusted based on a duration of a CTA scan, and receiving a user response including the indication of whether a duration of the fixed protocol is adjusted based on the duration of the CTA scan; in response to (i) receiving a user response including an indication that the type of delivery method associated with the fixed protocol is a fixed delays delivery method or (ii) receiving a user response including the indication that the duration of the fixed protocol is adjusted based on the duration of the CTA scan, providing a prompt for a maximum flow rate of the at least one fluid associated with the fixed protocol, and receiving a user response including the maximum flow rate of the at least one fluid associated with the fixed protocol; in response to receiving the user response including the maximum flow rate of the at least one fluid associated with the fixed protocol, providing a prompt for a minimum flow rate of the at least one fluid associated with the fixed protocol, and receiving a user response including the minimum flow rate of the at least one fluid associated with the fixed protocol; in response to receiving (i) the user response including the indication to adapt the smart protocol based on the size of a patient and (ii) the user response including the indication that the fixed protocol is not for CTA or receiving (i) the user response including the minimum flow rate of the at least one fluid associated with the fixed protocol, or receiving (i) the user response including the indication that the fixed duration for the smart protocol is acceptable, providing a prompt for an indication of whether the fixed protocol is associated with an average sized patient, and receiving a user response including the indication of whether the fixed protocol is associated with the average sized patient; in response to receiving the user response including the indication that the fixed protocol is associated with the average sized patient, providing a prompt for at least one of a weight of the average sized patient and a lean body weight of the average sized patient, and receiving a user response including the at least one of the weight of the average sized patient and the lean body weight of the average sized patient; in response to receiving the user response including the indication that the fixed protocol is not associated with the average sized patient, providing a prompt for at least one of a target weight of the patient and a target lean body weight of the patient, and receiving a user response including the at least one of the target weight of the patient and the target lean body weight of the patient; in response to receiving (i) the user response including the at least one of the weight of the average sized patient and the lean body weight of the average sized patient or (ii) the user response including the at least one of the target weight of the patient and the target lean body weight of the patient, providing a prompt for a maximum volume of the at least one fluid associated with the fixed protocol, and receiving a user response including the maximum volume of the at least one fluid associated with the fixed protocol; in response to receiving the user response including the maximum volume of the at least one fluid associated with the fixed protocol, providing a prompt for a minimum volume of the at least one fluid associated with the fixed protocol, and receiving a user response including the minimum volume of at least one fluid associated with a fixed protocol; in response to receiving the user response including the indication that the fixed protocol is for CTA, providing a prompt for an indication of whether a fixed duration for the smart protocol is acceptable, and receiving a user response including the indication of whether the fixed duration for the smart protocol is acceptable; in response to receiving the user response including the indication that the fixed duration for the smart protocol is acceptable, providing the prompt for the maximum flow rate of the at least one fluid associated with the fixed protocol, and receiving the user response including the maximum flow rate of the at least one fluid associated with the fixed protocol; and in response to receiving the user response including the indication to not adapt the smart protocol based on the size of the patient, providing a prompt for the maximum volume of the at least one fluid associated with the fixed protocol, and receiving the user response including the maximum volume of the at least one fluid associated with the fixed protocol.

In some non-limiting embodiments or aspects, the smart protocol includes an iodine dose/load (IDL)-based protocol or an iodine delivery rate (IDR)-based protocol.

According to some non-limiting embodiments or aspects, provided is a computer-implemented method, including: obtaining, with at least one processor, a fixed protocol including the following fixed protocol parameters according to which an injection system is configured to control delivery of at least one fluid to a patient in an injection: a flow rate of the at least one fluid to be delivered to the patient in at least one phase of the injection and a volume of the at least one fluid to be delivered to the patient in the at least one phase of the injection; providing, with the at least one processor, via a user interface of a computing device, a series of prompts, and receiving, with the at least one processor, via the user interface of the computing device, a series of user responses in response to the series of prompts; and generate, with the at least one processor, based on the series of user responses and the fixed protocol, a smart protocol including the following smart protocol parameters according to which the injection system is configured to control delivery of the at least one fluid to the patient in the injection: a dosing factor and a dosing method, wherein the dosing factor is associated with a number of units of a contrast media to be delivered per a unit of weight, and wherein the dosing method is associated with one of a contrast media load and a contrast media delivery rate.

In some non-limiting embodiments or aspects, the method further includes: determining, with the at least one processor, based on the parameters of the fixed protocol, whether the fixed protocol is eligible to be converted to a smart protocol.

In some non-limiting embodiments or aspects, the computing device includes at least one of the following: the injection system, a user device, or any combination thereof.

In some non-limiting embodiments or aspects, the method further includes: providing, with the at least one processor, via the user interface of the computing device, in response to receiving a user response of the user responses, information associated with a change in the smart protocol generated by that user response.

In some non-limiting embodiments or aspects, the method further includes receiving, with the at least one processor, via the user interface of the computing device, user input associated with the smart protocol for the injection; calculating, with the at least one processor, based on the user input, values of the smart protocol parameters of the smart protocol; and controlling, with the at least one processor, according to the values of the smart protocol parameters of the smart protocol, the injection system to deliver the at least one fluid to the patient in the injection.

In some non-limiting embodiments or aspects, the user input includes at least one of the following: a weight of the patient, a lean body weight of the patient, a body surface area of the patient, or any combination thereof.

In some non-limiting embodiments or aspects, the series of prompts and the series of user responses thereto include a prompt and a corresponding user response thereto for at least one of the following: a concentration of the contrast media; an indication of whether the fixed protocol is adapted based on a size of the patient; an indication of whether to adapt the smart protocol based on the size of the patient; an indication of whether the fixed protocol is for computed tomography angiography (CTA); an indication of whether a duration of the fixed protocol is adjusted based on a duration of a CTA scan; a maximum flow rate of the at least one fluid associated with the fixed protocol, a minimum flow rate of the at least one fluid associated with the fixed protocol; a maximum volume of the at least one fluid associated with the fixed protocol; a minimum volume of the at least one fluid associated with the fixed protocol; an indication of whether the fixed protocol is associated with an average sized patient; a weight of the average sized patient; a lean body weight of the average sized patient; a target weight of the patient; a target lean body weight of the patient, an indication of a type of delivery method associated with the fixed protocol; an indication of whether a fixed duration for the smart protocol is acceptable; or any combination thereof.

In some non-limiting embodiments or aspects, the series of prompts and the series of user responses thereto include a prompt and a corresponding user response thereto for the indication of the type of delivery method associated with the fixed protocol, and wherein the indication of the type of delivery method associated with the fixed protocol includes a bolus tracking delivery method or a fixed delays delivery method.

In some non-limiting embodiments or aspects, providing, with the at least one processor, the series of prompts, and receiving, with the at least one processor, the series of user responses in response to the series of prompts further includes: providing a prompt for a concentration of the contrast media, and receiving a user response including the concentration of the contrast media; providing a prompt for an indication of whether the fixed protocol is adapted based on a size of the patient, and receiving a user response including the indication of whether the fixed protocol is adapted based on the size of the patient; in response to receiving a user response including an indication that the fixed protocol is adapted based on the size of the patient, providing a prompt for an indication of whether to adapt the smart protocol based on the size of the patient, and receiving a user response including the indication of whether to adapt the smart protocol based on a size of the patient; in response to receiving (i) a user response including an indication that the fixed protocol is not adapted based on the size of the patient or (ii) receiving the user response including the indication of whether to adapt the smart protocol based on the size of the patient, providing a prompt for an indication of whether the fixed protocol is for computed tomography angiography (CTA), and receiving a user response including the indication of whether the fixed protocol is for CTA; providing a prompt for an indication of a type of delivery method associated with the fixed protocol, and receiving a user response including the indication of the type of delivery method associated with the fixed protocol; in response to receiving the user response including the indication that the type of delivery method associated with the fixed protocol is a bolus tracking delivery method, providing a prompt for an indication of whether a duration of the fixed protocol is adjusted based on a duration of a CTA scan, and receiving a user response including the indication of whether a duration of the fixed protocol is adjusted based on the duration of the CTA scan; in response to (i) receiving a user response including an indication that the type of delivery method associated with the fixed protocol is a fixed delays delivery method or (ii) receiving a user response including the indication that the duration of the fixed protocol is adjusted based on the duration of the CTA scan, providing a prompt for a maximum flow rate of the at least one fluid associated with the fixed protocol, and receiving a user response including the maximum flow rate of the at least one fluid associated with the fixed protocol; in response to receiving the user response including the maximum flow rate of the at least one fluid associated with the fixed protocol, providing a prompt for a minimum flow rate of the at least one fluid associated with the fixed protocol, and receiving a user response including the minimum flow rate of the at least one fluid associated with the fixed protocol; in response to receiving (i) the user response including the indication to adapt the smart protocol based on the size of a patient and (ii) the user response including the indication that the fixed protocol is not for CTA or receiving (i) the user response including the minimum flow rate of the at least one fluid associated with the fixed protocol, or receiving (i) the user response including the indication that the fixed duration for the smart protocol is acceptable, providing a prompt for an indication of whether the fixed protocol is associated with an average sized patient, and receiving a user response including the indication of whether the fixed protocol is associated with the average sized patient; in response to receiving the user response including the indication that the fixed protocol is associated with the average sized patient, providing a prompt for at least one of a weight of the average sized patient and a lean body weight of the average sized patient, and receiving a user response including the at least one of the weight of the average sized patient and the lean body weight of the average sized patient; in response to receiving the user response including the indication that the fixed protocol is not associated with the average sized patient, providing a prompt for at least one of a target weight of the patient and a target lean body weight of the patient, and receiving a user response including the at least one of the target weight of the patient and the target lean body weight of the patient; in response to receiving (i) the user response including the at least one of the weight of the average sized patient and the lean body weight of the average sized patient or (ii) the user response including the at least one of the target weight of the patient and the target lean body weight of the patient, providing a prompt for a maximum volume of the at least one fluid associated with the fixed protocol, and receiving a user response including the maximum volume of the at least one fluid associated with the fixed protocol; in response to receiving the user response including the maximum volume of the at least one fluid associated with the fixed protocol, providing a prompt for a minimum volume of the at least one fluid associated with the fixed protocol, and receiving a user response including the minimum volume of at least one fluid associated with a fixed protocol; in response to receiving the user response including the indication that the fixed protocol is for CTA, providing a prompt for an indication of whether a fixed duration for the smart protocol is acceptable, and receiving a user response including the indication of whether the fixed duration for the smart protocol is acceptable; in response to receiving the user response including the indication that the fixed duration for the smart protocol is acceptable, providing the prompt for the maximum flow rate of the at least one fluid associated with the fixed protocol, and receiving the user response including the maximum flow rate of the at least one fluid associated with the fixed protocol; and in response to receiving the user response including the indication to not adapt the smart protocol based on the size of the patient, providing a prompt for the maximum volume of the at least one fluid associated with the fixed protocol, and receiving the user response including the maximum volume of the at least one fluid associated with the fixed protocol.

According to some non-limiting embodiments or aspects, provided is a computer program product including at least one non-transitory computer-readable medium including program instructions that, when executed by at least one processor, cause the at least one processor to: obtain a fixed protocol including the following fixed protocol parameters according to which an injection system is configured to control delivery of at least one fluid to a patient in an injection: a flow rate of the at least one fluid to be delivered to the patient in at least one phase of the injection and a volume of the at least one fluid to be delivered to the patient in the at least one phase of the injection; provide, via a user interface of a computing device, a series of prompts, and receive, via the user interface of the computing device, a series of user responses in response to the series of prompts; and generate, based on the series of user responses and the fixed protocol, a smart protocol including the following smart protocol parameters according to which the injection system is configured to control delivery of the at least one fluid to the patient in the injection: a dosing factor and a dosing method, wherein the dosing factor is associated with a number of units of a contrast media to be delivered per a unit of weight, and wherein the dosing method is associated with one of a contrast media load and a contrast media delivery rate.

In some non-limiting embodiments or aspects, the program instructions, when executed by the at least one processor, further cause the at least one processor to: determine, based on the parameters of the fixed protocol, whether the fixed protocol is eligible to be converted to a smart protocol.

In some non-limiting embodiments or aspects, the computing device includes at least one of the following: the injection system, a user device, or any combination thereof.

In some non-limiting embodiments or aspects, the program instructions, when executed by the at least one processor, further cause the at least one processor to: provide, via the user interface of the computing device, in response to receiving a user response of the user responses, information associated with a change in the smart protocol generated by that user response.

In some non-limiting embodiments or aspects, the program instructions, when executed by the at least one processor, further cause the at least one processor to: receive, via the user interface of the computing device, user input associated with the smart protocol for the injection; calculate, based on the user input, values of the smart protocol parameters of the smart protocol; and control, according to the values of the smart protocol parameters of the smart protocol, the injection system to deliver the at least one fluid to the patient in the injection.

In some non-limiting embodiments or aspects, the user input includes at least one of the following: a weight of the patient, a lean body weight of the patient, a body surface area of the patient, or any combination thereof.

In some non-limiting embodiments or aspects, the series of prompts and the series of user responses thereto include a prompt and a corresponding user response thereto for at least one of the following: a concentration of the contrast media; an indication of whether the fixed protocol is adapted based on a size of the patient; an indication of whether to adapt the smart protocol based on the size of the patient; an indication of whether the fixed protocol is for computed tomography angiography (CTA); an indication of whether a duration of the fixed protocol is adjusted based on a duration of a CTA scan; a maximum flow rate of the at least one fluid associated with the fixed protocol; a minimum flow rate of the at least one fluid associated with the fixed protocol; a maximum volume of the at least one fluid associated with the fixed protocol; a minimum volume of the at least one fluid associated with the fixed protocol; an indication of whether the fixed protocol is associated with an average sized patient; a weight of the average sized patient; a lean body weight of the average sized patient; a target weight of the patient; a target lean body weight of the patient; an indication of a type of delivery method associated with the fixed protocol; an indication of whether a fixed duration for the smart protocol is acceptable; or any combination thereof.

In some non-limiting embodiments or aspects, the series of prompts and the series of user responses thereto include a prompt and a corresponding user response thereto for the indication of the type of delivery method associated with the fixed protocol, and wherein the indication of the type of delivery method associated with the fixed protocol includes a bolus tracking delivery method or a fixed delays delivery method.

In some non-limiting embodiments or aspects, the program instructions, when executed by the at least one processor, further cause the at least one processor to provide the series of prompts and receive the series of user responses in response to the series of prompts further by: providing a prompt for a concentration of the contrast media, and receiving a user response including the concentration of the contrast media; providing a prompt for an indication of whether the fixed protocol is adapted based on a size of the patient, and receiving a user response including the indication of whether the fixed protocol is adapted based on the size of the patient; in response to receiving a user response including an indication that the fixed protocol is adapted based on the size of the patient, providing a prompt for an indication of whether to adapt the smart protocol based on the size of the patient, and receiving a user response including the indication of whether to adapt the smart protocol based on a size of the patient; in response to (i) receiving a user response including an indication that the fixed protocol is not adapted based on the size of the patient or (ii) receiving the user response including the indication of whether to adapt the smart protocol based on the size of the patient, providing a prompt for an indication of whether the fixed protocol is for computed tomography angiography (CTA), and receiving a user response including the indication of whether the fixed protocol is for CTA; providing a prompt for an indication of a type of delivery method associated with the fixed protocol, and receiving a user response including the indication of the type of delivery method associated with the fixed protocol; in response to receiving the user response including the indication that the type of delivery method associated with the fixed protocol is a bolus tracking delivery method, providing a prompt for an indication of whether a duration of the fixed protocol is adjusted based on a duration of a CTA scan, and receiving a user response including the indication of whether a duration of the fixed protocol is adjusted based on the duration of the CTA scan; in response to (i) receiving a user response including an indication that the type of delivery method associated with the fixed protocol is a fixed delays delivery method or (ii) receiving a user response including the indication that the duration of the fixed protocol is adjusted based on the duration of the CTA scan, providing a prompt for a maximum flow rate of the at least one fluid associated with the fixed protocol, and receiving a user response including the maximum flow rate of the at least one fluid associated with the fixed protocol; in response to receiving the user response including the maximum flow rate of the at least one fluid associated with the fixed protocol, providing a prompt for a minimum flow rate of the at least one fluid associated with the fixed protocol, and receiving a user response including the minimum flow rate of the at least one fluid associated with the fixed protocol; in response to receiving (i) the user response including the indication to adapt the smart protocol based on the size of a patient and (ii) the user response including the indication that the fixed protocol is not for CTA or receiving (i) the user response including the minimum flow rate of the at least one fluid associated with the fixed protocol, or receiving (i) the user response including the indication that the fixed duration for the smart protocol is acceptable, providing a prompt for an indication of whether the fixed protocol is associated with an average sized patient, and receiving a user response including the indication of whether the fixed protocol is associated with the average sized patient; in response to receiving the user response including the indication that the fixed protocol is associated with the average sized patient, providing a prompt for at least one of a weight of the average sized patient and a lean body weight of the average sized patient, and receiving a user response including the at least one of the weight of the average sized patient and the lean body weight of the average sized patient; in response to receiving the user response including the indication that the fixed protocol is not associated with the average sized patient, providing a prompt for at least one of a target weight of the patient and a target lean body weight of the patient, and receiving a user response including the at least one of the target weight of the patient and the target lean body weight of the patient; in response to receiving (i) the user response including the at least one of the weight of the average sized patient and the lean body weight of the average sized patient or (ii) the user response including the at least one of the target weight of the patient and the target lean body weight of the patient, providing a prompt for a maximum volume of the at least one fluid associated with the fixed protocol, and receiving a user response including the maximum volume of the at least one fluid associated with the fixed protocol; in response to receiving the user response including the maximum volume of the at least one fluid associated with the fixed protocol, providing a prompt for a minimum volume of the at least one fluid associated with the fixed protocol, and receiving a user response including the minimum volume of at least one fluid associated with a fixed protocol; in response to receiving the user response including the indication that the fixed protocol is for CTA, providing a prompt for an indication of whether a fixed duration for the smart protocol is acceptable, and receiving a user response including the indication of whether the fixed duration for the smart protocol is acceptable; in response to receiving the user response including the indication that the fixed duration for the smart protocol is acceptable, providing the prompt for the maximum flow rate of the at least one fluid associated with the fixed protocol, and receiving the user response including the maximum flow rate of the at least one fluid associated with the fixed protocol; and in response to receiving the user response including the indication to not adapt the smart protocol based on the size of the patient, providing a prompt for the maximum volume of the at least one fluid associated with the fixed protocol, and receiving the user response including the maximum volume of the at least one fluid associated with the fixed protocol.

Further non-limiting embodiments or aspects are set forth in the following numbered clauses:

Clause 1. A system, comprising: at least one processor programmed and/or configured to: obtain a fixed protocol including the following fixed protocol parameters according to which an injection system is configured to control delivery of at least one fluid to a patient in an injection: a flow rate of the at least one fluid to be delivered to the patient in at least one phase of the injection and a volume of the at least one fluid to be delivered to the patient in the at least one phase of the injection; provide, via a user interface of a computing device, a series of prompts, and receive, via the user interface of the computing device, a series of user responses in response to the series of prompts; and generate, based on the series of user responses and the fixed protocol, a smart protocol including the following smart protocol parameters according to which the injection system is configured to control delivery of the at least one fluid to the patient in the injection: a dosing factor and a dosing method, wherein the dosing factor is associated with a number of units of a contrast media to be delivered per a unit of weight, and wherein the dosing method is associated with one of a contrast media load and a contrast media delivery rate.

Clause 2. The system of clause 1, wherein the at least one processor is further programmed and/or configured to: determine, based on the parameters of the fixed protocol, whether the fixed protocol is eligible to be converted to a smart protocol.

Clause 3. The system of clauses 1 or 2, wherein the computing device includes at least one of the following: the injection system, a user device, or any combination thereof.

Clause 4. The system of any of clauses 1-3, wherein the at least one processor is further programmed and/or configured to: provide, via the user interface of the computing device, in response to receiving a user response of the user responses, information associated with a change in the smart protocol generated by that user response.

Clause 5. The system of any of clauses 1-4, wherein the at least one processor is further programmed and/or configured to: receive, via the user interface of the computing device, user input associated with the smart protocol for the injection; calculate, based on the user input, values of the smart protocol parameters of the smart protocol; and control, according to the values of the smart protocol parameters of the smart protocol, the injection system to deliver the at least one fluid to the patient in the injection.

Clause 6. The system of any of clauses 1-5, wherein the user input includes at least one of the following: a weight of the patient, a lean body weight of the patient, a body surface area of the patient, or any combination thereof.

Clause 7. The system of any of clauses 1-6, wherein the series of prompts and the series of user responses thereto include a prompt and a corresponding user response thereto for at least one of the following: a concentration of the contrast media; an indication of whether the fixed protocol is adapted based on a size of the patient; an indication of whether to adapt the smart protocol based on the size of the patient; an indication of whether the fixed protocol is for computed tomography angiography (CTA); an indication of whether a duration of the fixed protocol is adjusted based on a duration of a CTA scan; a maximum flow rate of the at least one fluid associated with the fixed protocol, a minimum flow rate of the at least one fluid associated with the fixed protocol; a maximum volume of the at least one fluid associated with the fixed protocol; a minimum volume of the at least one fluid associated with the fixed protocol; an indication of whether the fixed protocol is associated with an average sized patient; a weight of the average sized patient; a lean body weight of the average sized patient; a target weight of the patient; a target lean body weight of the patient, an indication of a type of delivery method associated with the fixed protocol; an indication of whether a fixed duration for the smart protocol is acceptable; or any combination thereof.

Clause 8. The system of any of clauses 1-7, wherein the series of prompts and the series of user responses thereto include a prompt and a corresponding user response thereto for the indication of the type of delivery method associated with the fixed protocol, and wherein the indication of the type of delivery method associated with the fixed protocol includes a bolus tracking delivery method or a fixed delays delivery method.

Clause 9. The system of any of clauses 1-8, wherein the at least one processor is programmed and/or configured to provide the series of prompts, and receive the series of user responses in response to the series of prompts by: providing a prompt for a concentration of the contrast media, and receiving a user response including the concentration of the contrast media; providing a prompt for an indication of whether the fixed protocol is adapted based on a size of the patient, and receiving a user response including the indication of whether the fixed protocol is adapted based on the size of the patient; in response to receiving a user response including an indication that the fixed protocol is adapted based on the size of the patient, providing a prompt for an indication of whether to adapt the smart protocol based on the size of the patient, and receiving a user response including the indication of whether to adapt the smart protocol based on a size of the patient; in response to receiving (i) a user response including an indication that the fixed protocol is not adapted based on the size of the patient or (ii) receiving the user response including the indication of whether to adapt the smart protocol based on the size of the patient, providing a prompt for an indication of whether the fixed protocol is for computed tomography angiography (CTA), and receiving a user response including the indication of whether the fixed protocol is for CTA; providing a prompt for an indication of a type of delivery method associated with the fixed protocol, and receiving a user response including the indication of the type of delivery method associated with the fixed protocol; in response to receiving the user response including the indication that the type of delivery method associated with the fixed protocol is a bolus tracking delivery method, providing a prompt for an indication of whether a duration of the fixed protocol is adjusted based on a duration of a CTA scan, and receiving a user response including the indication of whether a duration of the fixed protocol is adjusted based on the duration of the CTA scan; in response to (i) receiving a user response including an indication that the type of delivery method associated with the fixed protocol is a fixed delays delivery method or (ii) receiving a user response including the indication that the duration of the fixed protocol is adjusted based on the duration of the CTA scan, providing a prompt for a maximum flow rate of the at least one fluid associated with the fixed protocol, and receiving a user response including the maximum flow rate of the at least one fluid associated with the fixed protocol; in response to receiving the user response including the maximum flow rate of the at least one fluid associated with the fixed protocol, providing a prompt for a minimum flow rate of the at least one fluid associated with the fixed protocol, and receiving a user response including the minimum flow rate of the at least one fluid associated with the fixed protocol; in response to receiving (i) the user response including the indication to adapt the smart protocol based on the size of a patient and (ii) the user response including the indication that the fixed protocol is not for CTA or receiving (i) the user response including the minimum flow rate of the at least one fluid associated with the fixed protocol, or receiving (i) the user response including the indication that the fixed duration for the smart protocol is acceptable, providing a prompt for an indication of whether the fixed protocol is associated with an average sized patient, and receiving a user response including the indication of whether the fixed protocol is associated with the average sized patient; in response to receiving the user response including the indication that the fixed protocol is associated with the average sized patient, providing a prompt for at least one of a weight of the average sized patient and a lean body weight of the average sized patient, and receiving a user response including the at least one of the weight of the average sized patient and the lean body weight of the average sized patient; in response to receiving the user response including the indication that the fixed protocol is not associated with the average sized patient, providing a prompt for at least one of a target weight of the patient and a target lean body weight of the patient, and receiving a user response including the at least one of the target weight of the patient and the target lean body weight of the patient; in response to receiving (i) the user response including the at least one of the weight of the average sized patient and the lean body weight of the average sized patient or (ii) the user response including the at least one of the target weight of the patient and the target lean body weight of the patient, providing a prompt for a maximum volume of the at least one fluid associated with the fixed protocol, and receiving a user response including the maximum volume of the at least one fluid associated with the fixed protocol; in response to receiving the user response including the maximum volume of the at least one fluid associated with the fixed protocol, providing a prompt for a minimum volume of the at least one fluid associated with the fixed protocol, and receiving a user response including the minimum volume of at least one fluid associated with a fixed protocol; in response to receiving the user response including the indication that the fixed protocol is for CTA, providing a prompt for an indication of whether a fixed duration for the smart protocol is acceptable, and receiving a user response including the indication of whether the fixed duration for the smart protocol is acceptable; in response to receiving the user response including the indication that the fixed duration for the smart protocol is acceptable, providing the prompt for the maximum flow rate of the at least one fluid associated with the fixed protocol, and receiving the user response including the maximum flow rate of the at least one fluid associated with the fixed protocol; and in response to receiving the user response including the indication to not adapt the smart protocol based on the size of the patient, providing a prompt for the maximum volume of the at least one fluid associated with the fixed protocol, and receiving the user response including the maximum volume of the at least one fluid associated with the fixed protocol.

Clause 10. The system of any of clauses 1-9, wherein the smart protocol includes an iodine dose/load (IDR)-based protocol or an iodine delivery rate (IDR)-based protocol.

Clause 11. A computer program product comprising at least one non-transitory computer-readable medium including program instructions that, when executed by at least one processor, cause the at least one processor to: obtain a fixed protocol including the following fixed protocol parameters according to which an injection system is configured to control delivery of at least one fluid to a patient in an injection: a flow rate of the at least one fluid to be delivered to the patient in at least one phase of the injection and a volume of the at least one fluid to be delivered to the patient in the at least one phase of the injection; provide, via a user interface of a computing device, a series of prompts, and receive, via the user interface of the computing device, a series of user responses in response to the series of prompts; and generate, based on the series of user responses and the fixed protocol, a smart protocol including the following smart protocol parameters according to which the injection system is configured to control delivery of the at least one fluid to the patient in the injection: a dosing factor and a dosing method, wherein the dosing factor is associated with a number of units of a contrast media to be delivered per a unit of weight, and wherein the dosing method is associated with one of a contrast media load and a contrast media delivery rate.

Clause 12. The computer program product of clause 11, wherein the program instructions, when executed by the at least one processor, further cause the at least one processor to: determine, based on the parameters of the fixed protocol, whether the fixed protocol is eligible to be converted to a smart protocol.

Clause 13. The computer program product of any of clauses 11 and 12, wherein the computing device includes at least one of the following: the injection system, a user device, or any combination thereof.

Clause 14. The computer program product of any of clauses 11-13, wherein the program instructions, when executed by the at least one processor, further cause the at least one processor to: provide, via the user interface of the computing device, in response to receiving a user response of the user responses, information associated with a change in the smart protocol generated by that user response.

Clause 15. The computer program product of any of clauses 11-14, wherein the program instructions, when executed by the at least one processor, further cause the at least one processor to: receive, via the user interface of the computing device, user input associated with the smart protocol for the injection; calculate, based on the user input, values of the smart protocol parameters of the smart protocol; and control, according to the values of the smart protocol parameters of the smart protocol, the injection system to deliver the at least one fluid to the patient in the injection.

Clause 16. The computer program product of any of clauses 11-15, wherein the user input includes at least one of the following: a weight of the patient, a lean body weight of the patient, a body surface area of the patient, or any combination thereof.

Clause 17. The computer program product of any of clauses 11-16, wherein the series of prompts and the series of user responses thereto include a prompt and a corresponding user response thereto for at least one of the following: a concentration of the contrast media; an indication of whether the fixed protocol is adapted based on a size of the patient; an indication of whether to adapt the smart protocol based on the size of the patient; an indication of whether the fixed protocol is for computed tomography angiography (CTA); an indication of whether a duration of the fixed protocol is adjusted based on a duration of a CTA scan; a maximum flow rate of the at least one fluid associated with the fixed protocol; a minimum flow rate of the at least one fluid associated with the fixed protocol; a maximum volume of the at least one fluid associated with the fixed protocol; a minimum volume of the at least one fluid associated with the fixed protocol; an indication of whether the fixed protocol is associated with an average sized patient; a weight of the average sized patient; a lean body weight of the average sized patient; a target weight of the patient; a target lean body weight of the patient; an indication of a type of delivery method associated with the fixed protocol; an indication of whether a fixed duration for the smart protocol is acceptable; or any combination thereof.

Clause 18. The computer program product of any of clauses 11-17, wherein the series of prompts and the series of user responses thereto include a prompt and a corresponding user response thereto for the indication of the type of delivery method associated with the fixed protocol, and wherein the indication of the type of delivery method associated with the fixed protocol includes a bolus tracking delivery method or a fixed delays delivery method.

Clause 19. The computer program product of any of clauses 11-18, wherein the program instructions, when executed by the at least one processor, further cause the at least one processor to provide the series of prompts and receive the series of user responses in response to the series of prompts further by: providing a prompt for a concentration of the contrast media, and receiving a user response including the concentration of the contrast media; providing a prompt for an indication of whether the fixed protocol is adapted based on a size of the patient, and receiving a user response including the indication of whether the fixed protocol is adapted based on the size of the patient; in response to receiving a user response including an indication that the fixed protocol is adapted based on the size of the patient, providing a prompt for an indication of whether to adapt the smart protocol based on the size of the patient, and receiving a user response including the indication of whether to adapt the smart protocol based on a size of the patient; in response to (i) receiving a user response including an indication that the fixed protocol is not adapted based on the size of the patient or (ii) receiving the user response including the indication of whether to adapt the smart protocol based on the size of the patient, providing a prompt for an indication of whether the fixed protocol is for computed tomography angiography (CTA), and receiving a user response including the indication of whether the fixed protocol is for CTA; providing a prompt for an indication of a type of delivery method associated with the fixed protocol, and receiving a user response including the indication of the type of delivery method associated with the fixed protocol; in response to receiving the user response including the indication that the type of delivery method associated with the fixed protocol is a bolus tracking delivery method, providing a prompt for an indication of whether a duration of the fixed protocol is adjusted based on a duration of a CTA scan, and receiving a user response including the indication of whether a duration of the fixed protocol is adjusted based on the duration of the CTA scan; in response to (i) receiving a user response including an indication that the type of delivery method associated with the fixed protocol is a fixed delays delivery method or (ii) receiving a user response including the indication that the duration of the fixed protocol is adjusted based on the duration of the CTA scan, providing a prompt for a maximum flow rate of the at least one fluid associated with the fixed protocol, and receiving a user response including the maximum flow rate of the at least one fluid associated with the fixed protocol; in response to receiving the user response including the maximum flow rate of the at least one fluid associated with the fixed protocol, providing a prompt for a minimum flow rate of the at least one fluid associated with the fixed protocol, and receiving a user response including the minimum flow rate of the at least one fluid associated with the fixed protocol; in response to receiving (i) the user response including the indication to adapt the smart protocol based on the size of a patient and (ii) the user response including the indication that the fixed protocol is not for CTA or receiving (i) the user response including the minimum flow rate of the at least one fluid associated with the fixed protocol, or receiving (i) the user response including the indication that the fixed duration for the smart protocol is acceptable, providing a prompt for an indication of whether the fixed protocol is associated with an average sized patient, and receiving a user response including the indication of whether the fixed protocol is associated with the average sized patient; in response to receiving the user response including the indication that the fixed protocol is associated with the average sized patient, providing a prompt for at least one of a weight of the average sized patient and a lean body weight of the average sized patient, and receiving a user response including the at least one of the weight of the average sized patient and the lean body weight of the average sized patient; in response to receiving the user response including the indication that the fixed protocol is not associated with the average sized patient, providing a prompt for at least one of a target weight of the patient and a target lean body weight of the patient, and receiving a user response including the at least one of the target weight of the patient and the target lean body weight of the patient; in response to receiving (i) the user response including the at least one of the weight of the average sized patient and the lean body weight of the average sized patient or (ii) the user response including the at least one of the target weight of the patient and the target lean body weight of the patient, providing a prompt for a maximum volume of the at least one fluid associated with the fixed protocol, and receiving a user response including the maximum volume of the at least one fluid associated with the fixed protocol; in response to receiving the user response including the maximum volume of the at least one fluid associated with the fixed protocol, providing a prompt for a minimum volume of the at least one fluid associated with the fixed protocol, and receiving a user response including the minimum volume of at least one fluid associated with a fixed protocol; in response to receiving the user response including the indication that the fixed protocol is for CTA, providing a prompt for an indication of whether a fixed duration for the smart protocol is acceptable, and receiving a user response including the indication of whether the fixed duration for the smart protocol is acceptable; in response to receiving the user response including the indication that the fixed duration for the smart protocol is acceptable, providing the prompt for the maximum flow rate of the at least one fluid associated with the fixed protocol, and receiving the user response including the maximum flow rate of the at least one fluid associated with the fixed protocol; and in response to receiving the user response including the indication to not adapt the smart protocol based on the size of the patient, providing a prompt for the maximum volume of the at least one fluid associated with the fixed protocol, and receiving the user response including the maximum volume of the at least one fluid associated with the fixed protocol.

Clause 20. A computer-implemented method, comprising: obtaining, with at least one processor, a fixed protocol including the following fixed protocol parameters according to which an injection system is configured to control delivery of at least one fluid to a patient in an injection: a flow rate of the at least one fluid to be delivered to the patient in at least one phase of the injection and a volume of the at least one fluid to be delivered to the patient in the at least one phase of the injection; providing, with the at least one processor, via a user interface of a computing device, a series of prompts, and receiving, with the at least one processor, via the user interface of the computing device, a series of user responses in response to the series of prompts; and generate, with the at least one processor, based on the series of user responses and the fixed protocol, a smart protocol including the following smart protocol parameters according to which the injection system is configured to control delivery of the at least one fluid to the patient in the injection: a dosing factor and a dosing method, wherein the dosing factor is associated with a number of units of a contrast media to be delivered per a unit of weight, and wherein the dosing method is associated with one of a contrast media load and a contrast media delivery rate.

Clause 21. The computer-implemented method of clause 20, further comprising: determining, with the at least one processor, based on the parameters of the fixed protocol, whether the fixed protocol is eligible to be converted to a smart protocol.

Clause 22. The computer-implemented method of clauses 20 or 21, wherein the computing device includes at least one of the following: the injection system, a user device, or any combination thereof.

Clause 23. The computer-implemented method of any of clauses 20-22, further comprising: providing, with the at least one processor, via the user interface of the computing device, in response to receiving a user response of the user responses, information associated with a change in the smart protocol generated by that user response.

Clause 24. The computer-implemented method of any of clauses 20-23, further comprising: receiving, with the at least one processor, via the user interface of the computing device, user input associated with the smart protocol for the injection; calculating, with the at least one processor, based on the user input, values of the smart protocol parameters of the smart protocol; and controlling, with the at least one processor, according to the values of the smart protocol parameters of the smart protocol, the injection system to deliver the at least one fluid to the patient in the injection.

Clause 25. The computer-implemented method of any of clauses 20-24, wherein the user input includes at least one of the following: a weight of the patient, a lean body weight of the patient, a body surface area of the patient, or any combination thereof.

Clause 26. The computer-implemented method of any of clauses 20-25, wherein the series of prompts and the series of user responses thereto include a prompt and a corresponding user response thereto for at least one of the following: a concentration of the contrast media; an indication of whether the fixed protocol is adapted based on a size of the patient; an indication of whether to adapt the smart protocol based on the size of the patient; an indication of whether the fixed protocol is for computed tomography angiography (CTA); an indication of whether a duration of the fixed protocol is adjusted based on a duration of a CTA scan; a maximum flow rate of the at least one fluid associated with the fixed protocol, a minimum flow rate of the at least one fluid associated with the fixed protocol; a maximum volume of the at least one fluid associated with the fixed protocol; a minimum volume of the at least one fluid associated with the fixed protocol; an indication of whether the fixed protocol is associated with an average sized patient; a weight of the average sized patient; a lean body weight of the average sized patient; a target weight of the patient; a target lean body weight of the patient, an indication of a type of delivery method associated with the fixed protocol; an indication of whether a fixed duration for the smart protocol is acceptable; or any combination thereof.

Clause 27. The computer-implemented method of any of clauses 20-26, wherein the series of prompts and the series of user responses thereto include a prompt and a corresponding user response thereto for the indication of the type of delivery method associated with the fixed protocol, and wherein the indication of the type of delivery method associated with the fixed protocol includes a bolus tracking delivery method or a fixed delays delivery method.

Clause 28. The computer-implemented method of any of clauses 20-27, wherein providing, with the at least one processor, the series of prompts, and receiving, with the at least one processor, the series of user responses in response to the series of prompts further includes: providing a prompt for a concentration of the contrast media, and receiving a user response including the concentration of the contrast media; providing a prompt for an indication of whether the fixed protocol is adapted based on a size of the patient, and receiving a user response including the indication of whether the fixed protocol is adapted based on the size of the patient; in response to receiving a user response including an indication that the fixed protocol is adapted based on the size of the patient, providing a prompt for an indication of whether to adapt the smart protocol based on the size of the patient, and receiving a user response including the indication of whether to adapt the smart protocol based on a size of the patient; in response to receiving (i) a user response including an indication that the fixed protocol is not adapted based on the size of the patient or (ii) receiving the user response including the indication of whether to adapt the smart protocol based on the size of the patient, providing a prompt for an indication of whether the fixed protocol is for computed tomography angiography (CTA), and receiving a user response including the indication of whether the fixed protocol is for CTA; providing a prompt for an indication of a type of delivery method associated with the fixed protocol, and receiving a user response including the indication of the type of delivery method associated with the fixed protocol; in response to receiving the user response including the indication that the type of delivery method associated with the fixed protocol is a bolus tracking delivery method, providing a prompt for an indication of whether a duration of the fixed protocol is adjusted based on a duration of a CTA scan, and receiving a user response including the indication of whether a duration of the fixed protocol is adjusted based on the duration of the CTA scan; in response to (i) receiving a user response including an indication that the type of delivery method associated with the fixed protocol is a fixed delays delivery method or (ii) receiving a user response including the indication that the duration of the fixed protocol is adjusted based on the duration of the CTA scan, providing a prompt for a maximum flow rate of the at least one fluid associated with the fixed protocol, and receiving a user response including the maximum flow rate of the at least one fluid associated with the fixed protocol; in response to receiving the user response including the maximum flow rate of the at least one fluid associated with the fixed protocol, providing a prompt for a minimum flow rate of the at least one fluid associated with the fixed protocol, and receiving a user response including the minimum flow rate of the at least one fluid associated with the fixed protocol; in response to receiving (i) the user response including the indication to adapt the smart protocol based on the size of a patient and (ii) the user response including the indication that the fixed protocol is not for CTA or receiving (i) the user response including the minimum flow rate of the at least one fluid associated with the fixed protocol, or receiving (i) the user response including the indication that the fixed duration for the smart protocol is acceptable, providing a prompt for an indication of whether the fixed protocol is associated with an average sized patient, and receiving a user response including the indication of whether the fixed protocol is associated with the average sized patient; in response to receiving the user response including the indication that the fixed protocol is associated with the average sized patient, providing a prompt for at least one of a weight of the average sized patient and a lean body weight of the average sized patient, and receiving a user response including the at least one of the weight of the average sized patient and the lean body weight of the average sized patient; in response to receiving the user response including the indication that the fixed protocol is not associated with the average sized patient, providing a prompt for at least one of a target weight of the patient and a target lean body weight of the patient, and receiving a user response including the at least one of the target weight of the patient and the target lean body weight of the patient; in response to receiving (i) the user response including the at least one of the weight of the average sized patient and the lean body weight of the average sized patient or (ii) the user response including the at least one of the target weight of the patient and the target lean body weight of the patient, providing a prompt for a maximum volume of the at least one fluid associated with the fixed protocol, and receiving a user response including the maximum volume of the at least one fluid associated with the fixed protocol; in response to receiving the user response including the maximum volume of the at least one fluid associated with the fixed protocol, providing a prompt for a minimum volume of the at least one fluid associated with the fixed protocol, and receiving a user response including the minimum volume of at least one fluid associated with a fixed protocol; in response to receiving the user response including the indication that the fixed protocol is for CTA, providing a prompt for an indication of whether a fixed duration for the smart protocol is acceptable, and receiving a user response including the indication of whether the fixed duration for the smart protocol is acceptable; in response to receiving the user response including the indication that the fixed duration for the smart protocol is acceptable, providing the prompt for the maximum flow rate of the at least one fluid associated with the fixed protocol, and receiving the user response including the maximum flow rate of the at least one fluid associated with the fixed protocol; and in response to receiving the user response including the indication to not adapt the smart protocol based on the size of the patient, providing a prompt for the maximum volume of the at least one fluid associated with the fixed protocol, and receiving the user response including the maximum volume of the at least one fluid associated with the fixed protocol.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of limits. As used in the specification and the claims, the singular form of "a," "an," and "the" include plural referents unless the context clearly dictates otherwise.

BRIEF DESCRIPTION OF THE DRAWINGS

Additional advantages and details are explained in greater detail below with reference to the exemplary embodiments that are illustrated in the accompanying schematic figures, in which.

DETAILED DESCRIPTION

Figure 1:
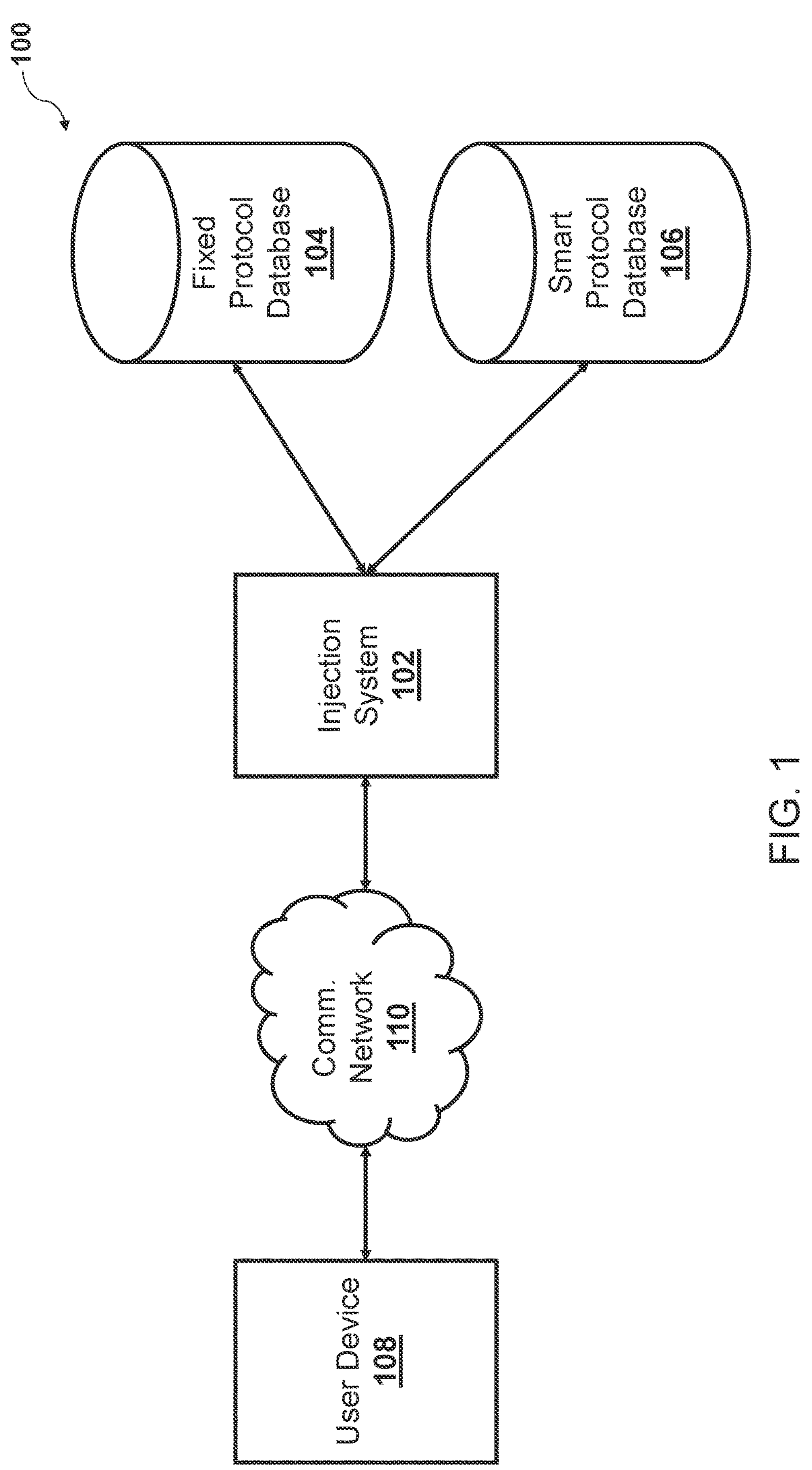
FIG. 1 is a diagram of non-limiting embodiments or aspects of an environment in which systems, devices, products, apparatus, and/or methods, described herein, may be implemented.

It is to be understood that the present disclosure may assume various alternative variations and step sequences, except where expressly specified to the contrary. It is also to be understood that the specific devices and processes illustrated in the attached drawings, and described in the following specification, are simply exemplary and non-limiting embodiments or aspects. Hence, specific dimensions and other physical characteristics related to the embodiments or aspects disclosed herein are not to be considered as limiting.

No aspect, component, element, structure, act, step, function, instruction, and/or the like used herein should be construed as critical or essential unless explicitly described as such. Also, as used herein, the articles "a" and "an" are intended to include one or more items and may be used interchangeably with "one or more" and "at least one." Furthermore, as used herein, the term "set" is intended to include one or more items (e.g., related items, unrelated items, a combination of related and unrelated items, etc.) and may be used interchangeably with "one or more" or "at least one." Where only one item is intended, the term "one" or similar language is used. Also, as used herein, the terms "has," "have," "having," or the like are intended to be open-ended terms. Further, the phrase "based on" is intended to mean "based at least partially on" unless explicitly stated otherwise.

As used herein, the term "communication" may refer to the reception, receipt, transmission, transfer, provision, and/or the like, of data (e.g., information, signals, messages, instructions, commands, and/or the like). For one unit (e.g., a device, a system, a component of a device or system, combinations thereof, and/or the like) to be in communication with another unit means that the one unit is able to directly or indirectly receive information from and/or transmit information to the other unit. This may refer to a direct or indirect connection (e.g., a direct communication connection, an indirect communication connection, and/or the like) that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively transmit information to the second unit. As another example, a first unit may be in communication with a second unit if at least one intermediary unit processes information received from the first unit and communicates the processed information to the second unit.

It will be apparent that systems and/or methods, described herein, can be implemented in different forms of hardware, software, or a combination of hardware and software. The actual specialized control hardware or software code used to implement these systems and/or methods is not limiting of the implementations. Thus, the operation and behavior of the systems and/or methods are described herein without reference to specific software code, it being understood that software and hardware can be designed to implement the systems and/or methods based on the description herein.

Some non-limiting embodiments or aspects may be described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

As used herein, the term "computing device" may refer to one or more electronic devices configured to process data. A computing device may, in some examples, include the necessary components to receive, process, and output data, such as a processor, a display, a memory, an input device, a network interface, and/or the like. A computing device may be a mobile device. As an example, a mobile device may include a cellular phone (e.g., a smartphone or standard cellular phone), a portable computer, a wearable device (e.g., watches, glasses, lenses, clothing, and/or the like), a PDA, and/or other like devices. A computing device may also be a desktop computer or other form of non-mobile computer.

As used herein, the term "mobile device" may refer to one or more portable electronic devices configured to communicate with one or more networks. As an example, a mobile device may include a cellular phone (e.g., a smartphone or standard cellular phone), a portable computer (e.g., a tablet computer, a laptop computer, etc.), a wearable device (e.g., a watch, pair of glasses, lens, clothing, and/or the like), a personal digital assistant (PDA), and/or other like devices. The terms "client device" and "user device," as used herein, refer to any electronic device that is configured to communicate with one or more servers or remote devices and/or systems. A client device or user device may include a mobile device, a network-enabled appliance (e.g., a network-enabled television, refrigerator, thermostat, and/or the like), a computer, an injection system, and/or any other device or system capable of communicating with a network.

As used herein, the term "server" and/or "processor" may refer to or include one or more computing devices that are operated by or facilitate communication and processing for multiple parties in a network environment, such as the Internet, although it will be appreciated that communication may be facilitated over one or more public or private network environments and that various other arrangements are possible. Further, multiple computing devices (e.g., servers, injectors, mobile devices, etc.) directly or indirectly communicating in the network environment may constitute a "system." Reference to "a server" or "a processor," as used herein, may refer to a previously-recited server and/or processor that is recited as performing a previous step or function, a different server and/or processor, and/or a combination of servers and/or processors. For example, as used in the specification and the claims, a first server and/or a first processor that is recited as performing a first step or function may refer to the same or different server and/or a processor recited as performing a second step or function.

As used herein, the term "user interface" or "graphical user interface" refers to a generated display, such as one or more graphical user interfaces (GUIs) with which a user may interact, either directly or indirectly (e.g., through a keyboard, mouse, touchscreen, etc.).

Referring now to FIG. 1, FIG. 1 is a diagram of an example environment 100 in which systems, devices, methods, and/or products described herein, may be implemented. As shown in FIG. 1, environment 100 may include injection system 102, fixed protocol database 104, smart protocol database 106, user device 108, and/or communication network 110.

Injection system 102 may include one or more devices capable of receiving data and/or information from and/or communicating data and/or information to user device 108 (e.g., via communication network 110, etc.). For example, injection system 102 may include a computing device, such as a one or more computers, portable computers (e.g., tablet computers, etc.), mobile devices (e.g., cellular phones, smartphones, wearable devices, such as watches, glasses, lenses, and/or clothing, PDAs, and/or the like), a server, a group of servers, and/or other like devices.

Injection system 102 may be in communication with a data storage device, such as fixed protocol database 104, smart protocol database 106, and/or the like, which may be local or remote to injection system 102. Injection system 102 may be capable of receiving data and/or information from, storing data and/or information in, communicating data and/or information to, or searching data and/or information stored in the data storage device.

Fixed protocol database 104 may store one or more fixed protocols including fixed protocol parameters according to which injection system 102 is configured to control delivery of at least one fluid to a patient in an injection.

Smart protocol database 106 may store one or more smart protocols including smart protocol parameters according to which injection system 102 is configured to control delivery of at least one fluid to a patient in an injection.

User device 108 may include one or more devices capable of receiving data and/or information from and/or communicating data and/or information to injection system 102 (e.g., via communication network 110, etc.). For example, user device 108 may include a computing device, such as a one or more computers, portable computers (e.g., tablet computers, etc.), mobile devices (e.g., cellular phones, smartphones, wearable devices, such as watches, glasses, lenses, and/or clothing, PDAs, and/or the like, etc.), a server, a group of servers, and/or other like devices.

In some non-limiting embodiments or aspects, a fixed protocol includes (and/or consists of) a flow rate (e.g., a fixed flow rate, etc.) of at least one fluid to be delivered to a patient in at least one phase of an injection and a volume (e.g., a fixed volume, etc.) of the at least one fluid to be delivered to the patient in the at least one phase of the injection. For example, a fixed protocol may include (and/or consist of) a first fixed flow rate and a first fixed volume of a first fluid to be delivered to a patient in a first phase of an injection and a second fixed flow rate and a second fixed volume of a second fluid to be delivered to the patient in a second phase of the injection.

In some non-limiting embodiments or aspects, a smart protocol includes an iodine dose/load (IDL)-based protocol or algorithm or an iodine delivery rate (IDR)-based protocol or algorithm. A smart protocol may include a flow rate of at least one fluid to be delivered to a patient in at least one phase of an injection, a volume of the at least one fluid to be delivered to the patient in the at least one phase of the injection, an iodine load, an iodine delivery rate, and/or a weight-based parameter. For example, a smart protocol can include a protocol for the delivery of a fluid volume over time where the fluid volume includes at least a volumetric amount of a first fluid (e.g., Fluid A), such as contrast agent, delivered at a flow rate that may vary over time and may be zero at certain times, and a volumetric amount of a second fluid (e.g., Fluid B), such as saline, which also may be delivered at a flow rate that may vary over time and may be zero at certain times.

Injection system 102 may be configured to inject, deliver, or administer contrast fluid including a contrast agent to a patient, and in some non-limiting embodiments or aspects, to inject or administer saline or other fluid to a patient before, during, or after administration of contrast fluid. Exemplary injection systems or injectors are those that are disclosed in: U.S. patent application Ser. No. 09/715,330, filed on Nov. 17, 2000, issued as U.S. Pat. No. 6,643,537; U.S. patent application Ser. No. 09/982,518, filed on Oct. 18, 2001, issued as U.S. Pat. No. 7,094,216; U.S. patent application Ser. No. 10/825,866, filed on Apr. 16, 2004, issued as U.S. Pat. No. 7,556,619; U.S. patent application Ser. No. 12/437,011, filed on May 7, 2009, issued as U.S. Pat. No. 8,337,456; U.S. patent application Ser. No. 12/476,513, filed on Jun. 2, 2009, issued as U.S. Pat. No. 8,147,464; and U.S. patent application Ser. No. 11/004,670, filed on Dec. 3, 2004, issued as U.S. Pat. No. 8,540,698, the disclosures of each of which are incorporated herein by reference in their entireties. In some non-limiting embodiments or aspects, injection system 102 may include the MEDRAD® Centargo CT Injection System. In other non-limiting embodiments or aspects, injection system 102 may include the MEDRAD® Stellant CT Injection System or the MEDRAD® Stellant FLEX CT Injection System, each of which offered by Bayer with the Certegra® Workstation.

Communication network 110 may include one or more wired and/or wireless networks. For example, communication network 110 may include a cellular network (e.g., a long-term evolution (LTE) network, a third generation (3G) network, a fourth generation (4G) network, a fifth generation (5G) network, a code division multiple access (CDMA) network, etc.), a public land mobile network (PLMN), a local area network (LAN), a wide area network (WAN), a metropolitan area network (MAN), a telephone network (e.g., the public switched telephone network (PSTN)), a private network, an ad hoc network, an intranet, the Internet, a fiber optic-based network, a cloud computing network, a short range wireless communication network (e.g., a Bluetooth network, a near field communication (NFC) network, etc.) and/or the like, and/or a combination of these or other types of networks.

The number and arrangement of devices and systems shown in FIG. 1 is provided as an example. There may be additional devices and/or systems, fewer devices and/or systems, different devices and/or systems, or differently arranged devices and/or systems than those shown in FIG. 1. Furthermore, two or more devices and/or systems shown in FIG. 1 may be implemented within a single device and/or system, or a single device and/or system shown in FIG. 1 may be implemented as multiple, distributed devices and/or systems. Additionally or alternatively, a set of devices and/or systems (e.g., one or more devices or systems) of environment 100 may perform one or more functions described as being performed by another set of devices and/or systems of environment 100.

Figure 2:
FIG. 2 is a diagram of non-limiting embodiments or aspects of components of one or more devices and/or one or more systems of FIG. 1.
Figure 2:
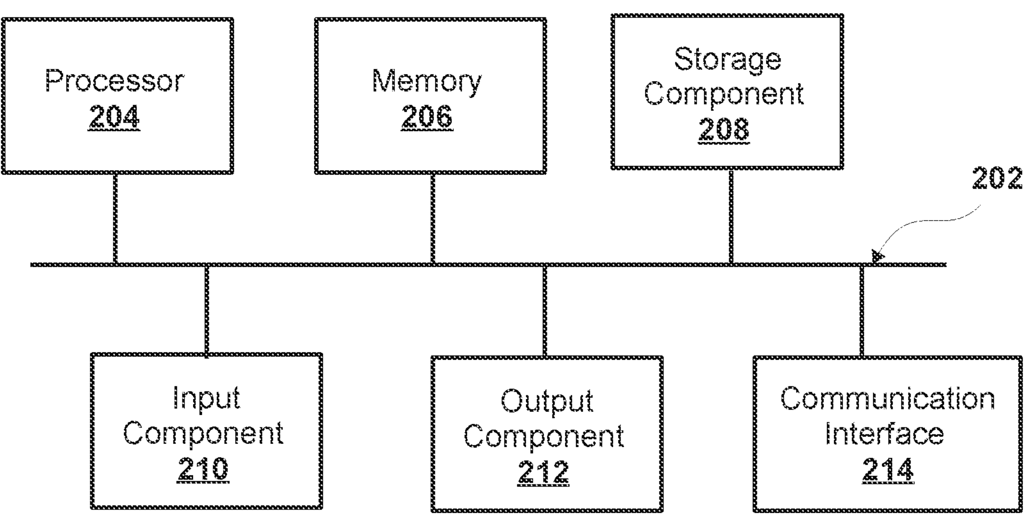

Referring now to FIG. 2, FIG. 2 is a diagram of example components of a device 200. Device 200 may correspond to one or more devices of injection system 102 and/or user device 108 (e.g., one or more devices of a system of user device 108, etc.). In some non-limiting embodiments or aspects, one or more devices of injection system 102 and/or user device 108 (e.g., one or more devices of a system of user device 108, etc.) may include at least one device 200 and/or at least one component of device 200. As shown in FIG. 2, device 200 may include bus 202, processor 204, memory 206, storage component 208, input component 210, output component 212, and communication interface 214.

Bus 202 may include a component that permits communication among the components of device 200. In some non-limiting embodiments or aspects, processor 204 may be implemented in hardware, software, or a combination of hardware and software. For example, processor 204 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 206 may include random access memory (RAM), read-only memory (ROM), and/or another type of dynamic or static storage device (e.g., flash memory, magnetic memory, optical memory, etc.) that stores information and/or instructions for use by processor 204.

Storage component 208 may store information and/or software related to the operation and use of device 200. For example, storage component 208 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of non-transitory computer-readable medium, along with a corresponding drive.

Input component 210 may include a component that permits device 200 to receive information, such as via user input (e.g., a touch screen display, a keyboard, a keypad, a mouse, a button, a switch, a microphone, etc.). Additionally or alternatively, input component 210 may include a sensor for sensing information (e.g., a global positioning system (GPS) component, an accelerometer, a gyroscope, an actuator, etc.). Output component 212 may include a component that provides output information from device 200 (e.g., a display, a speaker, one or more light-emitting diodes (LEDs), etc.).

Communication interface 214 may include a transceiver-like component (e.g., a transceiver, a separate receiver and transmitter, etc.) that enables device 200 to communicate with other devices, such as via a wired connection, a wireless connection, or a combination of wired and wireless connections. Communication interface 214 may permit device 200 to receive information from another device and/or provide information to another device. For example, communication interface 214 may include an Ethernet interface, an optical interface, a coaxial interface, an infrared interface, a radio frequency (RF) interface, a universal serial bus (USB) interface, a WiFi® interface, a cellular network interface, and/or the like.

Device 200 may perform one or more processes described herein. Device 200 may perform these processes based on processor 204 (e.g., a central processing unit (CPU), a graphics processing unit (GPU), etc.) executing software instructions stored by a computer-readable medium, such as memory 206 and/or storage component 208. A computer-readable medium (e.g., a non-transitory computer-readable medium) is defined herein as a non-transitory memory device. A non-transitory memory device includes memory space located inside of a single physical storage device or memory space spread across multiple physical storage devices.

Software instructions may be read into memory 206 and/or storage component 208 from another computer-readable medium or from another device via communication interface 214. When executed, software instructions stored in memory 206 and/or storage component 208 may cause processor 204 to perform one or more processes described herein. Additionally or alternatively, hardwired circuitry may be used in place of or in combination with software instructions to perform one or more processes described herein. Thus, embodiments or aspects described herein are not limited to any specific combination of hardware circuitry and software.

Memory 206 and/or storage component 208 may include data storage or one or more data structures (e.g., a database, etc.). Device 200 may be capable of receiving information from, storing information in, communicating information to, or searching information stored in the data storage or one or more data structures in memory 206 and/or storage component 208.

The number and arrangement of components shown in FIG. 2 are provided as an example. In some non-limiting embodiments or aspects, device 200 may include additional components, fewer components, different components, or differently arranged components than those shown in FIG. 2. Additionally or alternatively, a set of components (e.g., one or more components) of device 200 may perform one or more functions described as being performed by another set of components of device 200.

Figure 3:
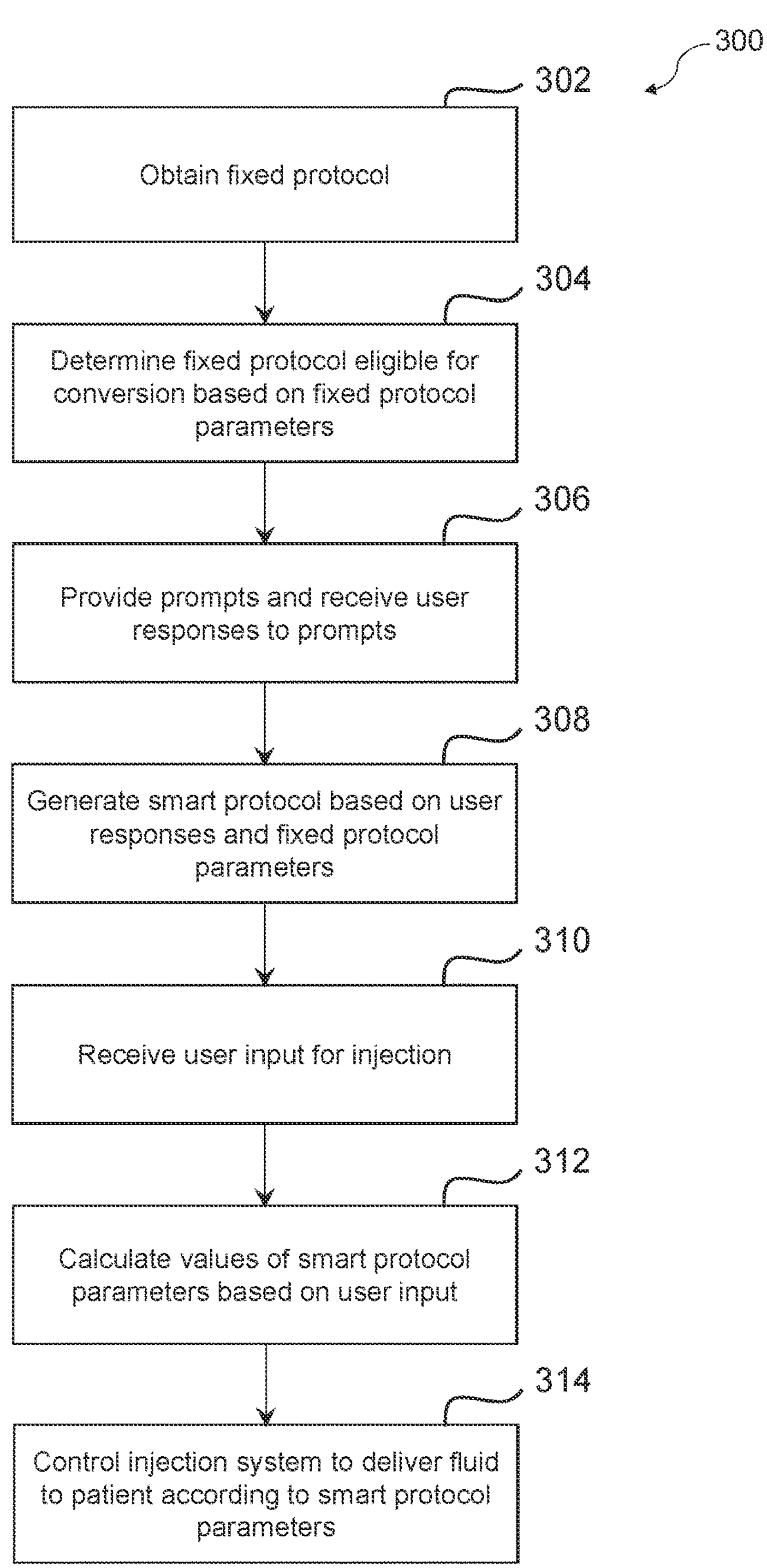
FIG. 3 is a flowchart of non-limiting embodiments or aspects of a process for protocol conversion.

Referring now to FIG. 3, FIG. 3 is a flowchart of non-limiting embodiments or aspects of a process 300 for protocol conversion. In some non-limiting embodiments or aspects, one or more of the steps of process 300 may be performed (e.g., completely, partially, etc.) by injection system 102. In some non-limiting embodiments or aspects, one or more of the steps of process 300 may be performed (e.g., completely, partially, etc.) by another device or a group of devices separate from or including injection system 102, such as user device 108.

As shown in FIG. 3, at step 302, process 300 includes obtaining a fixed protocol. For example, injection system 102 may obtain a fixed protocol. As an example, injection system 102 may obtain a fixed protocol including the following fixed protocol parameters according to which an injection system is configured to control delivery of at least one fluid to a patient in an injection: a flow rate of the at least one fluid to be delivered to the patient in at least one phase of the injection and a volume of the at least one fluid to be delivered to the patient in the at least one phase of the injection.

As shown in FIG. 3, at step 304, process 300 includes determining that a fixed protocol is eligible for conversion based on parameters of the fixed protocol. For example, injection system 102 may determine that a fixed protocol is eligible for conversion based on parameters of the fixed protocol. As an example, injection system 102 may determine, based on the parameters of the fixed protocol, whether the fixed protocol is eligible to be converted to a smart protocol.

In some non-limiting embodiments or aspects, injection system 102 may only enable a conversion of simple protocols that are bi-phasic (e.g., contrast followed by saline flush, etc.) so that an end result is more certain to be clear and understandable to a user. For example, injection system 102 may require a fixed protocol to include a diagnostic phase including a single contrast phase and followed by a saline phase having the same flow rate and only one diagnostic injection step in order for the fixed protocol to be eligible to be converted to a smart protocol. In such an example, although allowing a single contrast phase is a fairly simple extension, injection system 102 may ensure that there is no reason to believe that leaving contrast in the line for subsequent injections is not part of the users need (or reduce the volume to account for the undelivered contrast in the line), and for this reason a saline flush phase may be required for the protocol to be eligible to be converted to a smart protocol. In such an example, the presence of test injection (TI) in a fixed protocol may be allowed to cause a TI to be added to a smart protocol and questions about TI method to be asked.

As shown in FIG. 3, at step 306, process 300 includes providing prompts and receiving user responses to the prompts. For example, injection system 102 may provide prompts and receive user responses to the prompts. As an example, injection system 102 may provide, via a user interface of a computing device (e.g., a touch screen display, etc.), a series of prompts, and receive, via the user interface of the computing device, a series of user responses in response to the series of prompts.

In some non-limiting embodiments or aspects, injection system 102 may provide, via the user interface of the computing device, in response to receiving a user response of the user responses, information associated with a change in the smart protocol generated by that user response. For example, injection system 102 may provide (e.g., in smaller text below the user response) information intended to help inform the user about the consequences of the user response provided. As an example, the information may contain calculated values and/or varying text that depends on the user response provided and may only be displayed after a user response to a prompt is received.

In some non-limiting embodiments or aspects, injection system 102 may provide a prompt in combination with guidance intended to help the user understand the question better or to provide hints.

In some non-limiting embodiments or aspects, the series of prompts and the series of user responses thereto include a prompt and a corresponding user response thereto for at least one of the following: a concentration of the contrast media; an indication of whether the fixed protocol is adapted based on a size of the patient; an indication of whether to adapt the smart protocol based on the size of the patient; an indication of whether the fixed protocol is for computed tomography angiography (CTA); an indication of whether a duration of the fixed protocol is adjusted based on a duration of a CTA scan; a maximum flow rate of the at least one fluid associated with the fixed protocol, a minimum flow rate of the at least one fluid associated with the fixed protocol; a maximum volume of the at least one fluid associated with the fixed protocol; a minimum volume of the at least one fluid associated with the fixed protocol; an indication of whether the fixed protocol is associated with an average sized patient; a weight of the average sized patient; a lean body weight of the average sized patient; a target weight of the patient; a target lean body weight of the patient, an indication of a type of delivery method associated with the fixed protocol; an indication of whether a fixed duration for the smart protocol is acceptable; or any combination thereof.

Further details regarding step 306 of process 300 are provided below with regard to FIGS. 4A-4D.

As shown in FIG. 3, at step 308, process 300 includes generating a smart protocol based on user responses and fixed protocol parameters. For example, injection system 102 may generate a smart protocol based on user responses and fixed protocol parameters. As an example, injection system 102 may generate, based on the user responses and the fixed protocol, a smart protocol including the following smart protocol parameters according to which the injection system is configured to control delivery of the at least one fluid to the patient in the injection: a dosing factor and a dosing method, wherein the dosing factor is associated with a number of units of a contrast media to be delivered per a unit of weight, and wherein the dosing method is associated with one of a contrast media load and a contrast media delivery rate. In such an example, injection system 102 may store the smart protocol including the smart protocol parameters in smart protocol database 106. For example, the smart protocol including the smart protocol parameters may be stored in smart protocol database 106 during an administrative time (e.g., outside of an exam time, etc.).

Figure 6A:
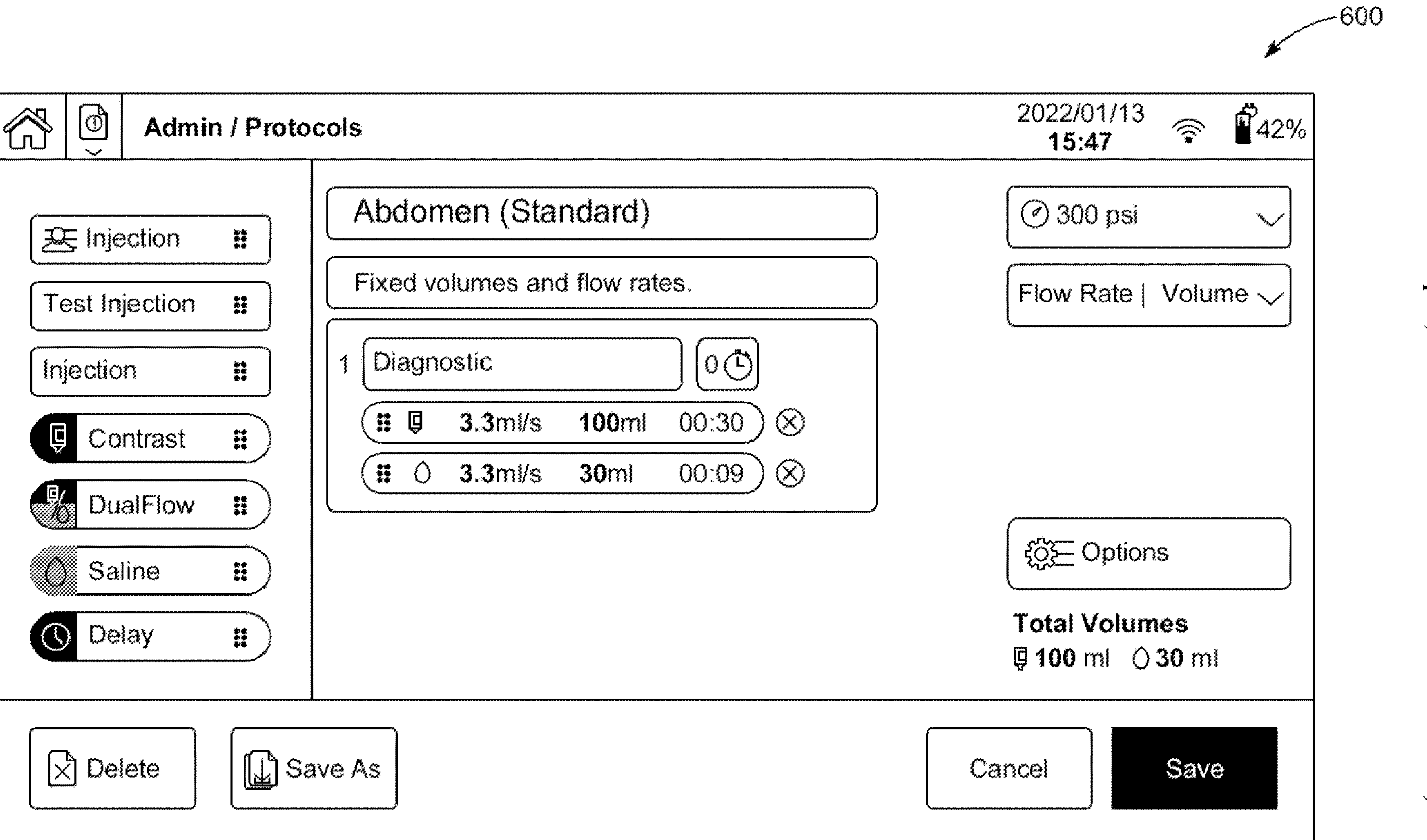
FIGS. 6A-6Q are screenshots of non-limiting embodiments or aspects of a user interface of a process for protocol conversion.
Figure 6B:
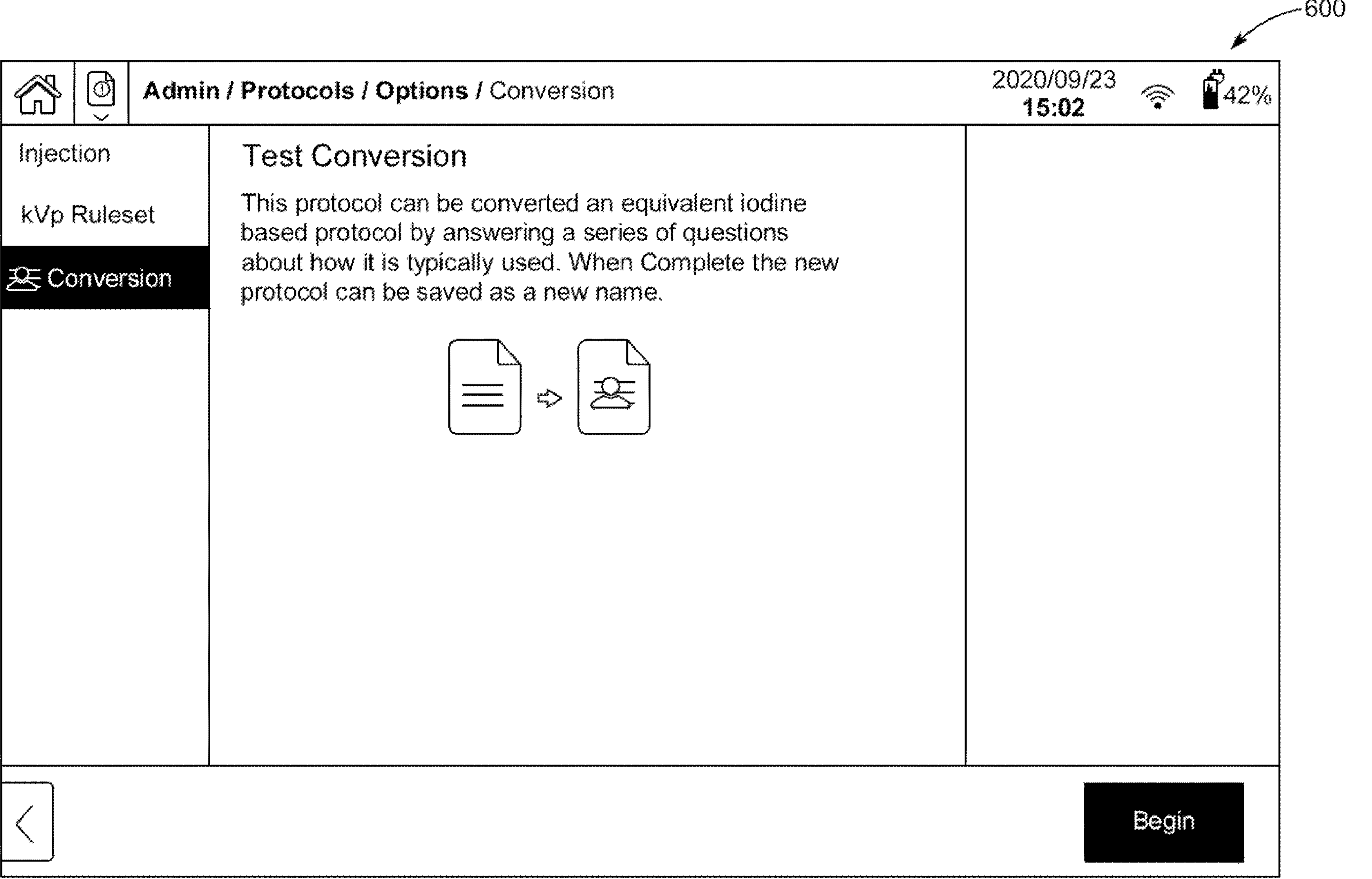
Figure 6C:
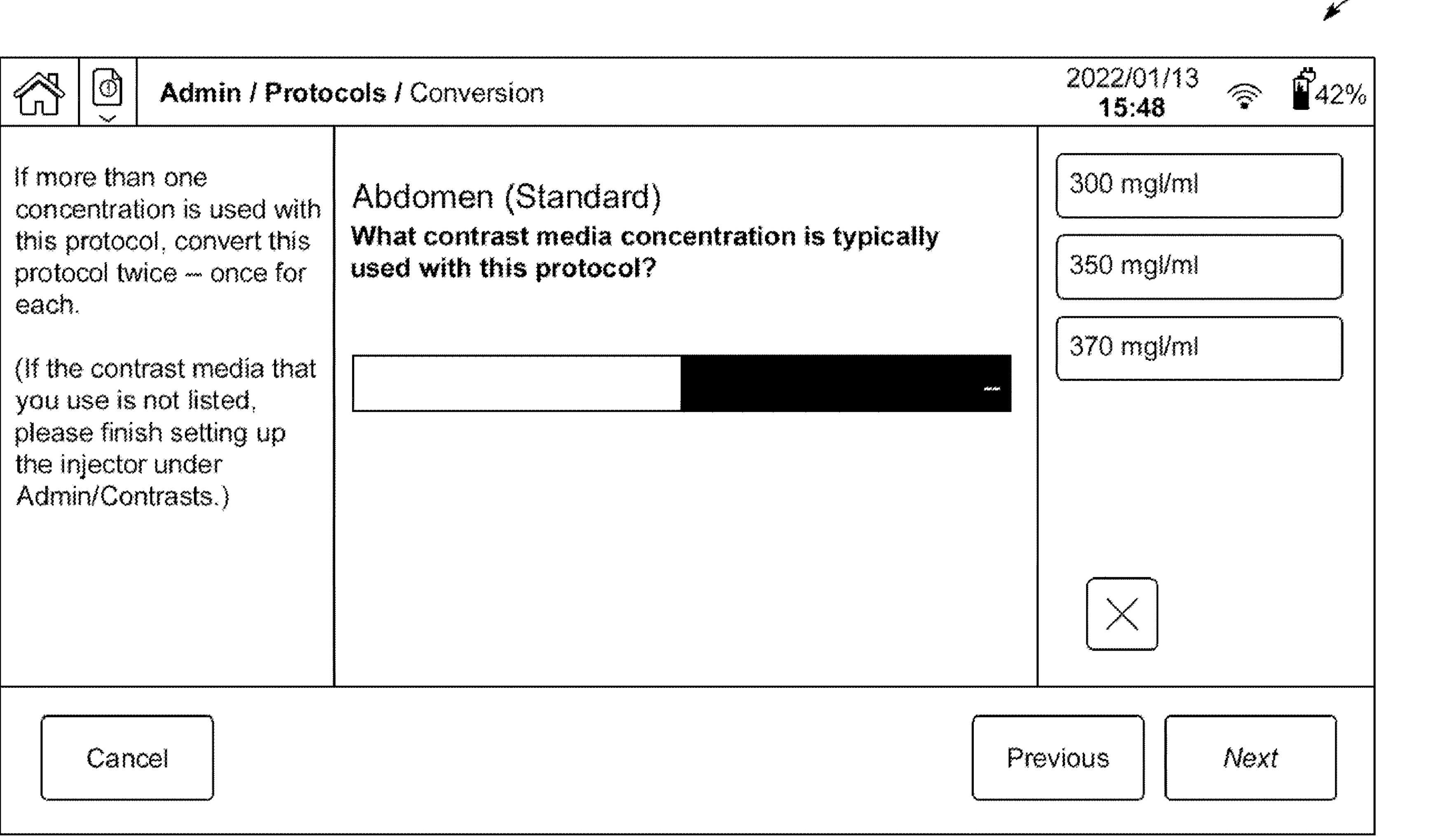
Figure 6D:
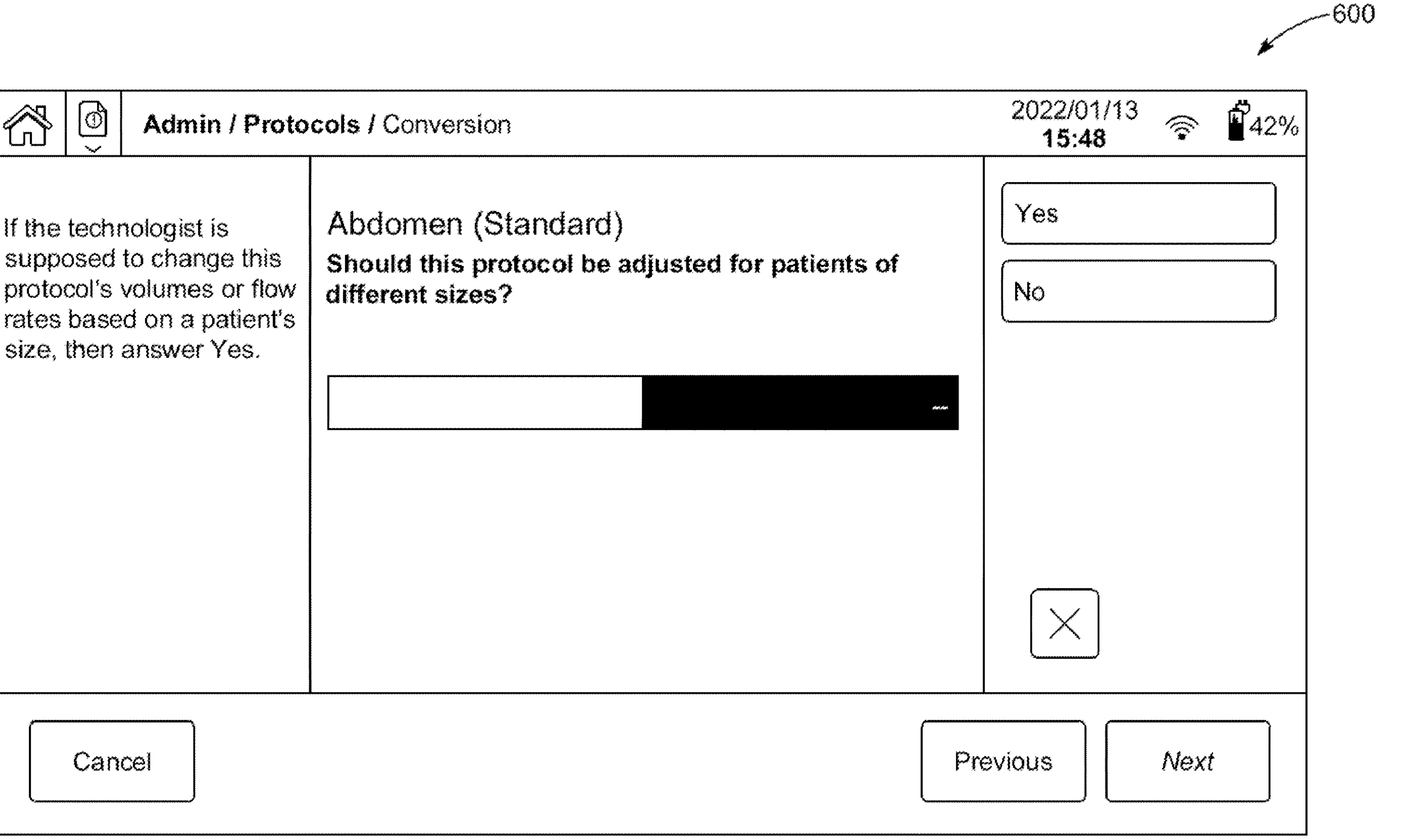
Figure 6E:
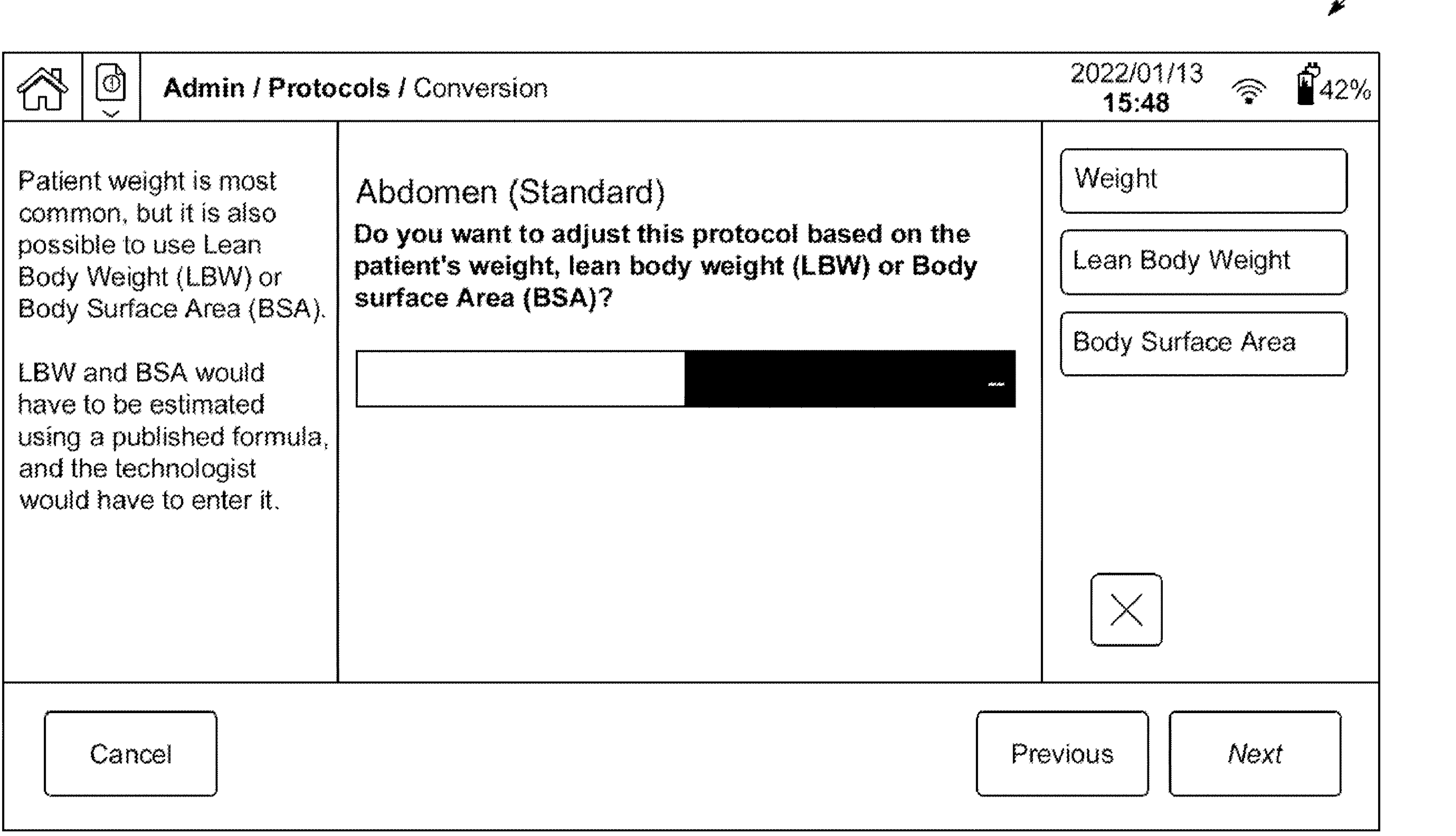
Figure 6F:
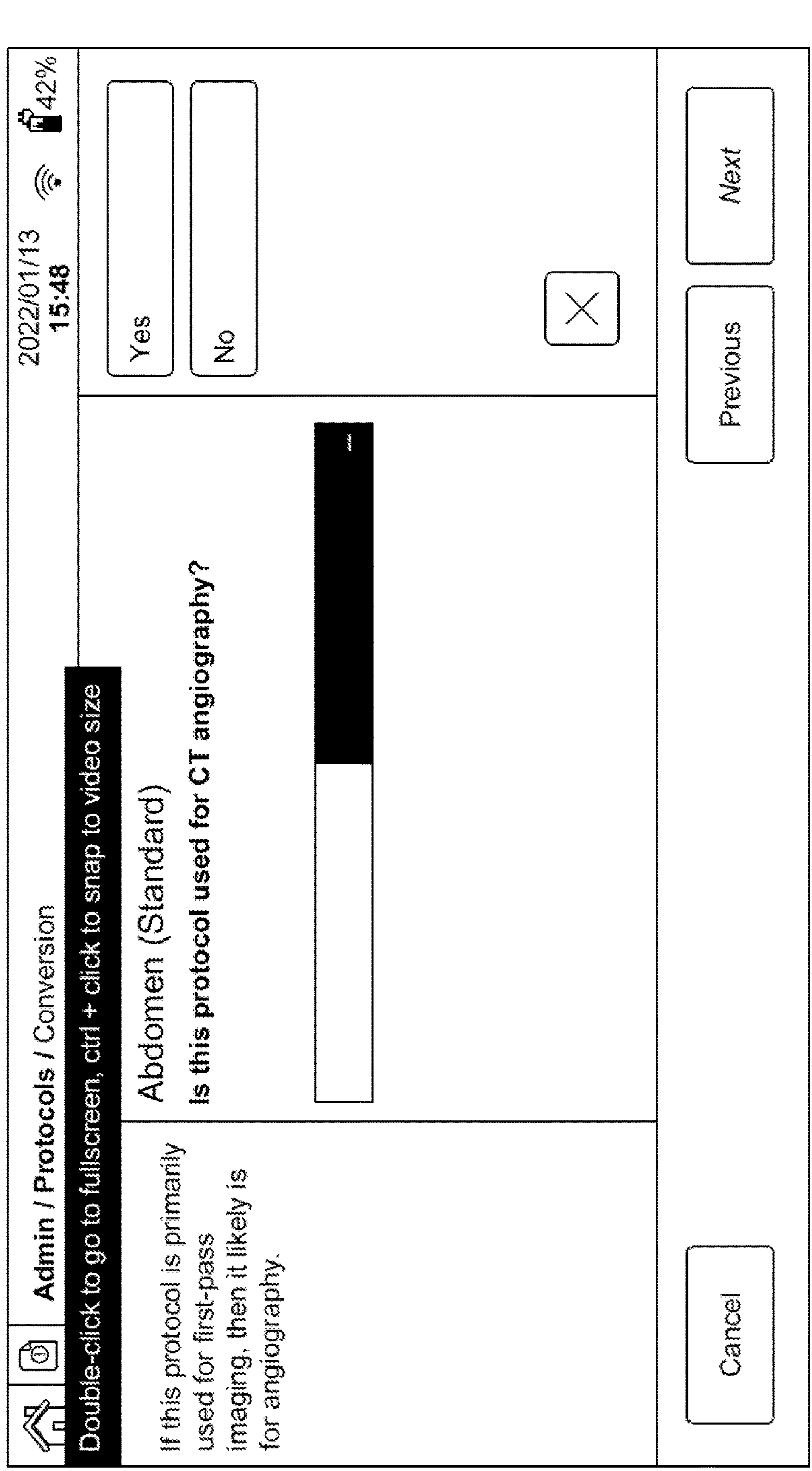
Figure 6G:
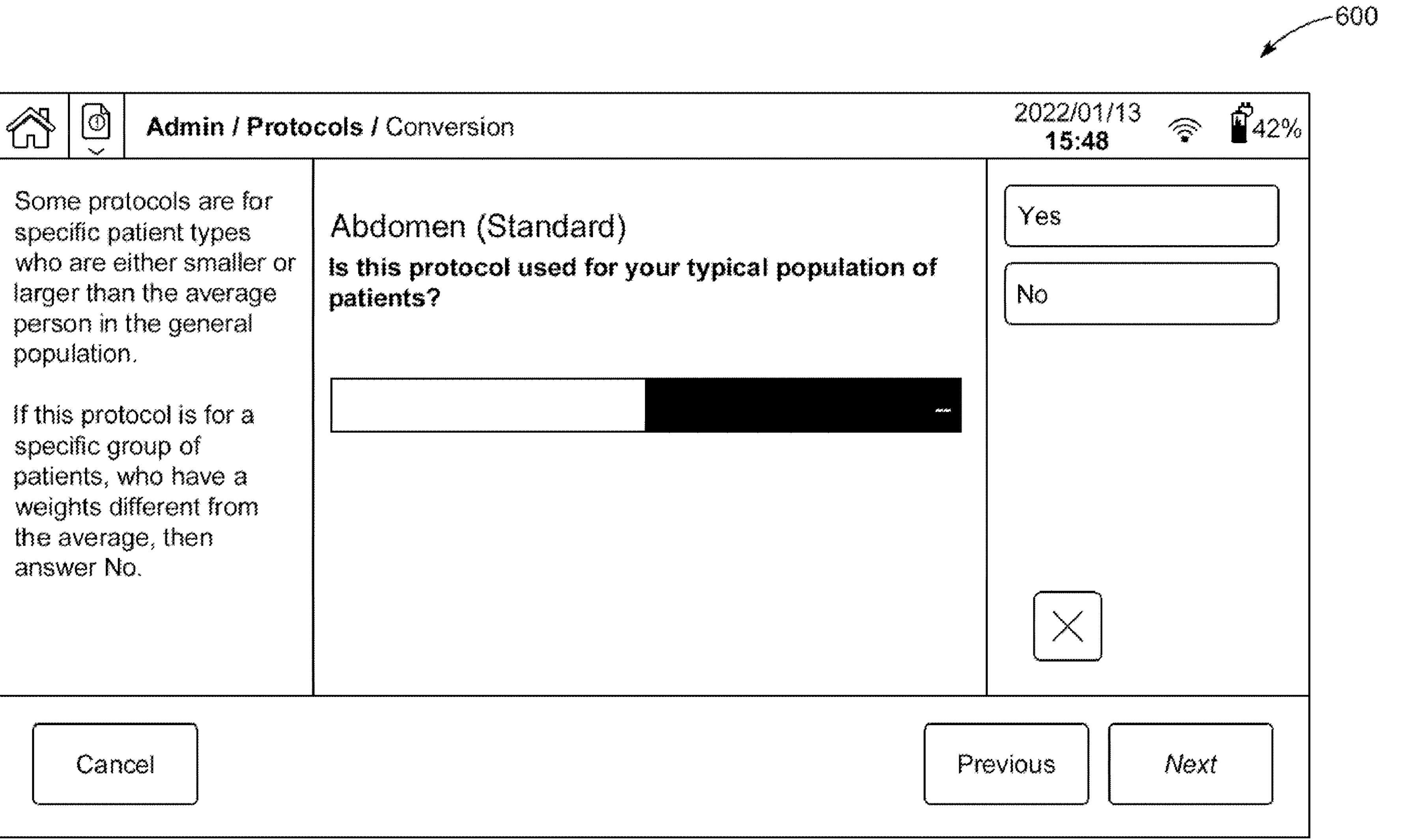
Figure 6H:
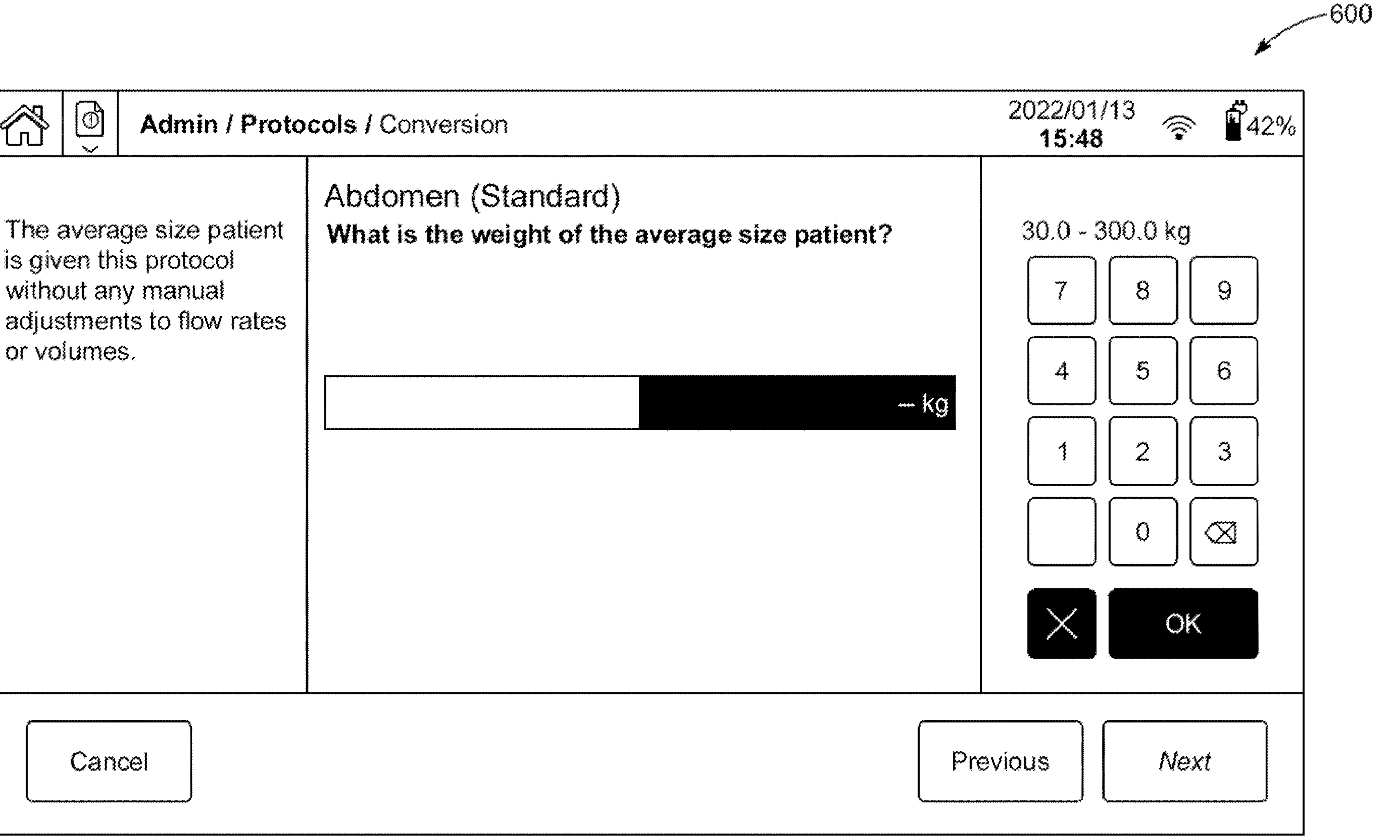
Figure 6I:
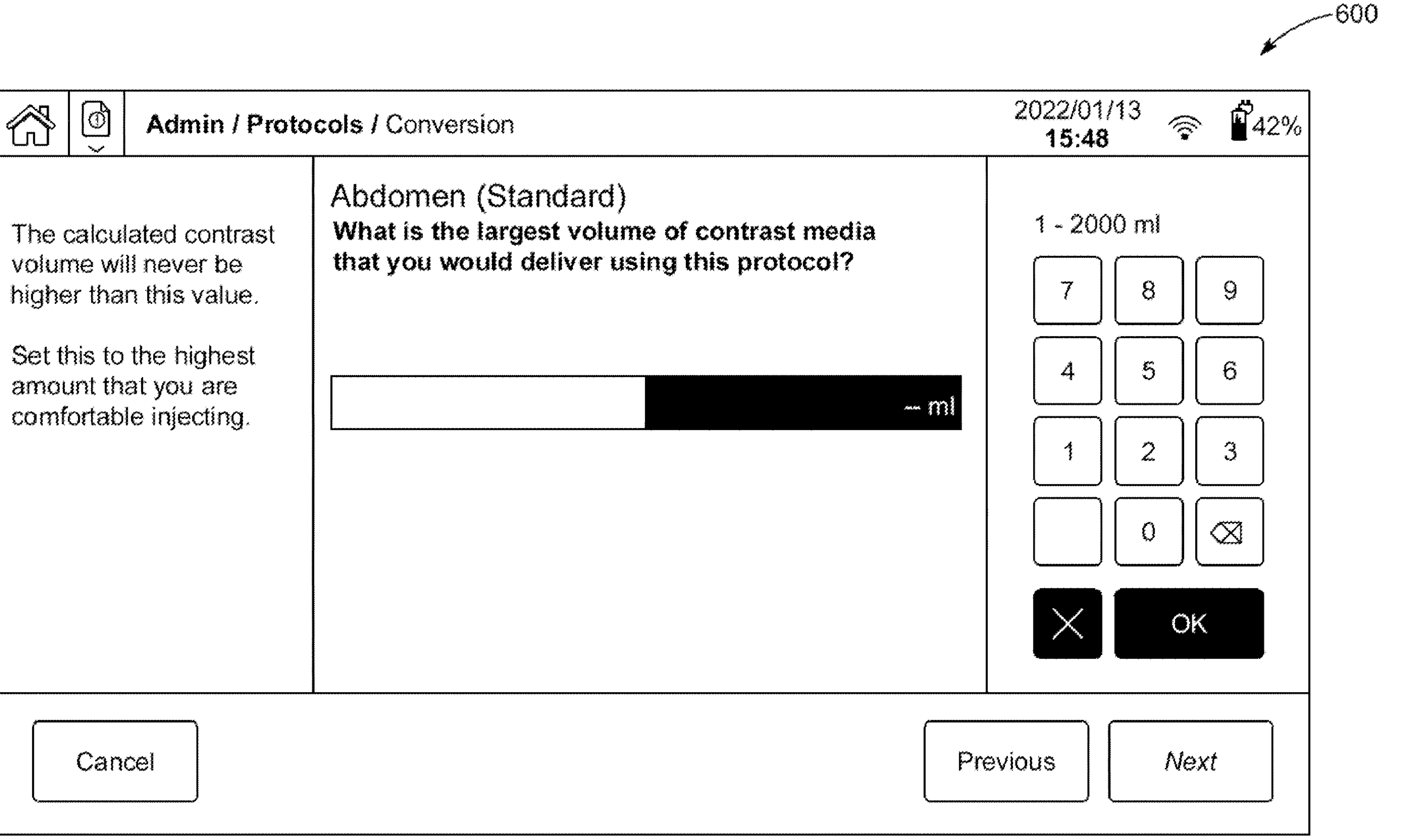
Figure 6J:
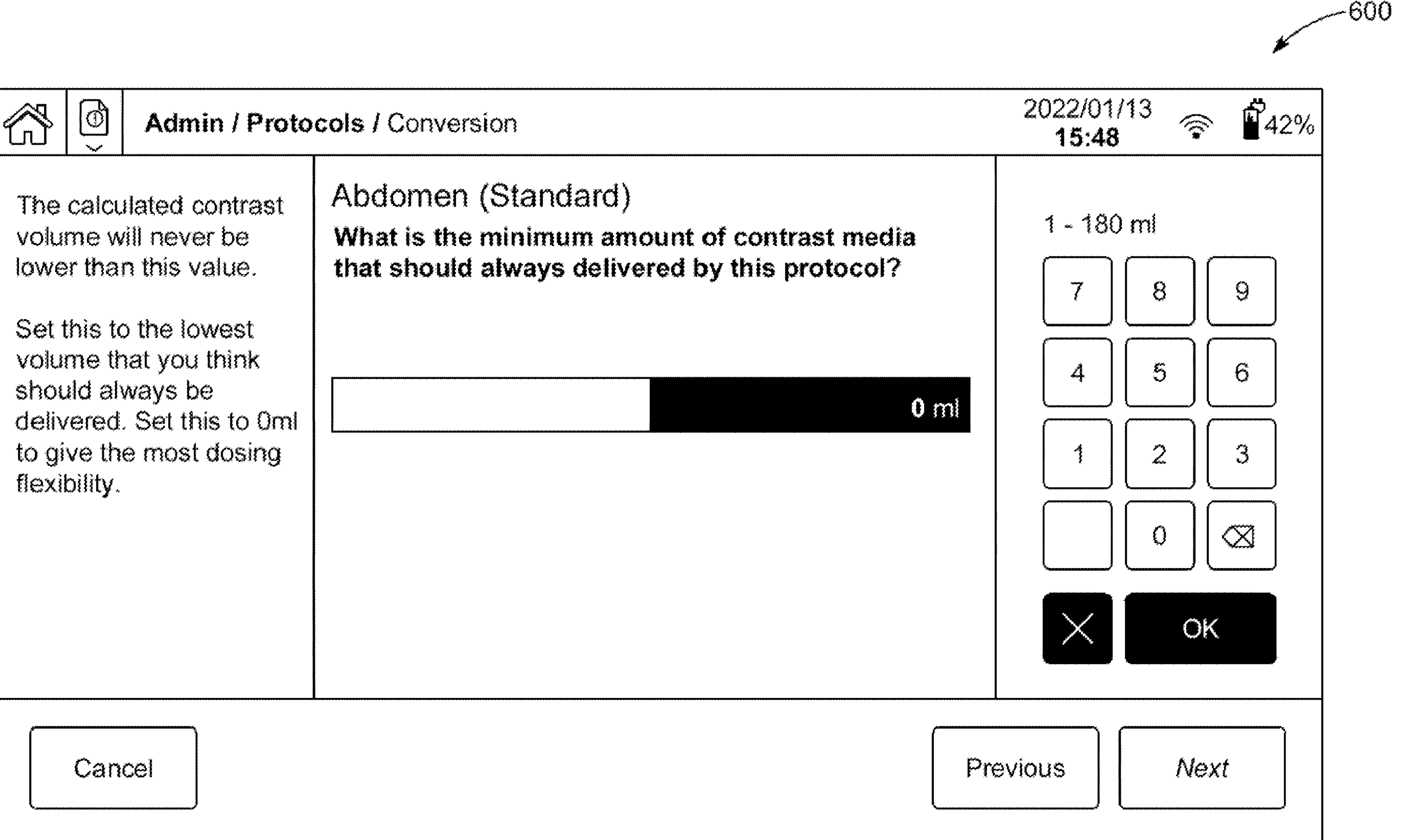
Figure 6K:
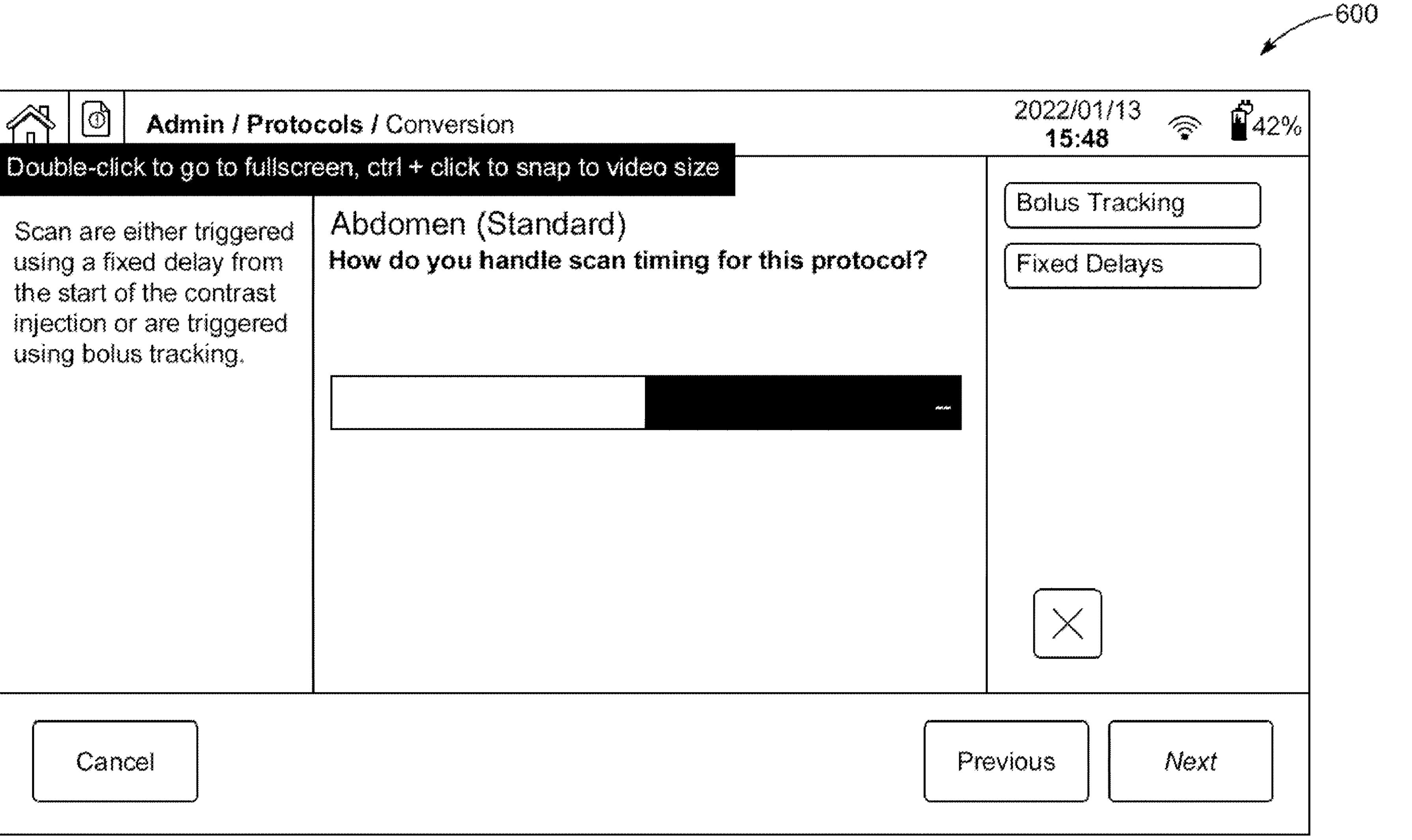
Figure 6L:
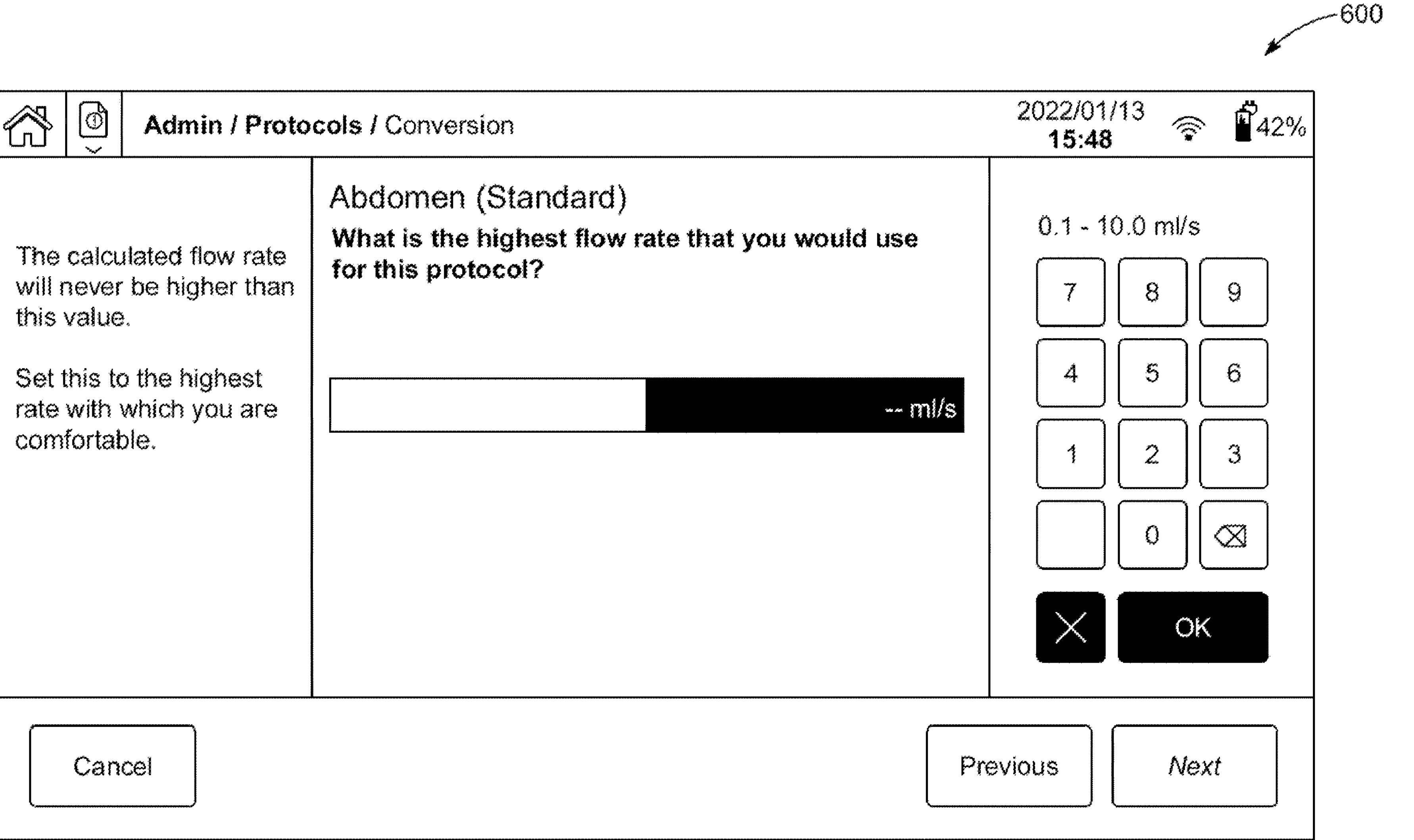
Figure 6M:
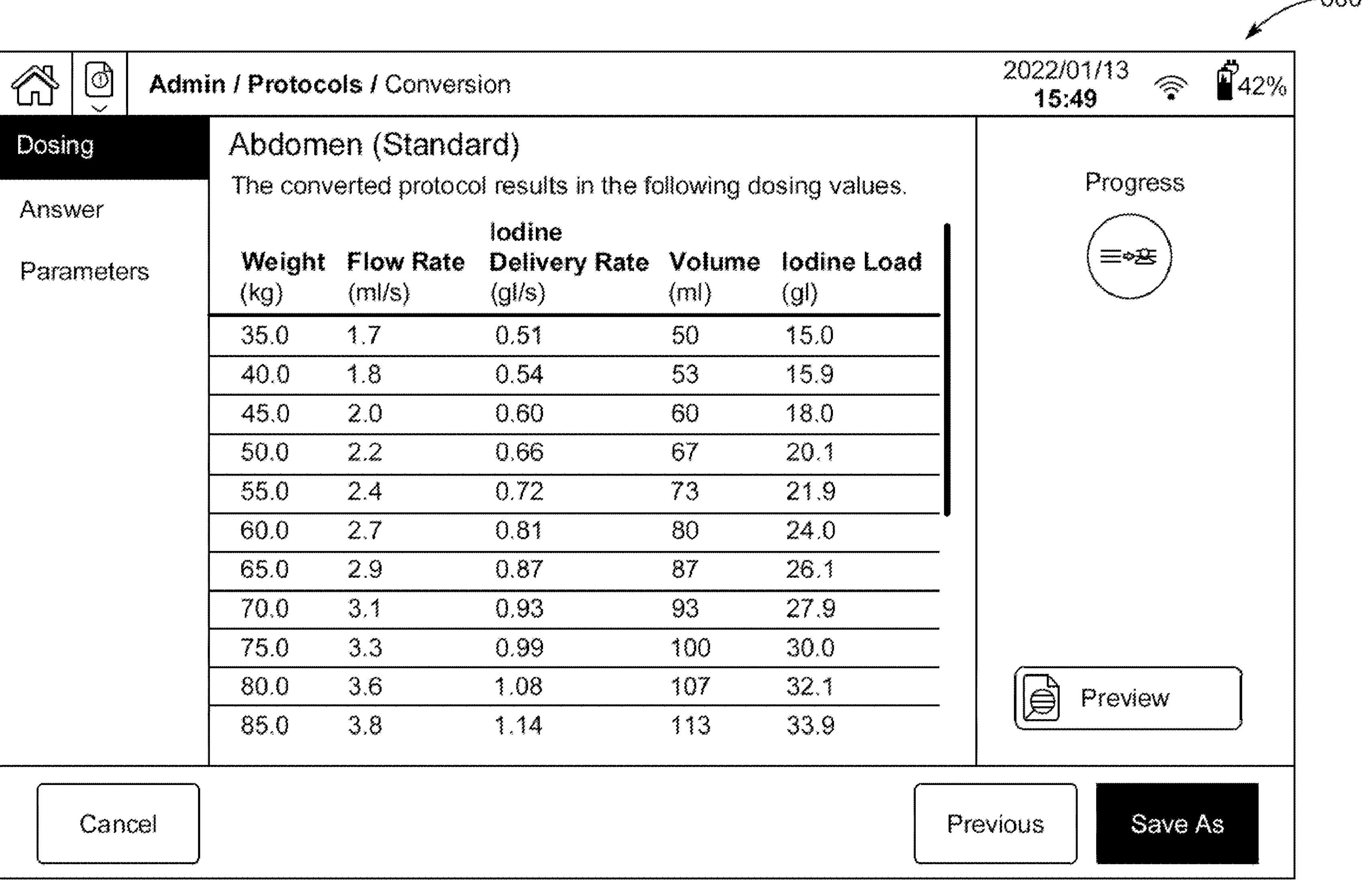
Figure 6N:
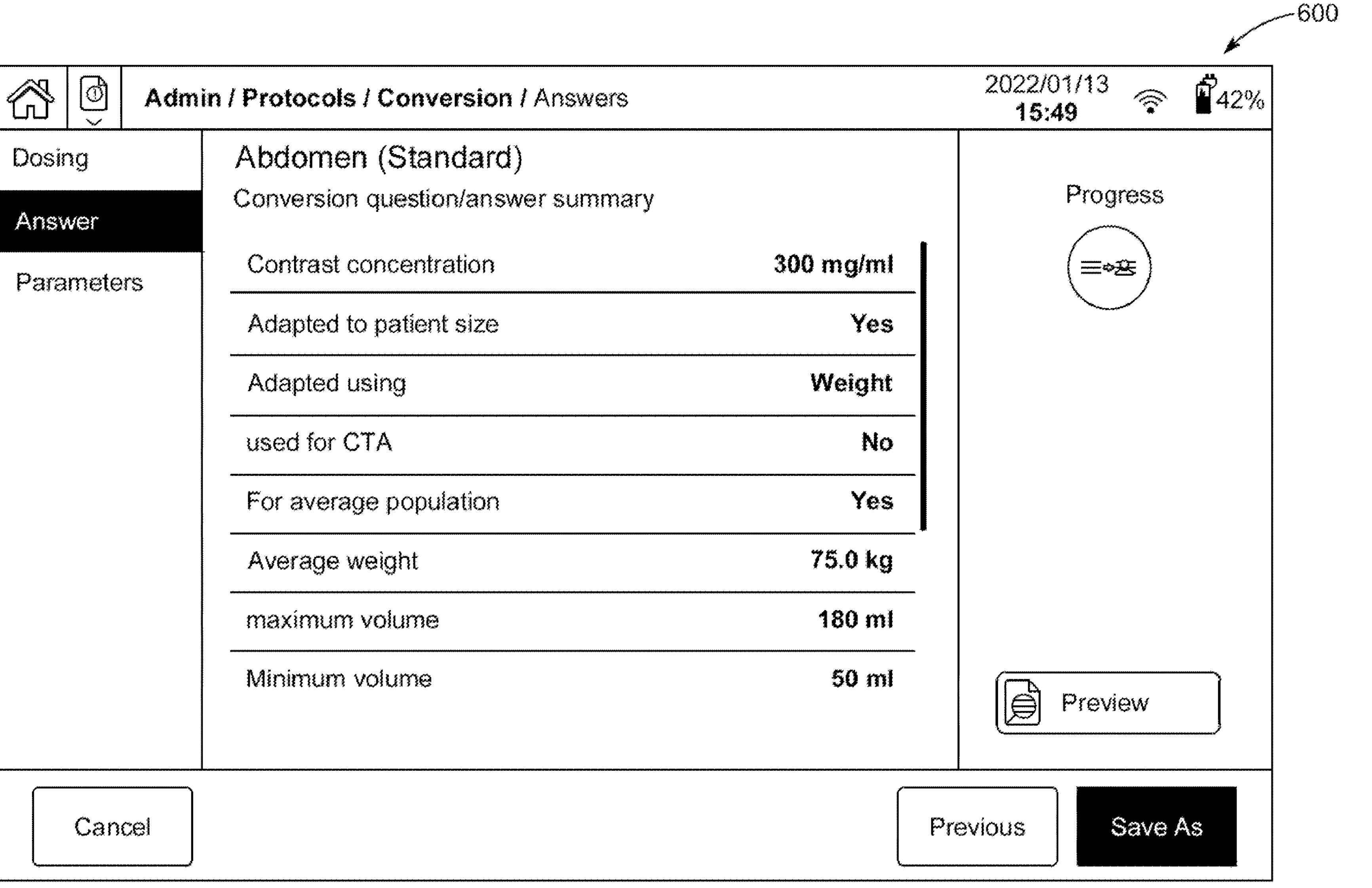
Figure 6O:
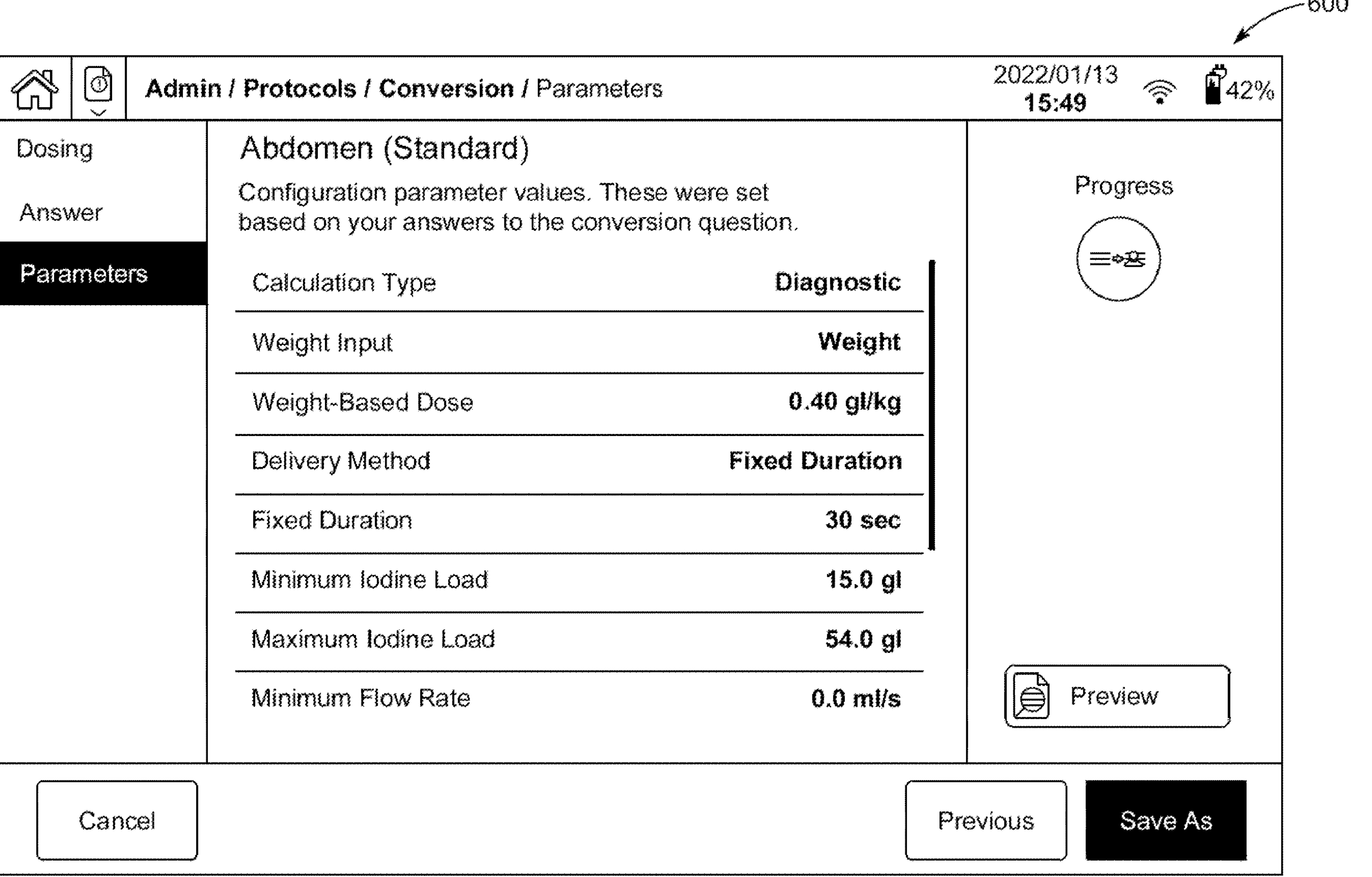
Figure 6P:
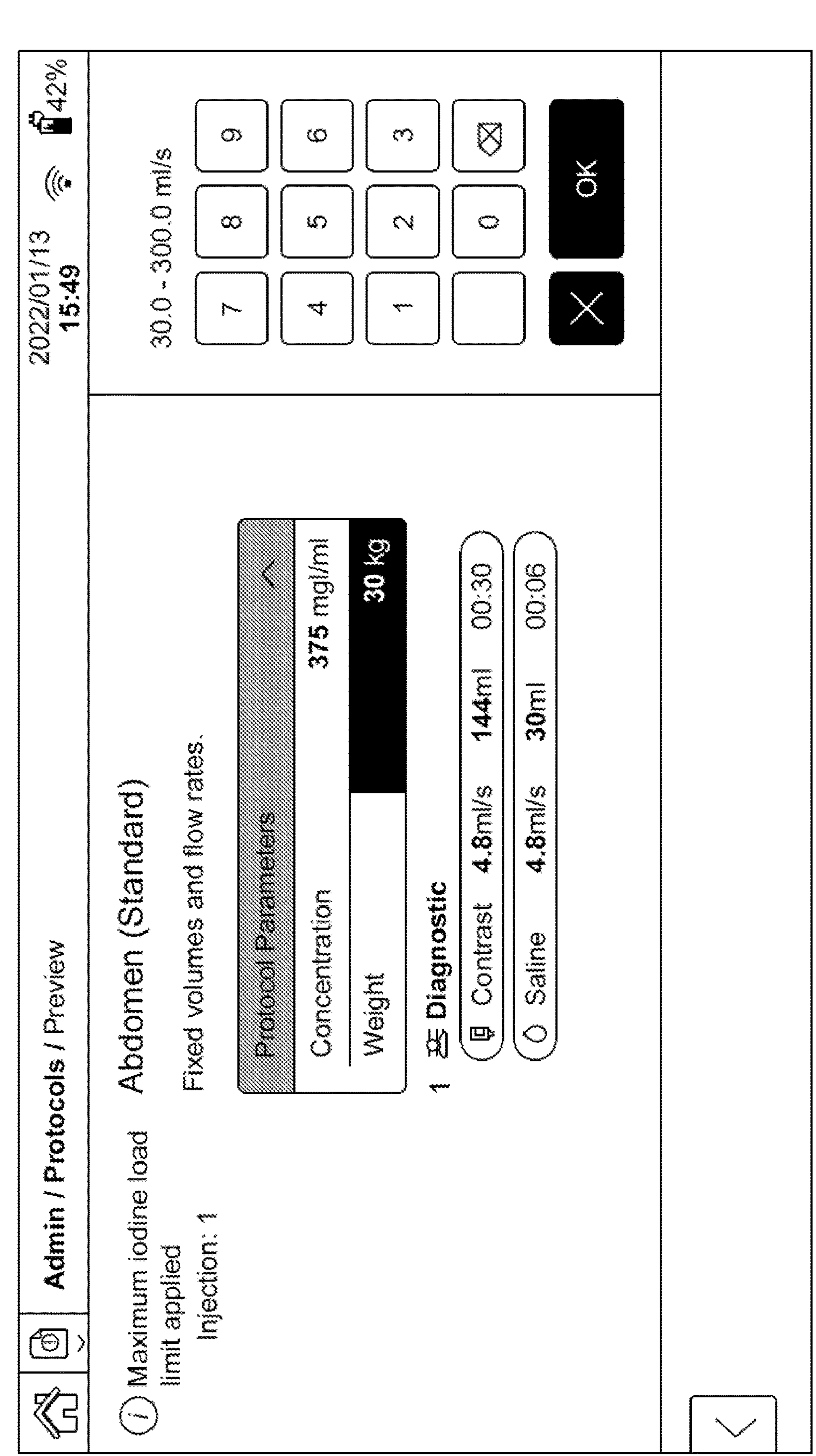
Figure 6Q:
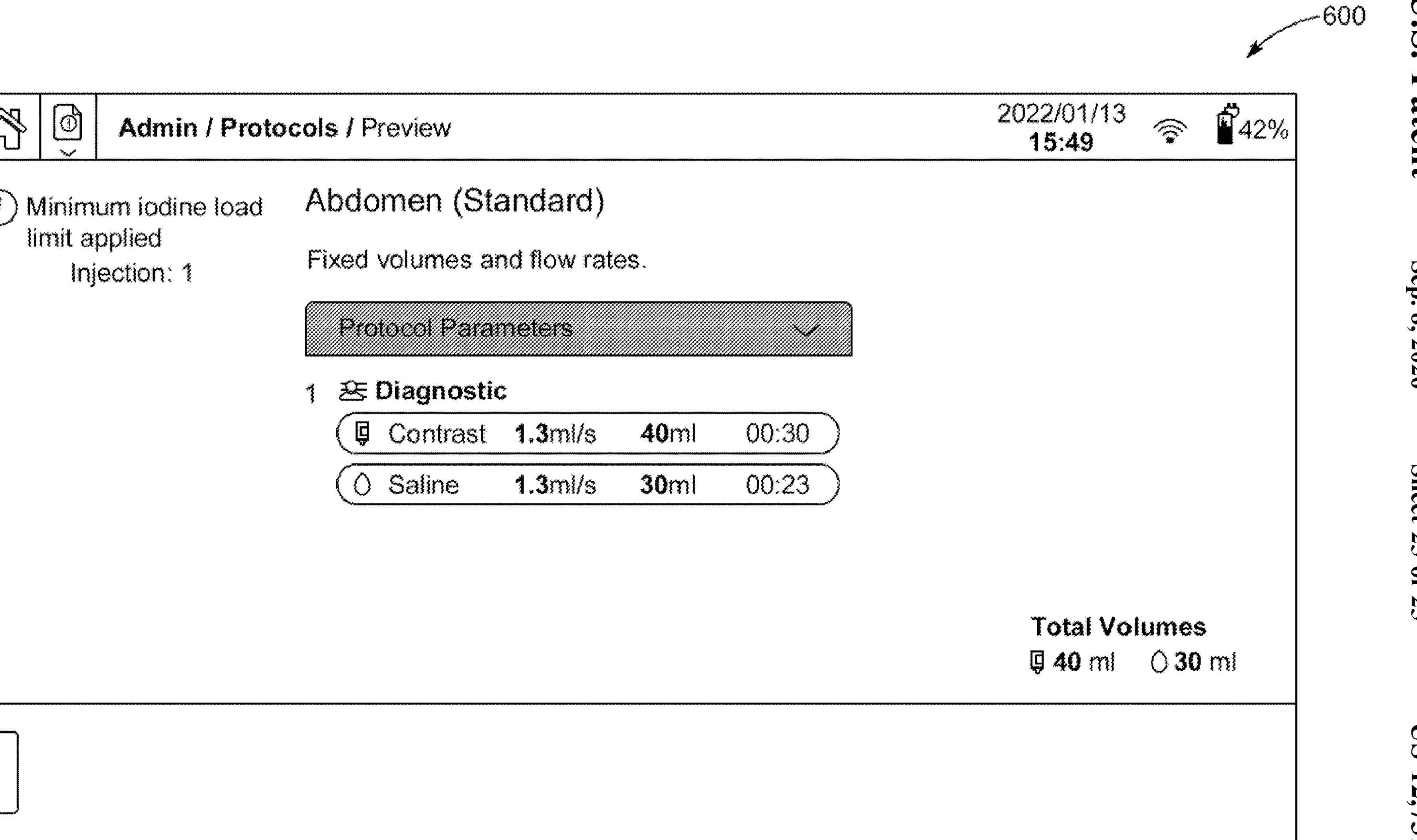

Referring also to FIGS. 6A-6Q, FIGS. 6A-6Q are screenshots 600 of non-limiting embodiments or aspects of a user interface of a process for protocol conversion. For example, injection system 102 may provide and receive, via the user interface, a series of prompts and a corresponding series of user responses, and/or provide, via the user interface, a summary of an iodine dosing of a generated smart protocol, such as the user responses to the prompts and smart protocol parameter values (e.g., the iodine load and iodine delivery rate based on the associated flow rate, volume and selected contrast concentration, etc.). The amount of dosing information visible may depend on the user responses, the final generated smart protocol or algorithm, and/or fixed protocol parameter values.

In such an example, a non-weight based smart protocol may simply display one row of data containing the flow rate, volume, iodine load and iodine delivery rate.

In such an example, if the user has defined the protocol to adapt based on the patient size, the dosing table may provide rows of data for varying weight values. The number of rows can vary. Minimum and maximum flow rate and volume answer values can contribute to "duplicate" data entries in the flow rate and volume at the lower and upper weight ranges. When "duplicate" row data exists, the duplicate row data may not be shown multiple times. Any weight values below/above the lowest/greatest sample data shown may result in the same flow rate and volume values. When the protocol is to be adapted based on patient size, the user can choose to use weight or lean body weight as the expected input value. This choice may be shown in the header and units of the dosing table, and the units of the dosing table may reflect a configuration of the system regarding kg and lb.

In such an example, and as illustrated by FIGS. 4A-4D and FIG. 5, which is a decision tree 500 of non-limiting embodiments or aspects of a process for protocol conversion, a majority of process paths result in an IDL protocol or algorithm being selected for generating the smart protocol. When the user responses indicate a desire to adjust the injection duration based on the estimated scan duration, an IDR protocol or algorithm may be selected for generating the smart protocol, which may result in multiple dosing tables being generated for a few example injection durations. For example, a process path including questions Q32, Q33, Q34, and Q35 in FIG. 5 (and/or steps 430 through 438 in FIG. 4D) may result only in an IDR protocol or algorithm being selected for generating the smart protocol, and a process path including questions Q52 and Q53 in FIG. 5 (and/or steps 414 and 416 in FIG. 4B) may result only in an IDL protocol or algorithm being selected for generating the smart protocol. In other words, a user response of NO to prompt Q3 may set the protocol or algorithm to IDL, a user response of NO to prompt Q31 may set the protocol or algorithm to IDL, and/or a user response of YES to Q31 may set the protocol or algorithm to IDR.

Injection system 102 may preserve certain parameters or properties of the fixed protocol being converted to an iodine based protocol. For example, the pressure limit used in the fixed protocol is still appropriate for the iodine based protocol because conversion to an iodine based protocol does not change injection pressure management goals. As an example, timed reminders on the fixed protocol may give guidance to the user on when actions relating to the scan relative to the injection should be performed. The converted protocol is generated based on the user responses about the goals and intent for the protocol and may preserve the timing of the fixed protocol, which means that timed reminders may still be appropriate and should be preserved. For the IDR algorithm, automatic adjustments made by injection system 102 to the injection protocol may maintain the duration of the injection.

Figure 5:
FIG. 5 is a decision tree of non-limiting embodiments or aspects of a process for protocol conversion.

Table 1 below provides a mapping of which prompts or questions in FIG. 5 set the values to which parameters for the IDL and IDR protocols or algorithms. Because the conversion process allows forward/back navigation, parameters may be set, and the path backtracked and others set. Setting parameters that are not ultimately used may have no effect on the conversion or the created protocol.

TABLE 1

| | IDL | Formula | IDR | |
|---|---|---|---|---|
| Q1 | Concentration | User-entry | Concentration | Q1 |
| | — | ={unit cancellation of values from the fixed protocol and parameters above} | FixedIDR | Q1 |
| Q1 | FixedDose | From the fixed protocol | — | — |
| Q1 | FixedDuration | From the fixed protocol | — | — |
| Q1 | FixedFlowRate | From the fixed protocol | — | — |
| Q1 | SalineFlushVolume | From the fixed protocol | SalineFlushVolume | Q1 |
| Q2, Q21 | WeightInput | User-selection(None, FixedDuration, FixedFlowRate) | WeightInput | Q2, Q21 |
| — | — | From the fixed protocol | InjectionDuration | Q31 |
| Q52 | MaximumFlowRate | User-entry | MaximumFlowRate | Q32 |
| Q53 | MinimumFlowRate | User-entry | MinimumFlowRate | Q33 |
| Q43 | MaximumIodineLoad | =user-entry(max volume)/concentration | MaximumIodineLoad | Q34, Q43 |
| Q44 | MinimumIodineLoad | =user-entry(max volume)/concentration | MinimumIodineLoad | Q35, Q44 |
| Q42ac | Weight | User-entry | Weight | Q42ac |
| | WeightBasedDose | ={unit cancellation of values from the fixed protocol and parameters above} | WeightBasedIDR | |
| Q42bd | LeanBodyWeight | User-entry | LeanBodyWeight | Q42bd |
| | LBWBasedDose | ={unit cancellation of values from the fixed protocol and parameters above} | LBWBasedIDR | |
| Q5, Q51 | DeliveryMethod | User-selection(Bolus Tracking, FixedDelays) | — | — |

In this way, non-limiting embodiments or aspects of the present disclosure provide for converting fixed protocol into a smart protocol that adapts to the concentration of contrast media used, a weight and/or lean body weight of the patient, and/or an injection duration or desired iodine load. For example, injection system 102 may generate one of an iodine dose/load (IDL)-based protocol or algorithm and an iodine delivery rate (IDR)-based protocol or algorithm.

Injection system 102 may calculate parameters of an IDL-based protocol or algorithm as described herein below, where rate is designated by R, volume is designated by V, and duration is designated by D. The subscript indicates the type of media injected where C is for Contrast and S is for Saline. The superscript indicates the calculation type of the injection where TI is for Test Injection and D is for Diagnostic. For example, $V_c^D$ represents the Volume of the Contrast phase of the Diagnostic calculation.

Iodine Load (IL) for an IDL-based smart protocol or algorithm may be calculated based on the fixed dose or from the appropriate weight-based dose factor multiplied by the patient's Weight or Lean Body Weight. For example, IL may be calculated according to the following Equations (1)-(3):

$$\text{If Weight Input=None IL (gl)=Fixed Dose (gl)} \tag{1}$$

$$\text{If Weight Input=Weight IL (gl)=Weight Based Dose (gl/kg)*Weight (kg)} \tag{2}$$

$$\text{If Weight Input=Lean Body Weight IL (gl)=LBW Based Dose (gl/kg LBW)*Lean Body Weight (kg LBW)} \tag{3}$$

In some non-limiting embodiments or aspects, another dosing basis, such as body surface area (BSA), and/or the like, may be used for calculating the IL. When Weight Input is not None (i.e., when the IL varies with patient size), if the calculated Iodine Load is lower than the Minimum Iodine Load, a "Minimum Iodine Load Limit Applied" notice is provided, and the Minimum Iodine Load value is used instead. In other words, If (round (IL)<Minimum Iodine Load), IL (gl)=Minimum Iodine Load (gl). If the calculated Iodine Load exceeds the Maximum Iodine Load, a "Maximum Iodine Load Limit Applied" notice is provided, and the Maximum Iodine Load is used instead. In other words, If (round (IL)>Maximum Iodine Load), IL (gl)=Maximum Iodine Load (gl).

Flow rate and volume for an IDL-based smart protocol or algorithm may be dependent on the Delivery Method parameter. When the delivery method is set to Fixed Flow Rate, the flow rate is simply set to the Fixed Flow Rate parameter value. No limits are applied to this parameter because the flow rate is a fixed value (e.g., R(ml/s)=Fixed Flow Rate (ml/s), etc.). The calculated injection volume of the contrast phase is based on the calculated IL and the contrast media concentration according to the following Equation (4):

$$Vc^D(\text{ml}) = \frac{IL(\text{gl}) * 1000}{\text{Concentration (mgl/ml)}} \quad (4)$$

When the Delivery Method is set to Fixed Duration, the Flow Rate may be calculated based on the calculated IL, the contrast media concentration, and the fixed duration according to the following Equation (5):

$$R(\text{ml/s}) = \frac{IL(\text{gl}) * 1000}{\text{Concentration (mgl/ml)} * \text{Fixed Duration (s)}} \quad (5)$$

If the computed Flow Rate is below the Minimum Flow Rate, a “Minimum Flow Rate Limit Applied” notice may be provided, and the Flow Rate may be increased to the Minimum Flow Rate. If the Minimum Flow Rate value is 0, the minimum deliverable Flow Rate of 0.1 is used for comparison. In other words, If (round (R)<Minimum Flow Rate), R (ml/s)=Minimum Flow Rate (ml/s).

If the computed Flow Rate is above the Maximum Flow Rate, a “Maximum Flow Rate Limit Applied” notice is provided, and the Flow Rate is decreased to the Maximum Flow Rate. In other words, if (round (R)>Maximum Flow Rate), R (ml/s)=Maximum Flow Rate (ml/s).

The computed Flow Rate may be used to calculate the Flow Rate Based Iodine Load according to the following Equation (6):

$$\text{Flow Rate Based } IL(\text{gl}) = \frac{R(\text{ml/s}) * \text{Concentration (mgl/ml)} * \text{Fixed Duration (s)}}{1000} \quad (6)$$

If the Flow Rate Based Iodine Load is below the Minimum Iodine Load, a “Min Max Iodine Load Flow Rate Conflict” notice is provided, and the originally calculated Iodine Load is used to calculate the Flow Rate according to the following Equation (7):

$$\text{If (round (Flow Rate Based } IL) < \text{Minimum Iodine Load)} \quad (7)$$
$$R(\text{ml/s}) = \frac{IL(\text{gl}) * 1000}{\text{Concentration (mgl/ml)} * \text{Fixed Duration (s)}}$$

If the Flow Rate Based Iodine Load is above the Maximum Iodine Load, a “Min Max Iodine Load Flow Rate Conflict” notice is provided, and the originally calculated Iodine Load is used to calculate the Flow Rate according to the following Equation (8):

$$\text{If (round (Flow Rate Based } IL) > \text{Maximum Iodine Load)} \quad (8)$$
$$R(\text{ml/s}) = \frac{IL(\text{gl}) * 1000}{\text{Concentration (mgl/ml)} * \text{Fixed Duration (s)}}$$

Once the Flow Rate is calculated, the diagnostic injection's contrast phase volume is calculated using the Flow Rate and the Fixed Duration according to $V_C^D$ (ml)=R(ml/s)*Fixed Duration(s). Finally, the diagnostic injection's saline volume is simply set to the Saline Flush Volume parameter value according to $V_S^D$ (ml)=Saline Flush Volume (ml).

A Test Inject Volume may be either duration or volume based. For example, if (Test Inject Delivery Method==Injection Duration), $V_S^{TI}$ (ml)=R*Test Inject Duration(s) else $V_S^{TI}$ (ml)=Test Inject Volume (ml).

Injection system 102 may calculate parameters of an IDR-based protocol or algorithm as described herein below, where rate is designated by R, volume is designated by V, and duration is designated by D. The subscript indicates the type of media injected where C is for Contrast and S is for Saline. The superscript indicates the calculation type of the injection where TI is for Test Injection and D is for Diagnostic. For example, $V_c^D$ represents the Volume of the Contrast phase of the Diagnostic calculation.

IL for an IDR-based smart protocol or algorithm may be calculated based on an IDR multiplied by the Injection Duration. The IDR (gl/s) value depends on the type of Weight Input handling and may be calculated according to the following Equations (9)-(11):

If Weight Input=None IL (gl)=Fixed IDR (gl/s)*Injection Duration(s) (9)

If Weight Input=Weight IL (gl)=Weight-Based IDR (gl/s/kg)*Weight (kg)*Injection Duration(s) (10)

If Weight Input=Lean Body Weight (LBW) IL (gl)=LBW-Based IDR (gl/s/kg LBW)*Lean Body Weight (kg LBW)*Injection Duration(s) (11)

If the calculated Iodine Load is lower than the Minimum Iodine Load, a “Minimum Iodine Load Limit, IDR Increased” notice is provided, and the Minimum Iodine Load value is used instead. In other words, If (round (IL)<Minimum Iodine Load, IL (gl)=Minimum Iodine Load (gl).

If the calculated Iodine Load exceeds the Maximum Iodine Load, a “Maximum Iodine Load Limit, IDR Decreased” notice is provided, and the Maximum Iodine Load is used instead. In other words, If (round (IL)>Maximum Iodine Load, IL (gl)=Maximum Iodine Load (gl).

The diagnostic injection's Flow Rate is calculated by dividing the calculated Iodine Load by the Concentration of the contrast media and the Injection Duration according to the following Equation (12):

$$R(\text{ml}) = \frac{IL(\text{gl}) * 1000}{\text{Concentration (mgl/ml)} * \text{Injection Duration (s)}} \quad (12)$$

If the computed Flow Rate is below the Minimum Flow Rate, a “Minimum Flow Rate Limit, IDR Increased” notice is provided, and the Flow Rate is increased to the Minimum Flow Rate. If the Minimum Flow Rate value is 0, the minimum deliverable Flow Rate of 0.1 is used for the comparison. In other words, if (round (R)<Minimum Flow Rate), R (ml/s)=Minimum Flow Rate (ml/s).

If the computed Flow Rate is above the Maximum Flow Rate, a “Maximum Flow Rate Limit, IDR Decreased” notice is provided, and the Flow Rate is decreased to the Maximum Flow Rate. In other words, if (round (R)>Maximum Flow Rate), R (ml/s)=Maximum Flow Rate (ml/s).

The computed Flow Rate is used to calculate the Flow Rate Based Iodine Load according to the following Equation (13):

$$\text{Flow Rate Based } IL\text{ (gl)} = \frac{R(\text{ml/s}) * \text{Concentration}(\text{mgl/ml}) * \text{Injection Duration (s)}}{1000} \tag{13}$$

If the Flow Rate Based Iodine Load is below the Minimum Iodine Load, a "Min Max Iodine Load Flow Rate Conflict" notice is provided, and the originally calculated Iodine Load is used to calculate the Flow Rate according to the following Equation (14):

$$\text{If (round (Flow Rate Based } IL) < \text{Minimum Iodine Load)} \tag{14}$$

$$R(\text{ml}) = \frac{IL(\text{gl}) * 1000}{\text{Concentration}(\text{mgl/ml}) * \text{Injection Duration (s)}}$$

If the Flow Rate Based Iodine Load is above the Maximum Iodine Load, a "Min Max Iodine Load Flow Rate Conflict" notice is provided, and the originally calculated Iodine Load is used to calculate the Flow Rate according to the following Equation (15):

$$\text{If (round (Flow Rate Based } IL) < \text{Maximum Iodine Load)} \tag{15}$$

$$R(\text{ml}) = \frac{IL(\text{gl}) * 1000}{\text{Concentration}(\text{mgl/ml}) * \text{Injection Duration (s)}}$$

Once the Flow Rate is calculated, the diagnostic injection's contrast phase volume is calculated using the Flow Rate and the Injection Duration according to $V_C^D$ (ml)=R (ml/s)*Injection Duration(s). Finally, the diagnostic injection's saline volume is simply set to the Saline Flush Volume parameter value according to $V_S^D$ (ml)=Saline Flush Volume (ml).

The Test Inject Volume may be either duration or volume based. For example, If (Test Inject Delivery Method==Injection Duration), $V_S^{TI}$ (ml)=R*Test Inject Duration(s), else $V_S^{TI}$ (ml)=Test Inject Volume (ml).

As shown in FIG. 3, at step 310, process 300 includes receiving user input for an injection. For example, injection system 102 may receive user input associated with a smart protocol for an injection. As an example, injection system 102 may receive, via the user interface of the computing device, user input associated with the smart protocol for the injection. In such an example, injection system 102 may receive, via the user interface of the computing device, a selection of the smart protocol from a plurality of available smart protocols and/or fixed protocols. In such an example, injection system 102 may receive, for each patient, the selection of the smart protocol for that patient at an exam time for that patient.

In some non-limiting embodiments or aspects, user input may include at least one of the following: a weight of the patient, a lean body weight of the patient, a body surface area (BSA) of the patient, or any combination thereof.

As shown in FIG. 3, at step 312, process 300 includes calculating values of smart protocol parameters of a smart protocol based on user input. For example, injection system 102 may calculate values of smart protocol parameters of a smart protocol based on user input. As an example, injection system 102 may calculate, based on the user input, values of the smart protocol parameters of the smart protocol.

As shown in FIG. 3, at step 314, process 300 includes controlling an injection system to deliver fluid to a patient according to smart protocol parameters of a smart protocol. For example, injection system 102 may control an injector of injection system 102 to deliver fluid to a patient according to smart protocol parameters of a smart protocol. As an example, injection system 102 may control, according to the values of the smart protocol parameters of the smart protocol, the injection system to deliver the at least one fluid to the patient in the injection.

Referring now to FIGS. 4A-4D, FIGS. 4A-4D depict a flowchart of non-limiting embodiments or aspects of a process 400 for protocol conversion. In some non-limiting embodiments or aspects, one or more of the steps of process 400 may be performed (e.g., completely, partially, etc.) by injection system 102. In some non-limiting embodiments or aspects, one or more of the steps of process 300 may be performed (e.g., completely, partially, etc.) by another device or a group of devices separate from or including injection system 102, such as user device 108.

Figure 4A:
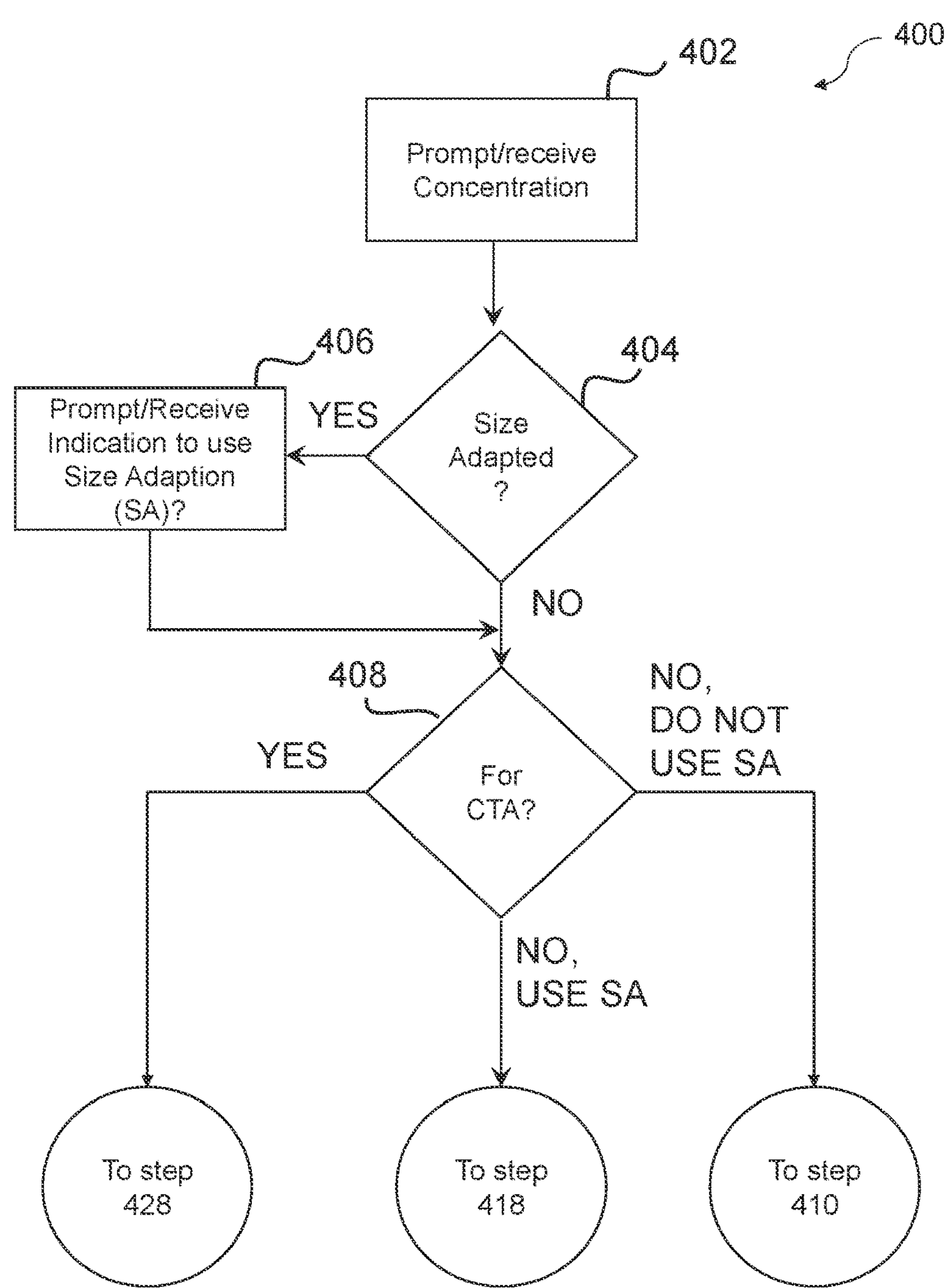
FIGS. 4A-4D are a flowchart of non-limiting embodiments or aspects of a process for protocol conversion.

As shown in FIG. 4A, at step 402, process 400 includes providing a prompt for a concentration of a contrast media and receiving a user response including the concentration of the contrast media. For example, injection system 102 may provide a prompt for a concentration of a contrast media and receive a user response including the concentration of the contrast media.

As shown in FIG. 4A, at step 404, process 400 includes providing a prompt for an indication of whether a fixed protocol is adapted based on a size of a patient, receiving a user response including the indication of whether a fixed protocol is adapted based on a size of a patient, and controlling, based on the indication of whether a fixed protocol is adapted based on a size of a patient, processing to proceed directly to one of step 406 and step 408 of process 400. For example, injection system 102 may provide a prompt for an indication of whether a fixed protocol is adapted based on a size of a patient, receive a user response including the indication of whether a fixed protocol is adapted based on a size of a patient, and control based on the user response including the indication of whether a fixed protocol is adapted based on a size of a patient, processing to proceed directly to one of step 406 and step 408 of process 400.

In such an example, in response to receiving a user response including an indication that a fixed protocol is adapted based on a size of a patient, injection system 102 may control processing to proceed directly to step 406 of process 400.

In such an example, in response to receiving a user response including an indication that a fixed protocol is not adapted based on a size of a patient, injection system 102 may control processing to proceed directly to step 408 of process 400.

As shown in FIG. 4A, at step 406, process 400 includes, in response to receiving a user response including an indication that a fixed protocol is adapted based on a size of a patient, providing a prompt for an indication of whether to adapt a smart protocol based on a size of a patient, and receiving a user response including the indication of whether to adapt a smart protocol based on a size of a patient. For example, in response to the user response including the indication that a fixed protocol is adapted based on a size of a patient, injection system 102 may provide a prompt for an indication of whether to adapt a smart protocol based on a size of a patient, and receive a user response including the indication of whether to adapt a smart protocol based on a size of a patient.

As shown in FIG. 4A, at step 408, process 400 includes, in response to (i) receiving a user response including an indication that a fixed protocol is not adapted based on a size of a patient or (ii) receiving a user response including the indication of whether to adapt a smart protocol based on a size of a patient, providing a prompt for an indication of whether a fixed protocol is for computed tomography angiography (CTA), receiving a user response including the indication of whether a fixed protocol is for CTA, and controlling, based on (i) the user response including the indication of whether to adapt a smart protocol based on a size of a patient and (ii) the user response including the indication of whether a fixed protocol is for CTA, processing to proceed directly to one of step 410, step 418, and step 428 of process 400. For example, injection system 102 may, in response to (i) receiving the user response including the indication that a fixed protocol is not adapted based on a size of a patient or (ii) receiving the user response including the indication of whether to adapt a smart protocol based on a size of a patient, provide a prompt for an indication of whether a fixed protocol is for computed tomography angiography (CTA), receive a user response including the indication of whether a fixed protocol is for computed tomography angiography (CTA), and control, based on (i) the user response including the indication of whether to adapt a smart protocol based on a size of a patient and (ii) the user response including the indication of whether a fixed protocol is for CTA, processing to proceed directly to one of step 410, step 418, and step 428 of process 400.

In such an example, in response to receiving (i) the user response including the indication to not adapt a smart protocol based on a size of a patient and (ii) the user response including the indication that a fixed protocol is not for CTA, injection system 102 may control processing to proceed directly to step 410 of process 400.

In such an example, in response to receiving (i) the user response including the indication to adapt a smart protocol based on a size of a patient and (ii) the user response including the indication that a fixed protocol is not for CTA, injection system 102 may control processing to proceed directly to step 418 of process 400.

In such an example, in response to receiving the user response including the indication that a fixed protocol is for CTA, injection system 102 may control processing to proceed directly to step 428 of process 400.

Figure 4B:
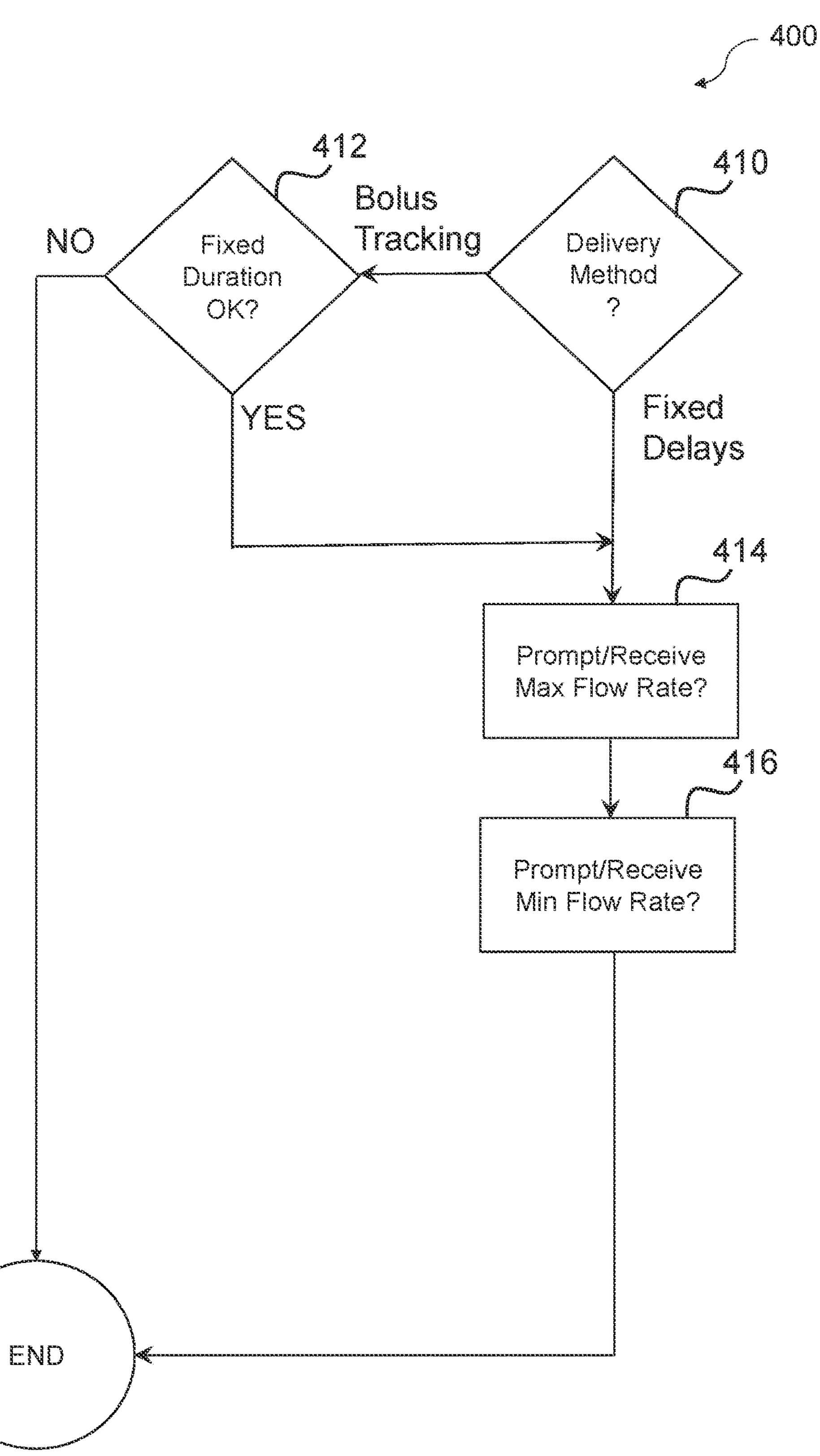

As shown in FIG. 4B, at step 410, process 400 includes providing a prompt for an indication of a type of delivery method associated with a fixed protocol, receiving a user response including the indication of a type of delivery method associated with a fixed protocol, and controlling, based on the user response including the indication of a type of delivery method associated with a fixed protocol, processing to proceed directly to one of step 412 and step 414 of process 400. For example, injection system 102 may provide a prompt for an indication of a type of delivery method associated with a fixed protocol, receive a user response including the indication of a type of delivery method associated with a fixed protocol, and control, based on the user response including the indication of a type of delivery method associated with a fixed protocol, processing to proceed directly to one of step 412 and step 414 of process 400.

In such an example, in response to the user response including an indication that a type of delivery method associated with a fixed protocol is a bolus tracking delivery method, injection system 102 may control processing to proceed directly to step 412 of process 400.

In such an example, in response to the user response including an indication that a type of delivery method associated with a fixed protocol is a fixed delays delivery method, injection system 102 may control processing to proceed directly to step 414 of process 400.

As shown in FIG. 4B, at step 412, process 400 includes, in response to receiving the user response including the indication that a type of delivery method associated with a fixed protocol is a bolus tracking delivery method, providing a prompt for an indication of whether a duration of the fixed protocol is adjusted based on a duration of a CTA scan, receiving a user response including the indication of whether a duration of the fixed protocol is adjusted based on a duration of a CTA scan, and controlling, based on the user response including the indication of whether a duration of the fixed protocol is adjusted based on a duration of a CTA scan, processing to one of proceed directly to step 414 of process 400 and end process 400. For example, injection system 102 may, in response to receiving the user response including the indication that a type of delivery method associated with a fixed protocol is a bolus tracking delivery method, provide a prompt for an indication of whether a duration of the fixed protocol is adjusted based on a duration of a CTA scan, receive a user response including the indication of whether a duration of the fixed protocol is adjusted based on a duration of a CTA scan, and control, based on the user response including the indication of whether a duration of the fixed protocol is adjusted based on a duration of a CTA scan, processing to one of proceed directly to step 414 of process 400 and end process 400.

In such an example, in response to the user response including the indication that a duration of the fixed protocol is not adjusted based on a duration of a CTA scan, injection system 102 may control processing to end process 400.

In such an example, in response to the user response including the indication that a duration of the fixed protocol is adjusted based on a duration of a CTA scan, injection system 102 may control processing to proceed directly to step 414 of process 400.

As shown in FIG. 4B, at step 414, process 400 includes, in response to (i) receiving a user response including an indication that a type of delivery method associated with a fixed protocol is a fixed delays delivery method or (ii) receiving a user response including the indication that a duration of the fixed protocol is adjusted based on a duration of a CTA scan, providing a prompt for a maximum flow rate of at least one fluid associated with a fixed protocol, and receiving a user response including the maximum flow rate of at least one fluid associated with a fixed protocol. For example, injection system 102 may, in response to (i) receiving a user response including an indication that a type of delivery method associated with a fixed protocol is a fixed delays delivery method or (ii) receiving a user response including the indication that a duration of the fixed protocol is adjusted based on a duration of a CTA scan, provide a prompt for a maximum flow rate of the at least one fluid associated with the fixed protocol, and receive a user response including the maximum flow rate of the at least one fluid associated with the fixed protocol.

As shown in FIG. 4B, at step 416, process 400 includes providing a prompt for a minimum flow rate of at least one fluid associated with a fixed protocol, and receiving a user response including the minimum flow rate of at least one fluid associated with a fixed protocol. For example, injection system 102 may provide a prompt for a minimum flow rate of the at least one fluid associated with the fixed protocol, and receive a user response including the minimum flow rate of the at least one fluid associated with the fixed protocol.

In such an example, in response to receiving the user response including the minimum flow rate of the at least one fluid associated with the fixed protocol, injection system 102 may control processing to end process 400.

Figure 4C:
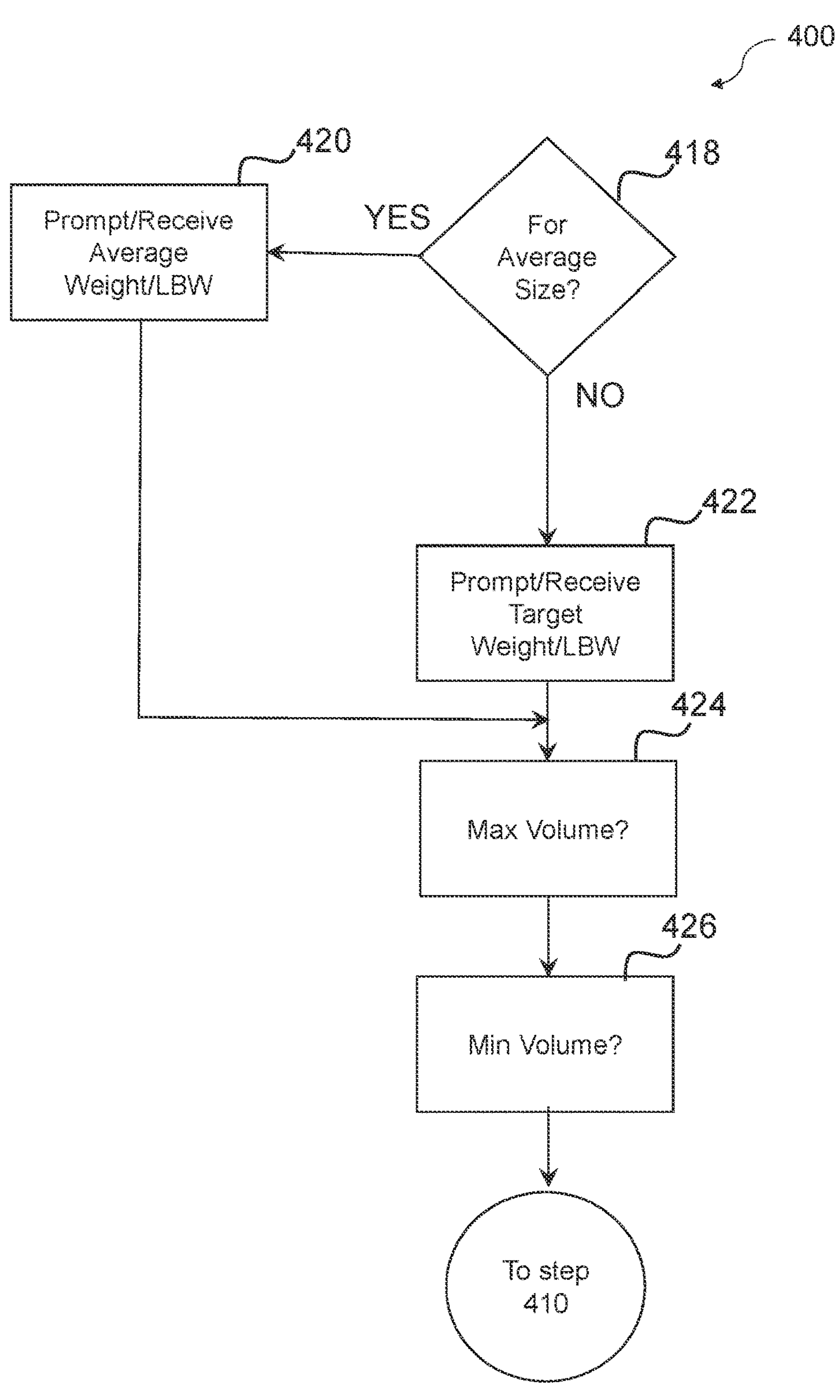

As shown in FIG. 4C, at step 418, process 400 includes, in response to receiving, in step 408, (i) the user response including the indication to adapt a smart protocol based on a size of a patient and (ii) the user response including the indication that a fixed protocol is not for CTA, or receiving, in step 416, (i) the user response including the minimum flow rate of the at least one fluid associated with the fixed protocol, or receiving, in step 428, (i) the user response including the indication that a fixed duration for the smart protocol is acceptable, providing a prompt for an indication of whether the fixed protocol is associated with an average sized patient, receiving a user response including the indication of whether the fixed protocol is associated with an average sized patient, and controlling, based on the indication of whether the fixed protocol is associated with an average sized patient, processing to proceed directly to one of step 420 and step 422 of process 400. For example, injection system 102 may, in response to receiving, in step 408, (i) the user response including the indication to adapt a smart protocol based on a size of a patient and (ii) the user response including the indication that a fixed protocol is not for CTA or receiving, in step 416, (i) the user response including the minimum flow rate of the at least one fluid associated with the fixed protocol, or receiving, in step 428, (i) the user response including the indication that a fixed duration for the smart protocol is acceptable, provide a prompt for an indication of whether the fixed protocol is associated with an average sized patient, receive a user response including the indication of whether the fixed protocol is associated with an average sized patient, and control, based on the indication of whether the fixed protocol is associated with an average sized patient, processing to proceed directly to one of step 420 and step 422 of process 400.

In such an example, injection system 102 may, in response to receiving the user response including an indication that the fixed protocol is associated with an average sized patient, control processing to proceed directly to step 420 of process 400.

In such an example, injection system 102 may, in response to receiving the user response including an indication that the fixed protocol is not associated with an average sized patient, control processing to proceed directly to step 422 of process 400.

As shown in FIG. 4C, at step 420, process 400 includes, in response to receiving the user response including the indication that the fixed protocol is associated with an average sized patient, providing a prompt for at least one of a weight of the average sized patient and a lean body weight of the average sized patient, and receiving a user response including the at least one of the weight of the average sized patient and the lean body weight of the average sized patient. For example, injection system 102 may, in response to receiving the user response including the indication that the fixed protocol is associated with an average sized patient, provide a prompt for at least one of a weight of the average sized patient and a lean body weight of the average sized patient, and receive a user response including the at least one of the weight of the average sized patient and the lean body weight of the average sized patient.

As shown in FIG. 4C, at step 422, process 400 includes, in response to receiving the user response including an indication that the fixed protocol is not associated with an average sized patient, providing a prompt for at least one of a target weight of the patient and a target lean body weight of the patient, and receiving a user response including the at least one of the target weight of the patient and the target lean body weight of the patient. For example, injection system 102 may, in response to receiving the user response including the indication that the fixed protocol is not associated with an average sized patient, provide a prompt for at least one of a target weight of the patient and a target lean body weight of the patient, and receive a user response including the at least one of the target weight of the patient and the target lean body weight of the patient.

As shown in FIG. 4C, at step 424, process 400 includes, in response to receiving (i) the user response including the at least one of the weight of the average sized patient and the lean body weight of the average sized patient or (ii) the user response including the at least one of the target weight of the patient and the target lean body weight of the patient, providing a prompt for a maximum volume of at least one fluid associated with a fixed protocol, and receiving a user response including the maximum volume of at least one fluid associated with a fixed protocol. For example, injection system 102 may, in response to receiving (i) the user response including the at least one of the weight of the average sized patient and the lean body weight of the average sized patient or (ii) the user response including the at least one of the target weight of the patient and the target lean body weight of the patient, provide a prompt for a maximum volume of at least one fluid associated with a fixed protocol, and receive a user response including the maximum volume of at least one fluid associated with a fixed protocol.

As shown in FIG. 4C, at step 426, process 400 includes providing a prompt for a minimum volume of at least one fluid associated with a fixed protocol, and receiving a user response including the minimum volume of at least one fluid associated with a fixed protocol. For example, injection system 102 may provide a prompt for a minimum volume of at least one fluid associated with a fixed protocol, and receive a user response including the minimum volume of at least one fluid associated with a fixed protocol.

In such an example, injection system 102 may, in response to receiving the user response including the minimum volume of at least one fluid associated with a fixed protocol in step 426, control processing to proceed directly to step 410 of process 400.

Figure 4D:
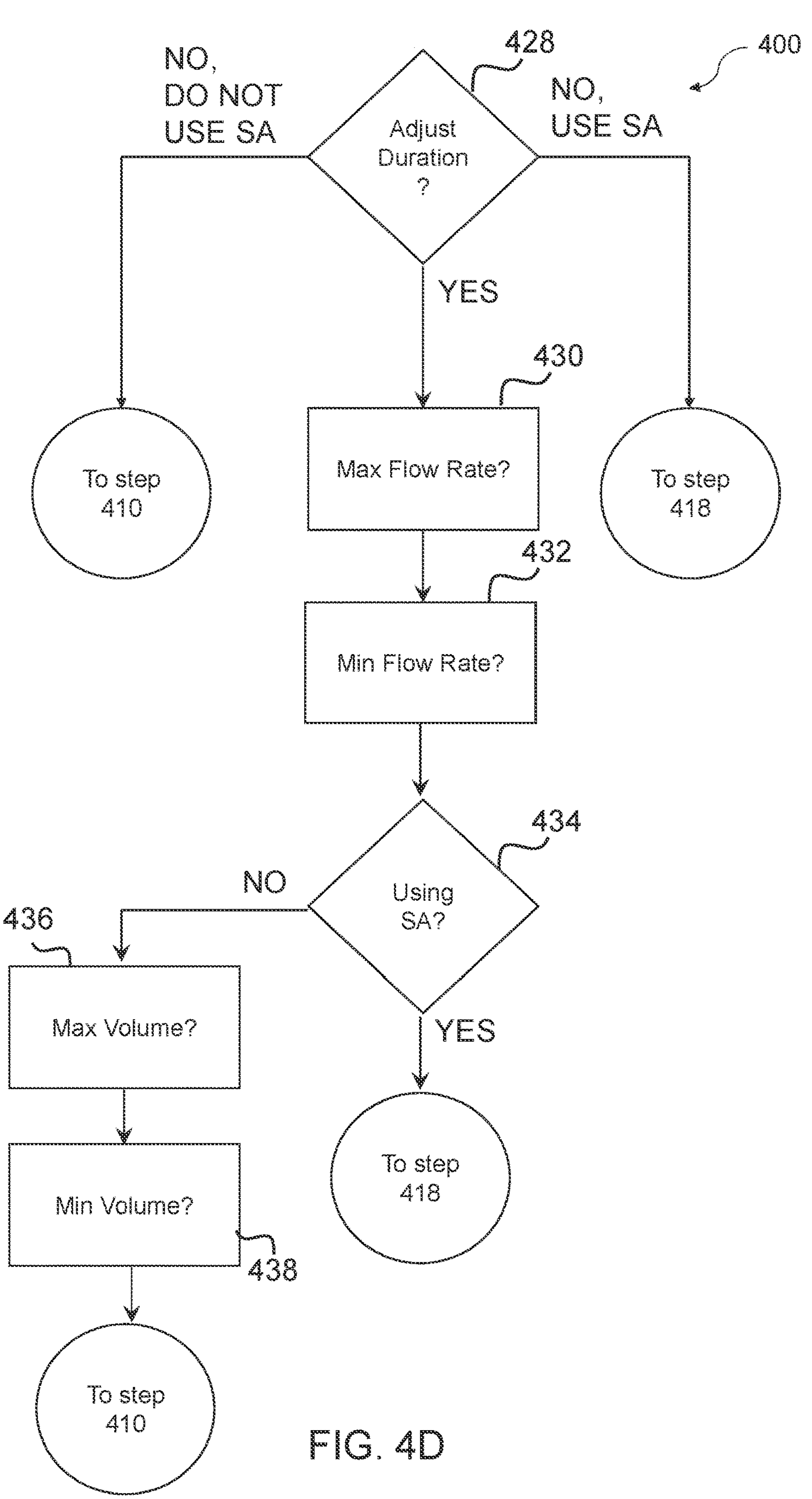

As shown in FIG. 4D, at step 428, process 400 includes, in response to receiving the user response including the indication that a fixed protocol is for CTA in step 408, providing a prompt for an indication of whether a fixed duration for the smart protocol is acceptable, and receiving a user response including the indication of whether a fixed duration for the smart protocol is acceptable, and controlling, based on the user response including the indication of whether a fixed duration for the smart protocol is acceptable, processing to proceed directly to one of step 410, step 418, and step 430 of process 400. For example, injection system 102 may, in response to receiving the user response including the indication that a fixed protocol is for CTA in step 408, provide a prompt for an indication of whether a fixed duration for the smart protocol is acceptable, and receive a user response including the indication of whether a fixed duration for the smart protocol is acceptable, and control, based on the user response including the indication of whether a fixed duration for the smart protocol is acceptable, processing to proceed directly to one of step 410, step 418, and step 430 of process 400

In such an example, in response to receiving the (i) user response including the indication that a fixed duration for the smart protocol is not acceptable and (ii) the user response including the indication to not adapt a smart protocol based on a size of a patient, injection system 102 may control processing to proceed directly to step 410 of process 400.

In such an example, in response to receiving the (i) user response including the indication that a fixed duration for the smart protocol is not acceptable and (ii) the user response including the indication to adapt a smart protocol based on a size of a patient, injection system 102 may control processing to proceed directly to step 418 of process 400.

In such an example, in response to receiving the user response including the indication that a fixed duration for the smart protocol is acceptable, injection system 102 may control processing to proceed directly to step 430 of process 400.

As shown in FIG. 4D, at step 430, process 400 includes, in response to receiving the user response including the indication that a fixed duration for the smart protocol is acceptable, providing a prompt for a maximum flow rate of at least one fluid associated with a fixed protocol, and receiving a user response including the maximum flow rate of at least one fluid associated with a fixed protocol. For example, injection system 102 may, in response to receiving the user response including the indication that a fixed duration for the smart protocol is acceptable, provide a prompt for a maximum flow rate of the at least one fluid associated with the fixed protocol, and receive a user response including the maximum flow rate of the at least one fluid associated with the fixed protocol.

As shown in FIG. 4D, at step 432, process 400 includes providing a prompt for a minimum flow rate of at least one fluid associated with a fixed protocol, and receiving a user response including the minimum flow rate of at least one fluid associated with a fixed protocol. For example, injection system 102 may provide a prompt for a minimum flow rate of the at least one fluid associated with the fixed protocol, and receive a user response including the minimum flow rate of the at least one fluid associated with the fixed protocol.

As shown in FIG. 4D, at step 434, process 400 includes controlling, based on the user response including the indication of whether to adapt a smart protocol based on a size of a patient received in step 406, processing to proceed directly to one of step 418 and step 436 of process 400. For example, injection system 102 may control, based on the user response including the indication of whether to adapt a smart protocol based on a size of a patient received in step 406, processing to proceed directly to one of step 418 and step 436 of process 400.

In such an example, injection system 102 may control, based on the user response received in step 406 including the indication to adapt a smart protocol based on a size of a patient, processing to proceed directly to step 418 of process 400.

In such an example, injection system 102 may control, based on the user response received in step 406 including the indication to not adapt a smart protocol based on a size of a patient, processing to proceed directly to step 436 of process 400.

As shown in FIG. 4D, at step 436, process 400 includes, in response to receiving the user response including the indication to not adapt a smart protocol based on a size of a patient, providing a prompt for a maximum volume of at least one fluid associated with a fixed protocol, and receiving a user response including the maximum volume of at least one fluid associated with a fixed protocol. For example, injection system 102 may provide a prompt for a maximum volume of at least one fluid associated with a fixed protocol, and receive a user response including the maximum volume of at least one fluid associated with a fixed protocol.

As shown in FIG. 4D, at step 438, process 400 includes providing a prompt for a minimum volume of at least one fluid associated with a fixed protocol, and receiving a user response including the minimum volume of at least one fluid associated with a fixed protocol. For example, injection system 102 may provide a prompt for a minimum volume of at least one fluid associated with a fixed protocol, and receive a user response including the minimum volume of at least one fluid associated with a fixed protocol.

In such an example, injection system 102 may, in response to receiving the user response including the minimum volume of at least one fluid associated with a fixed protocol, control processing to proceed directly to step 410 of process 400.

Although embodiments or aspects have been described in detail for the purpose of illustration and description, it is to be understood that such detail is solely for that purpose and that embodiments or aspects are not limited to the disclosed embodiments or aspects, but, on the contrary, are intended to cover modifications and equivalent arrangements that are within the spirit and scope of the appended claims. For example, it is to be understood that the present disclosure contemplates that, to the extent possible, one or more features of any embodiment or aspect can be combined with one or more features of any other embodiment or aspect. In fact, any of these features can be combined in ways not specifically recited in the claims and/or disclosed in the specification. Although each dependent claim listed below may directly depend on only one claim, the disclosure of possible implementations includes each dependent claim in combination with every other claim in the claim set.

What is claimed is:

1. A system, comprising:

at least one processor programmed and/or configured to:

obtain a fixed protocol including the following fixed protocol parameters according to which an injection system is configured to control delivery of at least one fluid including an iodine-based contrast media to a patient in an injection: a flow rate of the at least one fluid to be delivered to the patient in at least one phase of the injection and a volume of the at least one fluid to be delivered to the patient in the at least one phase of the injection;

provide, via a user interface of a computing device, a series of prompts, and receive, via the user interface of the computing device, a series of user responses in response to the series of prompts;

generate, based on the series of user responses and the fixed protocol, a smart protocol that includes an iodine dose/load (IDL)-based protocol or an iodine delivery rate (IDR)-based protocol that is configured to determine the following smart protocol parameters specific to the patient, the contrast media, and a scanner and according to which the injection system is configured to control delivery of the at least one fluid to the patient in the injection: a number of units of the contrast media to be delivered per a unit of weight and one of a contrast media load and a contrast media delivery rate;

receive, via the user interface of the computing device, user input associated with the smart protocol for the injection;

calculate, based on the user input, values of the smart protocol parameters of the smart protocol;

calculate, from (i) the values of the smart protocol parameters, (ii) a concentration of the iodine-based contrast media, and (iii) an injection duration, a contrast-phase flow rate and a contrast-phase volume that satisfy the one of the contrast media load and the contrast media delivery rate; and control, according to the contrast-phase flow rate and the contrast-phase volume, the injection system to deliver the at least one fluid including the iodine-based contrast media to the patient in the injection.

2. The system of claim 1, wherein the at least one processor is further programmed and/or configured to:

determine, based on whether the fixed protocol is bi-phasic, whether the fixed protocol is eligible to be converted to the smart protocol.

3. The system of claim 1, wherein the computing device includes at least one of the following: the injection system, a user device, or any combination thereof.

4. The system of claim 1, wherein the at least one processor is further programmed and/or configured to:

provide, via the user interface of the computing device, in response to receiving a user response of the user responses, information associated with a change in the smart protocol generated by that user response.

5. The system of claim 1, wherein the user input includes at least one of the following: a weight of the patient, a lean body weight of the patient, a body surface area of the patient, or any combination thereof.

6. The system of claim 1, wherein the series of prompts and the series of user responses thereto include a prompt and a corresponding user response thereto for at least one of the following: a concentration of the contrast media; an indication of whether the fixed protocol is adapted based on a size of the patient; an indication of whether to adapt the smart protocol based on the size of the patient; an indication of whether the fixed protocol is for computed tomography angiography (CTA); an indication of whether a duration of the fixed protocol is adjusted based on a duration of a CTA scan; a maximum flow rate of the at least one fluid associated with the fixed protocol; a minimum flow rate of the at least one fluid associated with the fixed protocol; a maximum volume of the at least one fluid associated with the fixed protocol; a minimum volume of the at least one fluid associated with the fixed protocol; an indication of whether the fixed protocol is associated with an average sized patient; a weight of the average sized patient; a lean body weight of the average sized patient; a target weight of the patient; a target lean body weight of the patient; an indication of a type of delivery method associated with the fixed protocol; an indication of whether a fixed duration for the smart protocol is acceptable; or any combination thereof.

7. The system of claim 6, wherein the series of prompts and the series of user responses thereto include a prompt and a corresponding user response thereto for the indication of the type of delivery method associated with the fixed protocol, and wherein the indication of the type of delivery method associated with the fixed protocol includes a bolus tracking delivery method or a fixed delays delivery method.

8. The system of claim 1, wherein the at least one processor is programmed and/or configured to provide the series of prompts, and receive the series of user responses in response to the series of prompts, by:

providing a prompt for a concentration of the contrast media, and receiving a user response including the concentration of the contrast media;

providing a prompt for an indication of whether the fixed protocol is adapted based on a size of the patient, and receiving a user response including the indication of whether the fixed protocol is adapted based on the size of the patient;

in response to receiving a user response including an indication that the fixed protocol is adapted based on the size of the patient, providing a prompt for an indication of whether to adapt the smart protocol based on the size of the patient, and receiving a user response including the indication of whether to adapt the smart protocol based on a size of the patient;

in response to (i) receiving a user response including an indication that the fixed protocol is not adapted based on the size of the patient or (ii) receiving the user response including the indication of whether to adapt the smart protocol based on the size of the patient, providing a prompt for an indication of whether the fixed protocol is for computed tomography angiography (CTA), and receiving a user response including the indication of whether the fixed protocol is for CTA;

providing a prompt for an indication of a type of delivery method associated with the fixed protocol, and receiving a user response including the indication of the type of delivery method associated with the fixed protocol;

in response to receiving the user response including the indication that the type of delivery method associated with the fixed protocol is a bolus tracking delivery method, providing a prompt for an indication of whether a duration of the fixed protocol is adjusted based on a duration of a CTA scan, and receiving a user response including the indication of whether a duration of the fixed protocol is adjusted based on the duration of the CTA scan;

in response to (i) receiving a user response including an indication that the type of delivery method associated with the fixed protocol is a fixed delays delivery method or (ii) receiving a user response including the indication that the duration of the fixed protocol is adjusted based on the duration of the CTA scan, providing a prompt for a maximum flow rate of the at least one fluid associated with the fixed protocol, and receiving a user response including the maximum flow rate of the at least one fluid associated with the fixed protocol;

in response to receiving the user response including the maximum flow rate of the at least one fluid associated with the fixed protocol, providing a prompt for a minimum flow rate of the at least one fluid associated with the fixed protocol, and receiving a user response including the minimum flow rate of the at least one fluid associated with the fixed protocol;

in response to receiving (i) the user response including the indication to adapt the smart protocol based on the size of the patient and (ii) the user response including the indication that the fixed protocol is not for CTA or receiving (i) the user response including the minimum flow rate of the at least one fluid associated with the fixed protocol, or receiving (i) the user response including the indication that a fixed duration for the smart protocol is acceptable, providing a prompt for an indication of whether the fixed protocol is associated with an average sized patient, and receiving a user response including the indication of whether the fixed protocol is associated with the average sized patient;

in response to receiving the user response including the indication that the fixed protocol is associated with the average sized patient, providing a prompt for at least one of a weight of the average sized patient and a lean body weight of the average sized patient, and receiving a user response including the at least one of the weight of the average sized patient and the lean body weight of the average sized patient;

in response to receiving the user response including the indication that the fixed protocol is not associated with the average sized patient, providing a prompt for at least one of a target weight of the patient and a target lean body weight of the patient, and receiving a user response including the at least one of the target weight of the patient and the target lean body weight of the patient;

in response to receiving (i) the user response including the at least one of the weight of the average sized patient and the lean body weight of the average sized patient or (ii) the user response including the at least one of the target weight of the patient and the target lean body weight of the patient, providing a prompt for a maximum volume of the at least one fluid associated with the fixed protocol, and receiving a user response including the maximum volume of the at least one fluid associated with the fixed protocol;

in response to receiving the user response including the maximum volume of the at least one fluid associated with the fixed protocol, providing a prompt for a minimum volume of the at least one fluid associated with the fixed protocol, and receiving a user response including the minimum volume of the at least one fluid associated with the fixed protocol;

in response to receiving the user response including the indication that the fixed protocol is for CTA, providing a prompt for an indication of whether the fixed duration for the smart protocol is acceptable, and receiving a user response including the indication of whether the fixed duration for the smart protocol is acceptable;

in response to receiving the user response including the indication that the fixed duration for the smart protocol is acceptable, providing the prompt for the maximum flow rate of the at least one fluid associated with the fixed protocol, and receiving the user response including the maximum flow rate of the at least one fluid associated with the fixed protocol; and in response to receiving the user response including the indication to not adapt the smart protocol based on the size of the patient, providing a prompt for the maximum volume of the at least one fluid associated with the fixed protocol, and receiving the user response including the maximum volume of the at least one fluid associated with the fixed protocol.

9. A computer program product comprising at least one non-transitory computer-readable medium including program instructions that, when executed by at least one processor, cause the at least one processor to:

obtain a fixed protocol including the following fixed protocol parameters according to which an injection system is configured to control delivery of at least one fluid including an iodine-based contrast media to a patient in an injection: a flow rate of the at least one fluid to be delivered to the patient in at least one phase of the injection and a volume of the at least one fluid to be delivered to the patient in the at least one phase of the injection;

provide, via a user interface of a computing device, a series of prompts, and receive, via the user interface of the computing device, a series of user responses in response to the series of prompts;

generate, based on the series of user responses and the fixed protocol, a smart protocol that includes an iodine dose/load (IDL)-based protocol or an iodine delivery rate (IDR)-based protocol that is configured to determine the following smart protocol parameters specific to the patient, the contrast media, and a scanner and according to which the injection system is configured to control delivery of the at least one fluid to the patient in the injection: a number of units of the contrast media to be delivered per a unit of weight and one of a contrast media load and a contrast media delivery rate;

receive, via the user interface of the computing device, user input associated with the smart protocol for the injection;

calculate, based on the user input, values of the smart protocol parameters of the smart protocol;

calculate, from (i) the values of the smart protocol parameters, (ii) a concentration of the iodine-based contrast media, and (iii) an injection duration, a contrast-phase flow rate and a contrast-phase volume that satisfy the one of the contrast media load and the contrast media delivery rate; and control, according to the contrast-phase flow rate and the contrast-phase volume, the injection system to deliver the at least one fluid including the iodine-based contrast media to the patient in the injection.

10. The computer program product of claim 9, wherein the program instructions, when executed by the at least one processor, further cause the at least one processor to:

determine, based on whether the fixed protocol is biphasic, whether the fixed protocol is eligible to be converted to the smart protocol.

11. The computer program product of claim 9, wherein the computing device includes at least one of the following: the injection system, a user device, or any combination thereof.

12. The computer program product of claim 9, wherein the program instructions, when executed by the at least one processor, further cause the at least one processor to:

provide, via the user interface of the computing device, in response to receiving a user response of the user responses, information associated with a change in the smart protocol generated by that user response.

13. The computer program product of claim 9, wherein the user input includes at least one of the following: a weight of the patient, a lean body weight of the patient, a body surface area of the patient, or any combination thereof.

14. The computer program product of claim 9, wherein the series of prompts and the series of user responses thereto include a prompt and a corresponding user response thereto for at least one of the following: a concentration of the contrast media; an indication of whether the fixed protocol is adapted based on a size of the patient; an indication of whether to adapt the smart protocol based on the size of the patient; an indication of whether the fixed protocol is for computed tomography angiography (CTA); an indication of whether a duration of the fixed protocol is adjusted based on a duration of a CTA scan; a maximum flow rate of the at least one fluid associated with the fixed protocol; a minimum flow rate of the at least one fluid associated with the fixed protocol; a maximum volume of the at least one fluid associated with the fixed protocol; a minimum volume of the at least one fluid associated with the fixed protocol; an indication of whether the fixed protocol is associated with an average sized patient; a weight of the average sized patient; a lean body weight of the average sized patient; a target weight of the patient; a target lean body weight of the patient; an indication of a type of delivery method associated with the fixed protocol; an indication of whether a fixed duration for the smart protocol is acceptable; or any combination thereof.

15. The computer program product of claim 14, wherein the series of prompts and the series of user responses thereto include a prompt and a corresponding user response thereto for the indication of the type of delivery method associated with the fixed protocol, and wherein the indication of the type of delivery method associated with the fixed protocol includes a bolus tracking delivery method or a fixed delays delivery method.

16. The computer program product of claim 9, wherein the program instructions, when executed by the at least one processor, further cause the at least one processor to provide the series of prompts and receive the series of user responses in response to the series of prompts further by:

providing a prompt for a concentration of the contrast media, and receiving a user response including the concentration of the contrast media;

providing a prompt for an indication of whether the fixed protocol is adapted based on a size of the patient, and receiving a user response including the indication of whether the fixed protocol is adapted based on the size of the patient;

in response to receiving a user response including an indication that the fixed protocol is adapted based on the size of the patient, providing a prompt for an indication of whether to adapt the smart protocol based on the size of the patient, and receiving a user response including the indication of whether to adapt the smart protocol based on a size of the patient;

in response to (i) receiving a user response including an indication that the fixed protocol is not adapted based on the size of the patient or (ii) receiving the user response including the indication of whether to adapt the smart protocol based on the size of the patient, providing a prompt for an indication of whether the fixed protocol is for computed tomography angiography (CTA), and receiving a user response including the indication of whether the fixed protocol is for CTA;

providing a prompt for an indication of a type of delivery method associated with the fixed protocol, and receiving a user response including the indication of the type of delivery method associated with the fixed protocol;

in response to receiving the user response including the indication that the type of delivery method associated with the fixed protocol is a bolus tracking delivery method, providing a prompt for an indication of whether a duration of the fixed protocol is adjusted based on a duration of a CTA scan, and receiving a user response including the indication of whether a duration of the fixed protocol is adjusted based on the duration of the CTA scan;

in response to (i) receiving a user response including an indication that the type of delivery method associated with the fixed protocol is a fixed delays delivery method or (ii) receiving a user response including the indication that the duration of the fixed protocol is adjusted based on the duration of the CTA scan, providing a prompt for a maximum flow rate of the at least one fluid associated with the fixed protocol, and receiving a user response including the maximum flow rate of the at least one fluid associated with the fixed protocol;

in response to receiving the user response including the maximum flow rate of the at least one fluid associated with the fixed protocol, providing a prompt for a minimum flow rate of the at least one fluid associated with the fixed protocol, and receiving a user response including the minimum flow rate of the at least one fluid associated with the fixed protocol;

in response to receiving (i) the user response including the indication to adapt the smart protocol based on the size of the patient and (ii) the user response including the indication that the fixed protocol is not for CTA or receiving (i) the user response including the minimum flow rate of the at least one fluid associated with a fixed protocol, or receiving (i) the user response including the indication that a fixed duration for the smart protocol is acceptable, providing a prompt for an indication of whether the fixed protocol is associated with an average sized patient, and receiving a user response including the indication of whether the fixed protocol is associated with the average sized patient;

in response to receiving the user response including the indication that the fixed protocol is associated with the average sized patient, providing a prompt for at least one of a weight of the average sized patient and a lean body weight of the average sized patient, and receiving a user response including the at least one of the weight of the average sized patient and the lean body weight of the average sized patient;

in response to receiving the user response including the indication that the fixed protocol is not associated with the average sized patient, providing a prompt for at least one of a target weight of the patient and a target lean body weight of the patient, and receiving a user response including the at least one of the target weight of the patient and the target lean body weight of the patient;

in response to receiving (i) the user response including the at least one of the weight of the average sized patient and the lean body weight of the average sized patient or (ii) the user response including the at least one of the target weight of the patient and the target lean body weight of the patient, providing a prompt for a maximum volume of the at least one fluid associated with the fixed protocol, and receiving a user response including the maximum volume of the at least one fluid associated with the fixed protocol;

in response to receiving the user response including the maximum volume of the at least one fluid associated with the fixed protocol, providing a prompt for a minimum volume of the at least one fluid associated with the fixed protocol, and receiving a user response including the minimum volume of the at least one fluid associated with the fixed protocol;

in response to receiving the user response including the indication that the fixed protocol is for CTA, providing a prompt for an indication of whether the fixed duration for the smart protocol is acceptable, and receiving a user response including the indication of whether the fixed duration for the smart protocol is acceptable;

in response to receiving the user response including the indication that the fixed duration for the smart protocol is acceptable, providing the prompt for the maximum flow rate of the at least one fluid associated with the fixed protocol, and receiving the user response including the maximum flow rate of the at least one fluid associated with the fixed protocol; and in response to receiving the user response including the indication to not adapt the smart protocol based on the size of the patient, providing a prompt for the maximum volume of the at least one fluid associated with the fixed protocol, and receiving the user response including the maximum volume of the at least one fluid associated with the fixed protocol.

17. A computer-implemented method, comprising:

obtaining, with at least one processor, a fixed protocol including the following fixed protocol parameters according to which an injection system is configured to control delivery of at least one fluid including an iodine-based contrast media to a patient in an injection: a flow rate of the at least one fluid to be delivered to the patient in at least one phase of the injection and a volume of the at least one fluid to be delivered to the patient in the at least one phase of the injection;

providing, with the at least one processor, via a user interface of a computing device, a series of prompts, and receiving, with the at least one processor, via the user interface of the computing device, a series of user responses in response to the series of prompts; and generating, with the at least one processor, based on the series of user responses and the fixed protocol, a smart protocol that includes an iodine dose/load (IDL)-based protocol or an iodine delivery rate (IDR)-based protocol that is configured to determine the following smart protocol parameters specific to the patient, the contrast media, and a scanner and according to which the injection system is configured to control delivery of the at least one fluid to the patient in the injection: a number of units of the contrast media to be delivered per a unit of weight-and one of a contrast media load and a contrast media delivery rate;

receiving, with the at least one processor, via the user interface of the computing device, user input associated with the smart protocol for the injection;

calculating, with the at least one processor, based on the user input, values of the smart protocol parameters of the smart protocol;

calculating, from (i) the values of the smart protocol parameters, (ii) a concentration of the iodine-based contrast media, and (iii) an injection duration, a contrast-phase flow rate and a contrast-phase volume that satisfy the one of the contrast media load and the contrast media delivery rate; and controlling, with the least one processor, according to the contrast-phase flow rate and the contrast-phase volume, the injection system to deliver the at least one fluid including the iodine-based contrast media to the patient in the injection.

* * * * *